(12) United States Patent
Liang et al.

(10) Patent No.: US 8,822,434 B2
(45) Date of Patent: Sep. 2, 2014

(54) COMPOSITIONS AND METHODS TO TREAT CARDIAC DISEASES

(75) Inventors: Bruce Liang, Avon, CT (US); Kenneth A. Jacobson, Silver Spring, MD (US); Bhalchandra V. Joshi, Madison, AL (US); Thatikonda Santhosh Kumar, Gaithersburg, MD (US)

(73) Assignees: The University of Connecticut, Farmington, CT (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 504 days.

(21) Appl. No.: 13/031,805

(22) Filed: Feb. 22, 2011

(65) Prior Publication Data

US 2011/0212924 A1 Sep. 1, 2011

Related U.S. Application Data

(60) Provisional application No. 61/306,687, filed on Feb. 22, 2010.

(51) Int. Cl.
*A61K 31/675* (2006.01)
*C07F 9/6561* (2006.01)

(52) U.S. Cl.
USPC ............................................. 514/81; 544/244

(58) Field of Classification Search
CPC .......................... C07F 9/65616; A61K 31/675
USPC ............................................. 514/81; 544/244
See application file for complete search history.

(56) References Cited

U.S. PATENT DOCUMENTS

| | | |
|---|---|---|
| 6,255,292 B1 | 7/2001 | Liang |
| 6,329,349 B1 | 12/2001 | Liang et al. |
| 6,586,413 B2 | 7/2003 | Liang et al. |
| 6,677,356 B1 | 1/2004 | Sethi et al. |
| 7,087,589 B2 | 8/2006 | Jacobson et al. |
| 2003/0092668 A1 | 5/2003 | Liang et al. |
| 2003/0186929 A1 | 10/2003 | Liang et al. |
| 2003/0216412 A1 | 11/2003 | Jacobson et al. |
| 2007/0281908 A1 | 12/2007 | Liang et al. |

FOREIGN PATENT DOCUMENTS

| | | |
|---|---|---|
| WO | 0151490 A1 | 7/2001 |
| WO | 2006031505 A1 | 3/2006 |
| WO | 2006091905 A1 | 8/2006 |

OTHER PUBLICATIONS

International Search Report; International Application No. PCT/US2011/025680; International Filing Date Feb. 22, 2011; Date of Mailing Nov. 3, 2011; 10 pages.
Koh, et al.; "Design, Synthesis, and Antiviral Activity of Adenosine 5'-Phosphonate Analogues as Chain Terminators against Hepatitis C Virus"; J. Med. Chem.; 48; pp. 2867-2875; (2005).
Kumar, et al.; "Structure—Activity Relationship of (N)-Methanocarba Phosphonate Analogues of 5'-AMP as Cardioprotective Agents Acting Through a Cardiac P2X Receptor"; J. Med. Chem.; 53; pp. 2562-2576; (2010).
International Search Report and Written Opinion; International Application No. PCT/US2011/025680; International Filing Date Feb. 22, 2011; Date of Mailing Jan. 31, 2012; 22 pages.
Shen, et al.; "P2X Purinergic Receptor-Mediated Ionic Current in Cardiac Myocytes of Calsequestrin Model of Cardiomyopathy: Implications for the Treatment of Heart Failure"; Am J Physiol Heart Circ Physiol; 292; H1077-Y1084; (2007).
Zhou, et al.; "Treatment of Heart Failure by a Methanocarba Derivative of Adenosine Monophosphate: Implication for a Role of Cardiac Purinergic P2X Receptors"; Journal of Pharmacology and Experimental Therapeutics; 333; pp. 920-928; (2010).
"2009 Focused Update Incorporated Into the ACC/AHA 2005 Guidelines for the Diagnosis and Management of Heart Failure in Adults"; J. Am. Coll. Cardiol.; Published on-line, 92 pages; Mar. 26, 2009.
Brown, et al.; "Activity of Novel Adenine Nucleotide Derivatives as Agonists and Antagonists at Recombinant Rat P2X Receptors"; Drug Development Research; 49; pp. 253-259; (2000).
Dhalla et al.; "Alterations in Heart Membrane Calcium Transport During the Development of Ischemia-Reperfusion Injury"; J. Molecular and Cellular Cardiology; 20(20); Abstract only; (1988).
Gao, et al.; "Spinal P2X Receptor Modulates Reflex Pressor Response to Activation of Muscle Afferents"; Am J Physiol Heart Circ Physiol; 288; pp. H2238-H2243; (2005).
Hiroke, et al.; "ATP Induces Cardiomyocyte Hypertrophy Through the Calcineurin Dependent Ca2+ Signaling Pathway"; Circulation; 100; p. I. 628; (1999); XP008085345.
Hu, et al.; "A Novel contractile Phenotype with Cardiac Transgenic expression of the Human P2X4 Receptor1"; The FASEB Journal; 15; pp. 2739-2741; (2001).
Janardhanan, et al.; "Therapeutic Approach to Diastolic Dysfunction"; Current Hypertens. Rep.; 11(4); pp. 283-291; (2009).
Kim, et al.; "2-Substitution of Adenine Nucleotide Analogues Containing a Bicyclo[3.1.0]hexane Ring System Locked in a Northern Conformation: Enhanced Potency as P2Y1 Receptor Antagonists"; Journal of Medicinal Chemistry, vol. 46, No. 23, 2003, pp. 4974-4987.
Knollmann, et al.; "Remodeling of Ionic Currents in Hypertrophied and Failing Hearts of Transgenic Mice Overexpressing Calsequestrin"; Journal of Physiology; 525; pp. 483-498; (2000).

(Continued)

*Primary Examiner* — Golam M M Shameem
*Assistant Examiner* — Laura Daniel
(74) *Attorney, Agent, or Firm* — Cantor Colburn LLP

(57) ABSTRACT

Phosphonate and phosphinate N-methanocarba derivatives of AMP including their prodrug analogs are described. MRS2339, a 2-chloro-AMP derivative containing a (N)-methanocarba (bicyclo[3.1.0]hexane) ring system in place of ribose, activates P2X receptors, ligand-gated ion channels. Phosphonate analogs of MRS2339 were synthesized using Michaelis-Arbuzov and Wittig reactions, based on the expectation of increased half-life in vivo due to the stability of the C—P bond. When administered to calsequestrin-overexpressing mice (a genetic model of heart failure) via a mini-osmotic pump (Alzet), some analogs significantly increased intact heart contractile function in vivo, as assessed by echocardiography-derived fractional shortening (FS) as compared to vehicle-infused mice. The range of carbocyclic nucleotide analogs for treatment of heart failure has been expanded.

9 Claims, 7 Drawing Sheets

(56) References Cited

OTHER PUBLICATIONS

Komamura, et al.; "Alterations in Left Ventricular Diastolic Function in Conscious Dogs with Pacing-Induced Heart Failure"; J. Clin. Invest; 89; pp. 1825-1838; (1992).

Lambrecht, et al.; "Structure-Activity Relationships of Suramin and Pyridoxal-5'-phosphate Derivates as P2 Receptor Antagonists"; Current pharmaceutical Design; 8; pp. 2371-2399; (2002).

Liu; "A New Epidemic of Heart Failure in the United States: Findings from the national Hospital Discharge Surveys, 1980-2006"; Cir. 18; S1092; Abstract only, 2 pages; (2008).

Liu, Longjian; "Changes in Cardiovascular Hospitalization and Comorbidity of Heart failure in the United States: Findings ffrom the national Hospital Discharge Surveys 1980-2006"; International Journal of Cardiology xxx (2010) Article in Press: IJCA-12412; 7 pages.

Mahaut-Smith, et al.; "ADP Is Not an Agonist at P2X(1) Receptors: Evidence for Separate Receptors Stimulated by ATP and ADP on Human Platelets"; British Journal of Pharmacology; 131; pp. 108-114; (2000); XP008085367.

Mei, et al.; "P2 Purinergic Receptor Activation Enhances Cardiac Contractility in Isolated Rat and Mouse Hearts"; Am. J. Physiol Heart Circ. Physiol.; 281; pp. H334-H341; (2001).

North, R. Alan; "Molecular Physiology of P2X Receptors"; Physiol. Rev.; 82; pp. 1013-1067;(2002).

O'Rourke, et al.; "Mechanisms of Altered Excitation-Contraction Coupling in Canine Tachycardia-Induced Heart Failure, I: Experimental Studies"; Circ. Res.; 84; pp. 562-570; (1999).

Ohara, et al.; "Evolving Focus on Diastolic Dysfunction in Patients with Coronary Artery Disease"; Curr. Opin Cardiol.; 25; pp. 613-621; (2010).

Opie, et al.; "Controversies in Ventricular Remodeling"; Lancet; 367; pp. 356-367; (2006).

Parker et al.; "An ATP-Activated Nonselective Cation Channel in G uinea Pig Ventricular Myocytes"; American Journal of Physiology; 269; pp. H789-H797; (1995).

Ravi, et al.; "Adenine Nucleotide Analogues Locked in a Nothern Methanocarba Conformation: Enhanced Stability and Potency as P2Y1 Receptor Agonists"; Journal of Medicinal Chemistry; vol. 45, No. 10, 2002, pp. 2090-2100.

Saks, et al.; "Quantitative Evaluation of Relationship Between Cardiac Energy Metabolism and Post-Ischemic Recovery of Contractile Function"; J. Molecular and Cellular Cardiology; 21(10); Abstract only; (1998).

SCAMPSd, Frederique et al.; "Pharmacological Profile of the ATP-Mediated Increase in L-Type Calcium Current Amplitude and Activation of a Non-Specific Cationic Current in Rat Ventricular Cells"; Br. J. Pharmacol.; 113; pp. 982-986; (1994).

Shannon, et al.; "Effects of Renin Inhibition Compared to Angiotensin Converting Enzyme Inhibition in Conscious Dogs with Pacing-Induced Heart Failure"; Cardiovascular Research; 34; pp. 464-472; (1997).

Shen et al.; "Extracellular ATP-Stimulated Current in Wild-Type and P2X4 Receptor Transgenic Mouse Ventricular Myocytes: Implications for a Cardiac Physiologic Role of P2X4 Receptors"; The FASEB Journal; 20; pp. 277-282; (2006).

Sonin et al.; "Role of P2X Purinergic Receptors in the Rescue of Ischemic Heart Failure"; Am. J. Physiol Heart Circ Physiol; 295; pp. H1191-H1197; (2008).

Tenenbaum, et al.; "Toward a Redefinition of Ischemic Cardiomyopathy: Is It an Indivisible Entity?"; J. Am. Coll. Cardiol.; 40; pp. 205-206; (2002).

Terracciano, et al.; "Clinical Recovery from End-Stage Heart Failure Using Left-Ventricular Assist Device and Pharmacological therapy Correlates with Increased Sarcoplasmic Reticulum Calcium Content but Not with Regression of Cellular Hypertrophy"; Circulation; 109; pp. 2263-2265; 92004).

Ukai, et al.; "Allopurinol Enhances the Contractile Response to Dobutamine and Exercise in Dogs with Pacing-Induced Heart Failure"; Circulation; 103; pp. 750-755; (2001).

Xu et al.; "Characterization of a Stimulatory Adenosine A2a Receptor in Adult Rat Ventricular Myocyte"; American J. Physiol.; 270; pp. H1655-H1661; (1996).

Yang, et al.; "A Beneficial Role of Cardiac p2X4 Receptors in Heart Failure: Rescue of the Calsequestrin Overexpression Model of Cardiomyopathy"; Am. J. Physio. Heart Circ. Physiol.; 287; pp. H1096-H1103; (2004).

COMPOSITIONS AND METHODS TO TREAT CARDIAC DISEASES

REFERENCE TO CROSS-RELATED APPLICATIONS

This application claims priority to U.S. Provisional Application 61/306,687 filed on Feb. 22, 2010, which is incorporated herein by reference in its entirety.

STATEMENT REGARDING FEDERALLY SPONSORED RESEARCH & DEVELOPMENT

This invention was made with government support under Grant No. R01-HL48225 awarded by the National Institutes of Health. The government has certain rights in the invention.

BACKGROUND

The actions of extracellular nucleotides in cell signaling are mediated by two classes of cell surface purinergic receptors: P2X receptors are ligand-gated ion channels activated by extracellular ATP, and P2Y receptors are G protein-coupled receptors activated by both adenine and uracil nucleotides. In the heart, for example, a variety of P2 receptors are expressed.

Cardiac P2X receptors represent a novel and potentially important therapeutic target for the treatment of heart failure. A P2X receptor on the cardiomyocyte mediates cardioprotection and is activated by ATP or its potent analogue 2-MeSATP 1, as demonstrated using the calsequestrin (CSQ) model of cardiomyopathy. Extracellular ATP can cause an ionic current in murine, rat, and guinea pig cardiac ventricular myocytes. The $P2X_4$ receptor is an important subunit of the native cardiac P2X receptor, which mediates ionic current induced by extracellular ATP. This P2X current was up-regulated in cardiac ventricular myocytes of the CSQ hearts. Furthermore, cardiac myocyte-specific overexpression of the $P2X_4$ receptor can mimic the beneficial effects following chronic infusion of P2X agonist analogues. This analysis suggested that regulation of this cardiac P2X receptor is protective in cardiac hypertrophy or failure.

(1'S,2'R,3'S,4'R,5'S)-4-(6-amino-2-chloro-9H-purin-9-yl)-1-[phosphoryloxymethyl]bicyclo[3.1.0]hexane-2,3-diol, (MRS2339, 3) is an (N)-methanocarba monophosphate derivative of 2-chloro-AMP 2 that contains a rigid bicyclic ring system (bicyclo[3.1.0]hexane) in place of ribose. This ring system impedes hydrolysis of the 5'-phosphate in a model compound by its nucleotidase. Compound 3 induced a current in the CSQ myocyte similar to that by compound 1, characteristic of the action of the $P2X_4$ receptor. Chronically administered MRS2339 (compound 3) rescued the hypertrophic and heart failure phenotype in the CSQ-overexpressing mouse. When administered via an Alzet mini-osmotic pump, it significantly increased longevity as compared to vehicle-injected mice. The improvement in survival was associated with decreases in heart weight/body weight ratio and in cross-section area of the cardiac myocytes. Compound 3 was devoid of any vasodilator action in aorta ring preparations indicating that its salutary effect in heart failure was not due to any vascular unloading.

Activation of this myocyte P2X receptor leads to the opening of a nonselective cation channel permeable to $Na^+$, $K^+$, and $Ca^{2+}$. The current is inward at negative membrane potentials, reverses near 0 mV, and becomes outward at positive potentials. The continuous activation of this receptor channel under the resting or negative membrane potentials would produce an inward current while its activation during depolarized portions of the action potential should lead to an outward current. These ionic currents represent a possible ionic mechanism by which the cardiomyocyte P2X channel achieves its protective effect.

What is needed are additional myocyte P2X receptor activators that have cardioprotection activity.

SUMMARY

In one aspect, disclosed herein are phosphonate and phosphinate N-methanocarba derivatives of AMP comprising

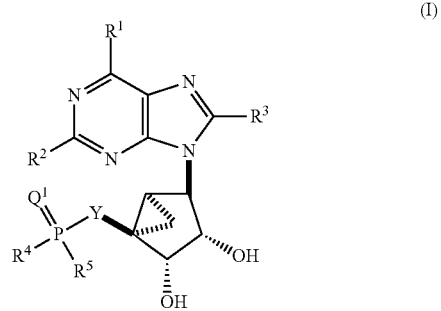

(I)

wherein
$Q^1$ is O or S;
$R^1$ is hydrogen, optionally substituted alkyl, optionally substituted cycloalkyl, halogen, or $N(R^6)_2$, wherein each $R^6$ is independently hydrogen, optionally substituted alkyl, or optionally substituted cycloalkyl;
$R^2$ is hydrogen, optionally substituted alkyl, optionally substituted cycloalkyl, optionally substituted alkynyl, $N(R^6)_2$, or halogen;
$R^3$ is hydrogen, optionally substituted alkyl, $N(R^6)_2$, or halogen;
$R^4$ is hydroxyl, optionally substituted alkyl, optionally substituted alkoxy, optionally substituted aryl, optionally substituted —Oaryl, or $N(R^6)_2$;
$R^5$ is hydroxyl, optionally substituted alkyl, optionally substituted alkoxy, optionally substituted aryl, or optionally substituted —Oaryl; or
alternatively, $R^4$ and $R^5$ form a 5- or 6-membered cyclic structure with the phosphorus atom where the cyclic structure contains at least two oxygen atoms and at least 2 or 3 carbon atoms, wherein the carbon atoms are optionally substituted with alkyl or aryl where the chain is attached; and
Y is a linking group linked to the phosphorus atom by a carbon atom;
or

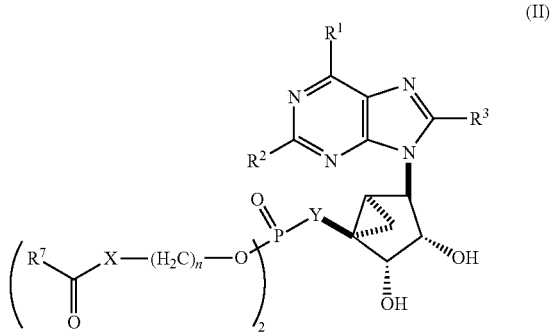

(II)

wherein X is O or S; n is 1, 2, or 3; and $R^7$ is optionally substituted alkyl or optionally substituted aryl;

or

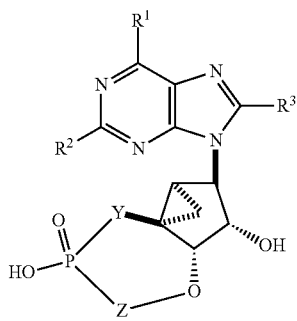

(III)

wherein Z is a bond or —O—C(=O)— where the carbonyl carbon is bonded to the oxygen of the bicycle group and the oxygen is bonded to the phosphorus atom;

or

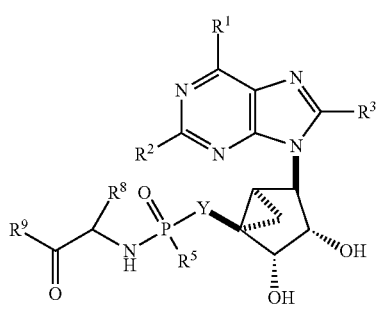

(IV)

wherein $R^8$ is hydrogen or optionally substituted alkyl; and $R^8$ is optionally substituted alkyl, optionally substituted alkoxy, or optionally substituted aryl;

or

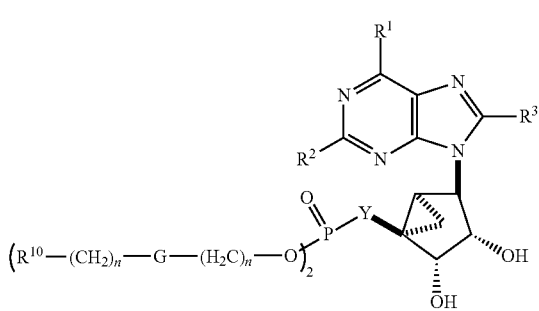

(V)

wherein G is O or S—S; and $R^{10}$ is hydrogen, hydroxyl, optionally substituted alkyl, optionally substituted alkoxy, or optionally substituted aryl; or

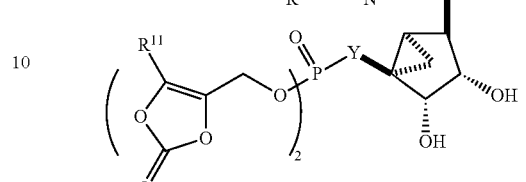

(VI)

wherein $R^{11}$ is hydrogen, optionally substituted alkyl, or optionally substituted aryl; or

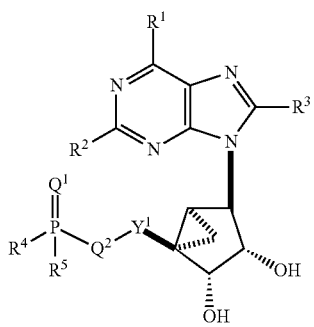

(VII)

wherein
$Q^1$ is O or S;
$Q^2$ is O or S;
$R^1$ is hydrogen, optionally substituted alkyl, optionally substituted cycloalkyl, halogen, or $N(R^6)_2$, wherein each $R^6$ is independently hydrogen, optionally substituted alkyl, or optionally substituted cycloalkyl;
$R^2$ is hydrogen, optionally substituted alkyl, optionally substituted cycloalkyl, optionally substituted alkynyl; $N(R^6)_2$, or halogen;
$R^3$ is hydrogen, optionally substituted alkyl, $N(R^6)_2$, or halogen;
$R^4$ is hydroxyl, optionally substituted alkyl, optionally substituted alkoxy, optionally substituted aryl, optionally substituted —Oaryl, or $N(R^6)_2$;
$R^5$ is hydroxyl, optionally substituted alkyl, optionally substituted alkoxy, optionally substituted aryl, or optionally substituted —Oaryl; or
alternatively, $R^4$ and $R^5$ form a 5- or 6-membered cyclic structure with the phosphorus atom where the cyclic structure contains at least two oxygen atoms and at least 2 or 3 carbon atoms, wherein the carbon atoms are optionally substituted with alkyl or aryl where the chain is attached; and
$Y^1$ is a linking group,
with the proviso that when $Q^1$ and $Q^2$ are both O, and Formula (VII) is not enriched with deuterium, then $R^4$ and $R^5$ are not both hydroxyl,
a deuterium enriched isomer thereof, or a pharmaceutically acceptable salt thereof.

In one aspect, a method of treating a mammalian subject in need of treatment for a cardiac or vascular disease or condition responsive to activation of the cardiac and/or vascular P2X receptor comprises administering to the subject in need thereof an effective amount of a phosphonate or phosphinate N-methanocarba derivative of AMP for the treatment for the cardiac or vascular disease or condition responsive to activation of the cardiac and/or vascular P2X receptor.

In another aspect, a method of improving cardiac contractile performance and/or cardiac function in a mammal in need thereof comprises administering to the mammal in need thereof an effective amount of phosphonate or phosphinate N-methanocarba derivative of AMP for the improvement of cardiac contractile performance and/or cardiac function.

In yet another aspect, a method of treating a mammalian subject in need of treatment for a cardiac hypertrophy, systolic heart failure, diastolic heart failure, ischemic cardiomyopathy, non-ischemic cardiomyopathy, or adverse remodeling and injury following ischemia/reperfusion injury, comprises administering to the mammal in need thereof an effective amount of phosphonate or phosphinate N-methanocarba derivative of AMP.

Figure 1A:
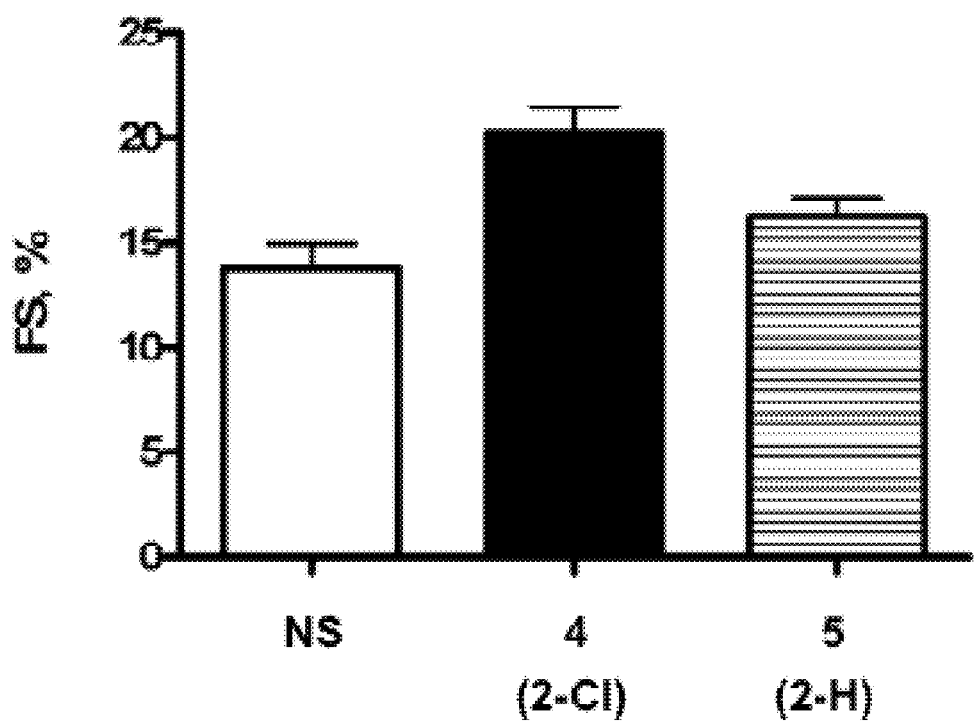
FIG. 1 shows the beneficial effects of 2-Cl substituted phosphonate derivatives of (N)-methanocarba AMP in heart failure mice. Various derivatives of phosphonates were dissolved in sterile normal saline (NS) at 3.3 µM and were infused subcutaneously individually via an Alzet minipump in CSQ mice as described in Methods. After 28 days of infusion, the in vivo heart function was assessed using echocardiography-derived fractional shortening (FS). (A) The 2-Cl substituted 5'-phosphonate derivative 4 was able to improve in vivo cardiac contractile performance in heart failure mice as compared to normal saline-treated heart failure animals (one-way ANOVA with posttest comparison, P<0.05), while the unsubstituted 5 was ineffective (P>0.05). (B) Similarly, 2-Cl substituted higher homologue 9 was able to enhance cardiac contractile function (P<0.05), while the parent unsubstituted compound 10 did not improve the contractile function (P>0.05). Data were mean±SE.

The above-described and other features will be appreciated and understood by those skilled in the art from the following detailed description and appended claims.

DETAILED DESCRIPTION

Cardiac and vascular diseases and conditions responsive to activation of the cardiac P2X receptors include cardiomyopathy and those diseases associated with defects in cardiac contractility. As agonists of P2X receptors, the phosphonate or phosphinate N-methanocarba derivatives of AMP are particularly useful in the treatment of, for example, cardiac hypertrophy, cardiac failure resulting from any cause of abnormal $Ca^{2+}$ homeostasis or from myocardial injuries, vascular insufficiency leading to myocardial infarction, for post-myocardial infarction conditions, for post-myocardial infarction conditions within the short-term post-infarction period, and for diastolic heart failure. Agonists of P2X receptors can be used as cardioprotective agents to increase survival rates in individuals who have had a cardiac event such as a myocardial infarction or to prevent cardiac events in high risk patients. The phosphonate or phosphinate N-methanocarba derivatives of AMP are also useful in the treatment of systolic heart failure of any etiology, ischemic cardiomyopathy, or non-ischemic cardiomyopathy.

Hypertrophy and heart failure, for example, remain a medical condition with "unmet medical need". The available medications have been shown to be beneficial with only modest reduction in mortality rate. The agents disclosed herein are a new class of oral agents that may prolong lifespan in heart failure. They may be more effective than the currently available medications given beneficial result obtained in the animal model.

In one embodiment, the phosphonate or phosphinate N-methanocarba derivative of AMP is a prodrug analog. As used herein, the term prodrug means a compound that is administered in inactive or less active form that is metabolized in vivo to a more active form. Established methods can be used to demonstrate that the phosphonate or phosphinate derivatives and/or their analogs are prodrugs. For example, the prodrug can be injected into mice and the appearance of the parent drug followed by HPLC of serum samples taken at different time points. Because the P2X receptors are ion channels on the cell surface that are stimulated by extracellular ligands, a prodrug approach was selected that should allow for cleavage of the administered compound prior to internalization into a cell, but not in the stomach or gut.

In another example, the regeneration of the parent drug from the prodrug can be followed by spiking blood with a solution containing a suspected prodrug at a concentration of about 20 µM. During incubation the blood mixture can be maintained at 37° C. and samples removed at 5 min, 0.5 hr, 1 hr, 2 hr and 4 hr. After removal the samples are immediately hemolyzed in tubes prefilled with ice chilled water and stored at −20° C. until analysis. For analysis, an internal standard consisting of 100 μl of a 40 μM DMSO solution of the N6-(fluorenylmethyl) derivative of adenosine and 100 μl of a 10% solution of sulfosalicylic acid are added to each sample. After gently vortexing for 5 min, the samples are extracted three times, successively, with 0.5 ml of water-saturated ethyl acetate. Each extraction consists of the addition of ethyl acetate, vortexing for 5 min, centrifugation for 5 min at 2000 g, and manual separation of supernatant with an automatic pipette. The extract fractions are combined and evaporated to dryness under a stream of nitrogen gas. The residue is then reconstituted in 50 μl of an HPLC mobile phase system. 40 μl of this solution is injected for each chromatographic run to provide a kinetic profile for conversion of the prodrug into its parent nucleoside. The chromatography is performed, for example, at room temperature using a reversed-phase column (Zorbax Eclipse 5 μm XDB-C18 analytical column, 250×4.6 mm) equipped with a guard column packed with C-18 material. The flow rate is 1.0 ml/min, and the detection wavelength of 280 nm is used. The time course for relative concentration of each derivative is calculated based on the fractional percentage of total nucleoside detected and was plotted.

The inventors have explored the structure activity relationship (SAR) of phosphonate analogues of compound 3 in a model of cardioprotection.

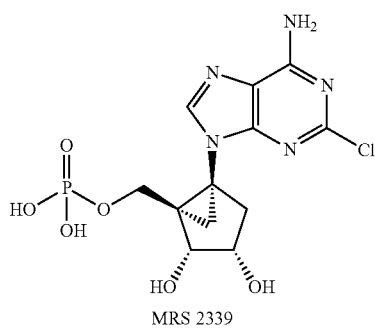

MRS 2339

Although an (N)-methanocarba nucleoside 5'-monophosphate was shown to be a poor substrate of 5'-nucleotidase (CD73), replacement of the phosphoester group of compound 3 with a phosphonate could further increase the in vivo half-life because of the stability of the C—P bond. Phosphonate analogues of nucleotides and other known ligands, in some cases, have been shown to display activity at P2 receptors. In one embodiment, substitution of monophosphate esters with phosphorothioate groups of various ligands has been found to provide resistance to phosphatase-catalyzed hydrolysis without reducing binding affinity. In another embodiment, the introduction of deuterium in place of hydrogen at strategic locations on labile receptor ligands and other drugs has been shown to increase biological lifetime due to an isotope effect without reducing binding affinity.

5'-phosphonate and 5'-methyl phosphonates of (N)-methanocarba adenine 4, 11 or 2-Cl adenine derivatives 5, 12 were synthesized using the previously reported compound 13. At least two synthetic pathways leading to these target molecules can be envisioned viz. routes A and B (Scheme 7A) based on the installation of phosphonate group. Route A involves phosphonate installation at the nucleoside level to generate key intermediate 42, which could be used as common intermediate for the generation of both phosphonates and methyl phosphonates 43 using Michaelis-Arbuzov reaction conditions. While route B involves phosphonate installation at the sugar level on halogenated intermediates 17 and 37 to provide intermediates 18 and 38. Route B does not have a common intermediate, like route A, and, as a result, it involves a longer and more laborious synthetic sequence. Generally, the Michaelis-Arbuzov reaction conditions to generate phosphonate derivatives require long reaction times (24 to 48 hours) at elevated temperatures (120 to 180° C.). Moreover, removal of trialkyl phosphite reagent needs high temperatures and high vacuum. Because of these harsh conditions, a Michaelis-Arbuzov reaction at the nucleoside level generally results in very poor yields (less than 25% yield) of the desired phosphonates along with the formation of a dark-colored thermal degraded products of the nucleosides. On the other hand, Michaelis-Arbuzov reaction at the sugar level generally results in very good yields. Hence, although route B is time consuming and contains more synthetic steps than route A, we have decided to obtain these phosphonate derivatives via route B, believing that it would be reliable with good yields.

Long chain saturated and unsaturated phosphonates of (N)-methanocarba adenine or 2-Cl adenine derivatives 7-10 could be achieved from the same starting compound 13 as for the phosphonates 4, 5, 11 and 12. Similar to the synthesis of phosphonates 4, 5, 11 and 12, these phosphonates could possibly be obtained via two synthetic routes viz, route C and D (Scheme 7B), based on the installation of the phosphonate group. The long chain unsaturated phosphonate could be installed by oxidation and 5'-alcohol of either nucleoside 24 or compound 15 followed by the Wittig-type reaction using tetraisopropyl methylenediphosphonate and NaH to provide phosphonate diester 26 or 30, respectively. One could expect this reaction to proceed smoothly at both nucleoside and sugar stages. Since the route A has a common intermediate 26 for the synthesis of long chain saturated and unsaturated 5'-phosphonates 7-10, we have decided to explore the synthesis of these phosphonates by the shorter synthetic route C.

There is increasing evidence that chronic activation of the native cardiac P2X receptor by nucleotide analogues protects against the progression of heart failure. The $P2X_4$ receptor is an essential subunit of this native receptor, but we do not know what other P2X subtypes are present. The cardiac myocyte receptor is not identical to the vascular $P2X_4$ receptor, which has a key role in the response of endothelial cells to changes in blood flow.

The synthetic nucleotide analogue 3 activates the native cardiac P2X receptor, as indicated in electrophysiological experiments with normal cardiac myocytes and those that overexpress CSQ and based on its in vivo ability to improve the heart failure phenotype of these animals. The rigid carbocyclic ring system contained in this derivative stabilizes nucleotides toward the action of nucleotidases. Therefore, compound 3 is expected to be more stable than the corresponding riboside. In the present study, we have synthesized fully hydrolysis-resistant adenosine monophosphate derivatives based on phosphonate linkages. The C—O—P bond of compound 3 was found to be stable over 24 hours in aqueous medium at pH 1.5 to simulate the acidity of the stomach, however incubation at 37° C. in the presence of mammalian cell membranes (1321N1 astrocytoma cells) resulted in considerable hydrolysis of the 5'-phosphate of 3 (data shown). Therefore, a more stable structural alternate to the 5'-phosphate linkage was sought.

An in vivo screen of cardiac function was used to test the novel analogues. Thus, the results of this chronic study likely reflect both pharmacodynamic and pharmacokinetic factors. Several of the novel phosphonate analogues displayed the same agonist activity as compound 3 at native cardiac P2X receptors, i.e. they protected the heart muscle when chronically administered in the CSQ model. The SAR analysis showed that considerable cadioprotection was associated with specific structural features of the phosphonate derivatives. The variation in the chain length and saturation at the 5' carbon provided consistent results in the in vivo screen. Two of the phosphonates, 4 and 9, both saturated homologues containing a 2-Cl substitution, improved FS, while the unsaturated phosphonates and 2-H analogues were inactive. The most favorable FS (20.25%, compared to 13.78% in controls) was observed for (1'S,2'R,3'S,4'R,5'S)-4'-(6-amino-2-chloropurin-9-yl)-2',3'-(dihydroxy)-1'-(phosphonomethylene)-bicyclo[3.1.0]hexane 4, which is the equivalent of compound 3 in which the 5'-O has been excised. The higher homologue 9 displayed a FS of 19.26%. Thus, it is possible to extend the SAR around compound 3, for chronic activation of the cardiac P2X receptor leading to a beneficial effect in heart failure.

Further, the 5'-phosphate 3 and the prodrug 9a (MRS2944) are stable to acidic conditions representative of stomach acid (pH 1.5). However, incubation of 5'-phosphate 3 or the diester phosphonate 9a at 37° C. in the presence of mammalian cell membranes (1321N1 astrocytoma cells) resulted in considerable hydrolysis (data shown). This indicates that the desirable cleavage of a diester phosphonate prodrug such as 9a is feasible in the presence of tissue, while the phosphate drugs such as 3 might be subject to premature cleavage in vivo. Without being held to theory, it is believed that the prodrug approach will allow the masked drug to pass through the stomach to be absorbed intact in the intestines, and for the charged phosphoryl group to remain intact until the free drug reaches the site of action in the heart. Therefore, the stable phosphonates would be suitable in this scheme. The cleavage of the prodrug derivatives is to occur in circulation prior to reaching the tissue site of action, because intracellular internalization would be undesirable. Therefore, many of the prodrug schemes that aim for penetration of the masked drug into the cells, i.e. for antiviral or anticancer application of nucleotide derivatives, would likely not be suitable here.

It is not feasible to study the analogues at a recombinant homotrimeric P2X$_4$ receptor system, because the endogenous cardiac P2X receptor is thought to be composed of P2X$_4$ receptor subunits in heteromeric association with a yet unidentified P2X subtype. The P2X$_4$ receptor is known to associate with other P2X receptor subtypes, and these heterotrimers are pharmacologically distinct from P2X$_4$ homotrimers.

Another site of action of adenine nucleotides in cardiac tissue is the metabotropic P2Y$_1$ receptor, which causes a nitric oxide-dependent relaxation of the vascular smooth muscle. Therefore, we tested the nucleotides as P2Y$_1$ receptor agonists to account for the possibility that the observed cadiovascular effects of the phosphonate derivatives were a result of activation of an endothelial P2Y$_1$ receptor. Compound 3 was initially characterized in assays of PLC as a weak hP2Y$_1$ receptor agonist (EC$_{50}$ 1.89 μM), and that conclusion is consistent with the potency observed here in inducing calcium transients in the same cell line. All of the phosphonate derivatives tested were inactive at the P2Y$_1$ receptor. This suggests the use of these compounds as more selective pharmacological probes of the endogenous cardiac P2X receptor than compound 3. However, it is worth noting that the cardioprotection provided by compound 3 was shown to be independent of the P2Y$_1$ receptor by its inability to dilate aortic rings and by use of a P2Y$_1$-selective antagonist MRS2500. This antagonist could not block the membrane current evoked by 3 under voltage clamp in mouse cardiac myocytes.

Disclosed herein are novel phosphonate or phosphinate N-methanocarba derivatives of AMP. Suitable N-methanocarba derivatives of AMP are given in Formula (I) below:

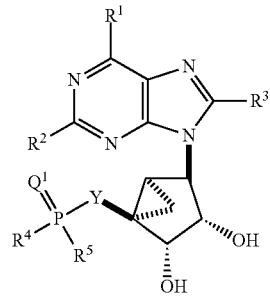

(I)

wherein
Q$^1$ is O or S;
R$^1$ is hydrogen, optionally substituted alkyl, optionally substituted cycloalkyl, halogen, or N(R$^6$)$_2$, wherein each R$^6$ is independently hydrogen, optionally substituted alkyl, or optionally substituted cycloalkyl;
R$^2$ is hydrogen, optionally substituted alkyl, optionally substituted cycloalkyl, optionally substituted alkynyl, N(R$^6$)$_2$, or halogen;
R$^3$ is hydrogen, optionally substituted alkyl, N(R$^6$)$_2$, or halogen;
R$^4$ is hydroxyl, optionally substituted alkyl, optionally substituted alkoxy, optionally substituted aryl, optionally substituted —Oaryl, or N(R$^6$)$_2$;
R$^5$ is hydroxyl, optionally substituted alkyl, optionally substituted alkoxy, optionally substituted aryl, or optionally substituted —Oaryl; or
  alternatively, R$^4$ and R$^5$ form a 5- or 6-membered cyclic structure with the phosphorus atom where the cyclic structure contains at least two oxygen atoms and at least 2 or 3 carbon atoms, wherein the carbon atoms are optionally substituted with alkyl or aryl where the chain is attached; and
Y is a linking group linked to the phosphorus atom by a carbon atom, a deuterium enriched isomer thereof, or a pharmaceutically acceptable salt thereof.

The Y linking group is optionally substituted C$_1$-C$_6$ alkylene, optionally substituted C$_1$-C$_6$ alkenylene, optionally substituted C$_1$-C$_6$ alkynylene, or optionally substituted —C$_1$-C$_6$ alkylene-O—C$_1$-C$_6$ alkylene-. In one embodiment, Y is —CH$_2$—. In another embodiment, Y is —CH$_2$CH$_2$—. In yet another embodiment, Y is —CH═CH—.

In one embodiment, R$^4$ is hydroxyl, methyl, or C$_1$-C$_6$ alkoxy, and R$^5$ is hydroxyl, methyl, or C$_1$-C$_6$ alkoxy.

In one embodiment, R$^4$ and R$^5$ are linked together by a 3 carbon chain substituted with an aryl group at the 1 position (e.g., 1-aryl-1,3-propanyl cyclic ester group).

In one embodiment, R$^1$ is NH$_2$.
In another embodiment, R$^3$ is hydrogen.
In yet another embodiment, R$^2$ is hydrogen chloro, iodo, or C$_1$-C$_2$ alkynyl.

In one embodiment where the N-methanocarba derivative of AMP is according to Formula (I), Y is —CH$_2$— or —CH$_2$CH$_2$—, R$^1$ is NH$_2$, R$^2$ is halogen, R$^3$ is hydrogen, R$^4$ is alkoxy or —Oaryl, and R$^5$ is hydroxyl.

In another embodiment where the N-methanocarba derivative of AMP is according to Formula (I), Y is —CH$_2$— or —CH$_2$CH$_2$—, R$^1$ is NH$_2$, R$^2$ is halogen, R$^3$ is hydrogen, and R$^4$ and R$^5$ are both alkoxy or —Oaryl.

In yet another embodiment where the N-methanocarba derivative of AMP is according to Formula (I), Y is —CH$_2$— or —CH$_2$CH$_2$—, R$^1$ is NH$_2$, R$^2$ is halogen, R$^3$ is hydrogen, and R$^4$ and R$^5$ form a six membered cyclic structure —OCH(R)CH$_2$CH$_2$O— where R is hydrogen or aryl.

In yet another embodiment where the N-methanocarba derivative of AMP is according to Formula (I), the derivative is a triethylamine salt where Y is —CH$_2$—, R$^1$ is NH$_2$, R$^2$ is iodo, R$^3$ is hydrogen, R$^4$ hydroxyl and R$^5$ hydroxyl.

In still another embodiment where the N-methanocarba derivative of AMP is according to Formula (I), Q$^1$ is O; R$^1$ is N(R$^6$)$_2$ wherein each R$^6$ is hydrogen; R$^2$ is halogen; R$^3$ is hydrogen; R$^4$ is hydroxyl or optionally substituted alkoxy; R$^5$ is hydroxyl or optionally substituted alkoxy; and Y is a linking group linked to the phosphorus atom by a carbon atom.

In another embodiment where the N-methanocarba derivative of AMP is according to Formula (I), Q$^1$ is O; R$^1$ is N(R$^6$)$_2$ wherein each R$^6$ is hydrogen; R$^2$ is halogen; R$^3$ is hydrogen; R$^4$ is hydroxyl or optionally substituted alkoxy; R$^5$ is hydroxyl or optionally substituted alkoxy; and Y is a C$_1$-C$_6$ alkylene.

Other suitable N-methanocarba derivatives of AMP are given in Formula (II) below:

Still other suitable N-methanocarba derivatives of AMP are given in Formula (III) below:

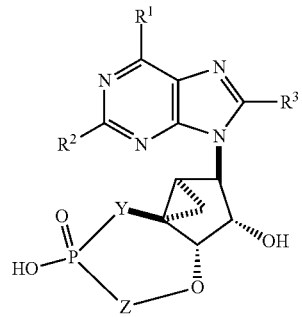

(III)

wherein R$^1$, R$^2$, R$^3$, and Y are as previously defined; and Z is a bond or —O—C(=O)—where the carbonyl carbon is bonded to the oxygen of the bicycle group and the oxygen is bonded to the phosphorus atom, a deuterium enriched isomer thereof, or a pharmaceutically acceptable salt thereof.

In one embodiment where the N-methanocarba derivatives of AMP is according to Formula (III), Y is —CH$_2$— or —CH$_2$CH$_2$—, R$^1$ is NH$_2$, R$^2$ is halogen, R$^3$ is hydrogen, and Z is a bond or —O—C(=O)—.

Other suitable N-methanocarba derivatives of AMP are given in Formula (IV) below:

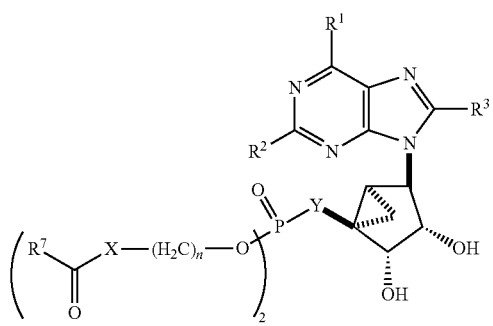

(II)

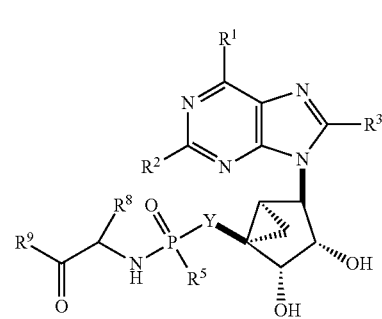

(IV)

wherein R$^1$, R$^2$, R$^3$, and Y are as previously defined; X is O or S; n is 1, 2, or 3; and R$^7$ is optionally substituted alkyl or optionally substituted aryl, a deuterium enriched isomer thereof, or a pharmaceutically acceptable salt thereof.

In one embodiment where the N-methanocarba derivatives of AMP is according to Formula (II), Y is —CH$_2$— or —CH$_2$CH$_2$—, R$^1$ is NH$_2$, R$^2$ is halogen, R$^3$ is hydrogen, n is 1, X is O, and R$^7$ is alkyl or aryl.

In another embodiment where the N-methanocarba derivatives of AMP is according to Formula (II), Y is —CH$_2$— or —CH$_2$CH$_2$—, R$^1$ is NH$_2$, R$^2$ is halogen, R$^3$ is hydrogen, n is 2, X is S, and R$^7$ is methyl.

wherein R$^1$, R$^2$, R$^3$, R$^5$, and Y are as previously defined; R$^8$ is hydrogen or optionally substituted alkyl; and R$^8$ is optionally substituted alkyl, optionally substituted alkoxy, or optionally substituted aryl, a deuterium enriched isomer thereof, or a pharmaceutically acceptable salt thereof.

In one embodiment where the N-methanocarba derivatives of AMP is according to Formula (IV), Y is —CH$_2$— or —CH$_2$CH$_2$—, R$^1$ is NH$_2$, R$^2$ is halogen, R$^3$ is hydrogen, R$^5$ is hydroxyl, R$^8$ is methyl, and R$^9$ is methoxy.

In another embodiment where the N-methanocarba derivatives of AMP is according to Formula (IV), Y is —CH$_2$— or —CH$_2$CH$_2$—, R$^1$ is NH$_2$, R$^2$ is halogen, R$^3$ is hydrogen, R$^5$ is —O-phenyl, R$^8$ is methyl, and R$^9$ is methoxy.

Other suitable N-methanocarba derivatives of AMP are given in Formula (V) below:

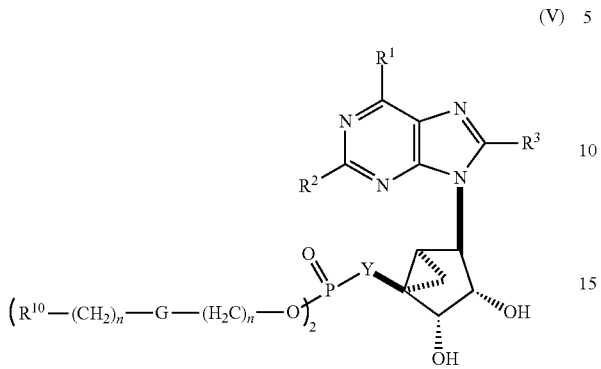

wherein $R^1$, $R^2$, $R^3$, n, and Y are as previously defined; G is O or S—S; and $R^{10}$ is hydrogen, hydroxyl, optionally substituted alkyl, optionally substituted alkoxy, or optionally substituted aryl, a deuterium enriched isomer thereof, or a pharmaceutically acceptable salt thereof.

In one embodiment where the N-methanocarba derivatives of AMP is according to Formula (V), Y is —$CH_2$— or —$CH_2CH_2$—, $R^1$ is $NH_2$, $R^2$ is halogen, $R^3$ is hydrogen, n is 2, G is S—S, and $R^{10}$ is hydroxyl.

Still other suitable N-methanocarba derivatives of AMP are given in Formula (VI) below:

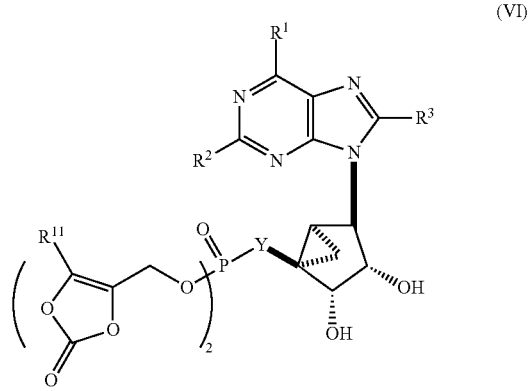

wherein $R^1$, $R^2$, $R^3$, and Y are as previously defined; and $R^{11}$ is hydrogen, optionally substituted alkyl, or optionally substituted aryl. In one embodiment where the N-methanocarba derivatives of AMP is according to Formula (VI), Y is —$CH_2$— or —$CH_2CH_2$—, $R^1$ is $NH_2$, $R^2$ is halogen, $R^3$ is hydrogen, and $R^{11}$ is alkyl, or aryl, a deuterium enriched isomer thereof, or a pharmaceutically acceptable salt thereof.

Still other suitable N-methanocarba derivatives of AMP are given in Formula (VII) below:

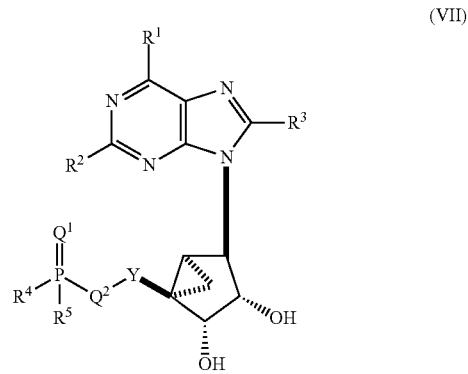

wherein
$Q^1$ is O or S;
$Q^2$ is O or S;
$R^1$, $R^2$, $R^3$, $R^4$, and $R^5$ are as previously defined above; with the proviso that when $Q^1$ and $Q^2$ are both O, and Formula (VII) is not enriched with deuterium, then $R^4$ and $R^5$ are not both hydroxyl; and $Y^1$ is a linking group, a deuterium enriched isomer thereof, or a pharmaceutically acceptable salt thereof.

The $Y^1$ linking group is optionally substituted $C_1$-$C_6$ alkylene, optionally substituted $C_1$-$C_6$ alkenylene, optionally substituted $C_1$-$C_6$ alkynylene, or optionally substituted —$C_1$-$C_6$ alkylene-O—$C_1$-$C_6$ alkylene-. In one embodiment, $Y^1$ is —$CH_2$—. In another embodiment, $Y^1$ is —$CH_2CH_2$—. In yet another embodiment, $Y^1$ is —CH=CH—.

In another embodiment where the N-methanocarba derivative of AMP is according to Formula (VII), $Q^1$ is O; $Q^2$ is S; $R^1$ is $N(R^6)_2$ wherein each $R^6$ is hydrogen; $R^2$ is halogen; $R^3$ is hydrogen; $R^4$ is hydroxyl or optionally substituted alkoxy; $R^5$ is hydroxyl or optionally substituted alkoxy; and $Y^1$ is a $C_1$-$C_6$ alkylene.

In another embodiment where the N-methanocarba derivative of AMP is according to Formula (VII), $Q^1$ is S; $Q^2$ is O; $R^1$ is $N(R^6)_2$ wherein each $R^6$ is hydrogen; $R^2$ is halogen; $R^3$ is hydrogen; $R^4$ is hydroxyl or optionally substituted alkoxy; $R^5$ is hydroxyl or optionally substituted alkoxy; and $Y^1$ is a $C_1$-$C_6$ alkylene.

Specific embodiments of phosphonate or phosphinate N-methanocarba derivatives of AMP include:

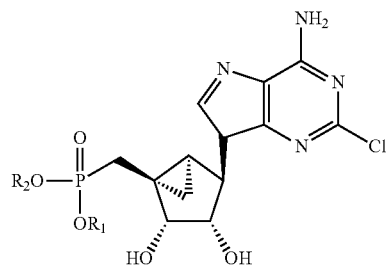

Alkyl or aryl ester prodrugs
$R_1$ = $R_2$ = any alkyl or aryl groups
$R_1$ = any alkyl or aryl group; $R_2$ = H -continued

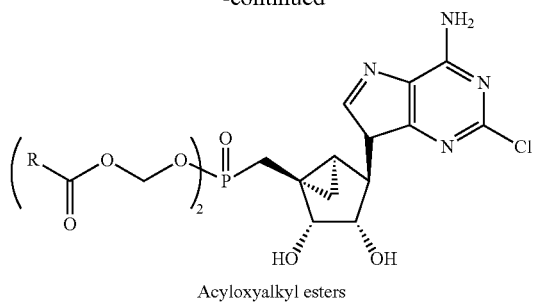

Acyloxyalkyl esters

R = any alkyl or aryl groups

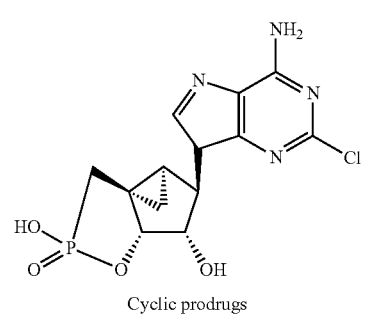

Cyclic prodrugs

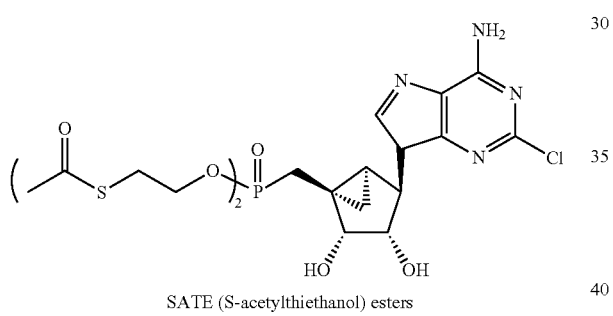

SATE (S-acetylthiethanol) esters

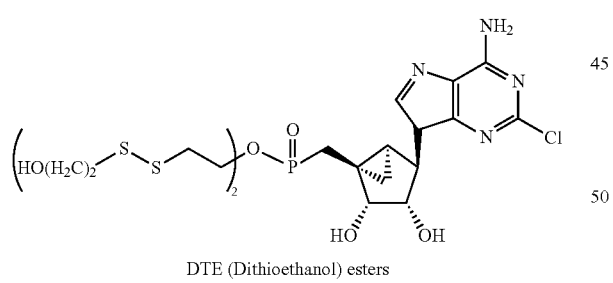

DTE (Dithioethanol) esters

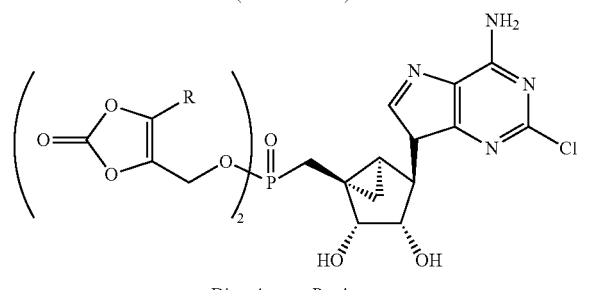

Dioxolenone Prodrugs

R = alkyl or aryl

-continued

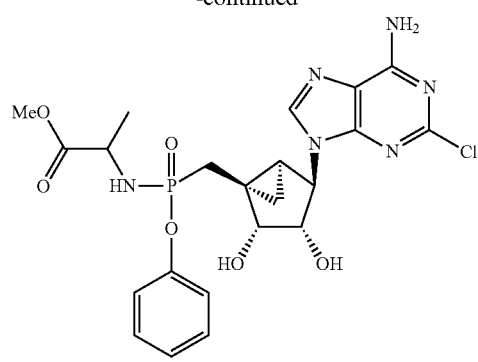

Aryl phosphoramidates

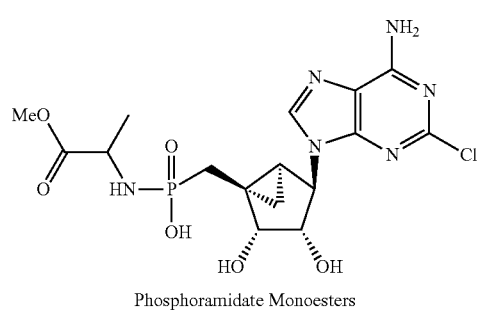

Phosphoramidate Monoesters

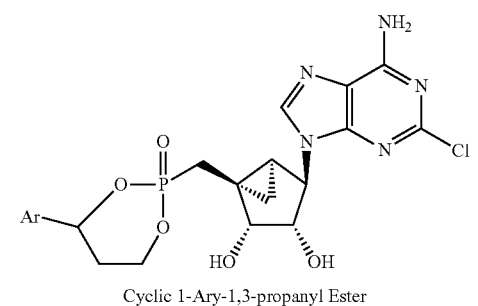

Cyclic 1-Ary-1,3-propanyl Ester

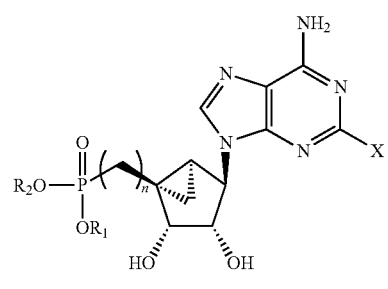

Alkyl or aryl ester prodrugs[1-3]

n = 1 or 2; X = any halogen $R_1$ = $R_2$ = any alkyl or aryl groups $R_1$ = any alkyl or aryl group; $R_2$ = H 17
-continued

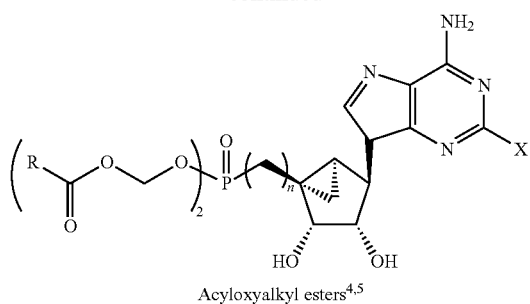

Acyloxyalkyl esters[4,5]

n = 1 or 2; X = any halogen

R = any alkyl or aryl groups

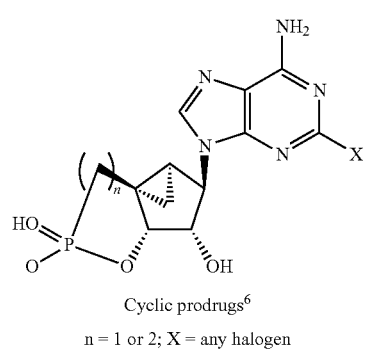

Cyclic prodrugs[6]

n = 1 or 2; X = any halogen

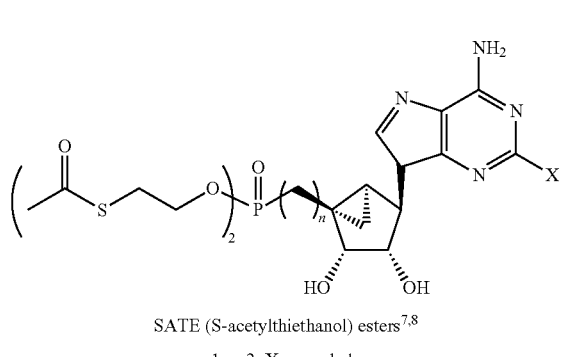

SATE (S-acetylthiethanol) esters[7,8]

n = 1 or 2; X = any halogen

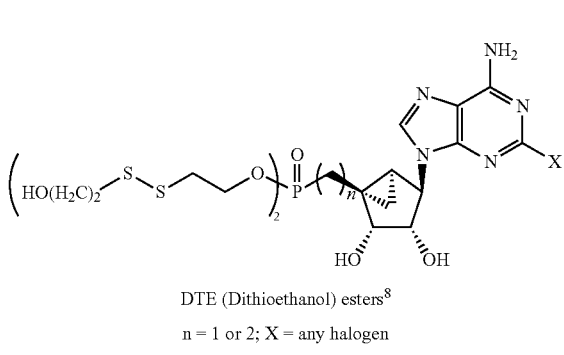

DTE (Dithioethanol) esters[8]

n = 1 or 2; X = any halogen

18
-continued

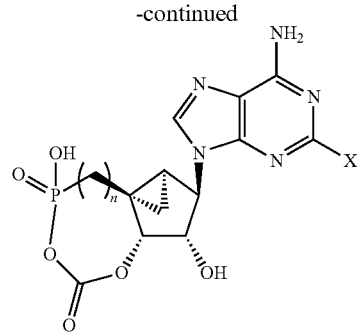

Cyclic prodrugs n = 1 or 2; X = halogen

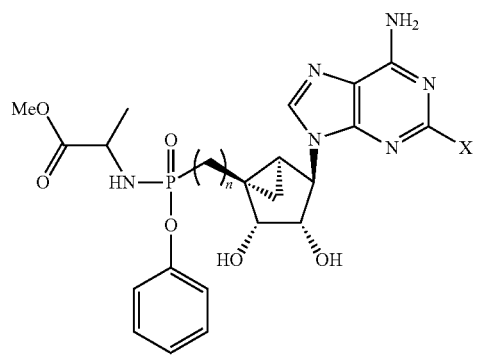

Dioxolenone Prodrugs[9]

n = 1 or 2; X = any halogen

R = alkyl or aryl

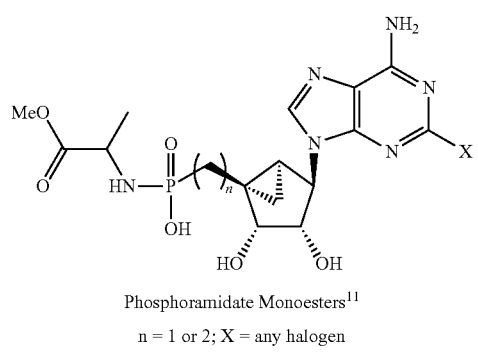

Aryl phosphoramidates[10]

n = 1 or 2; X = any halogen

Phosphoramidate Monoesters[11]

n = 1 or 2; X = any halogen

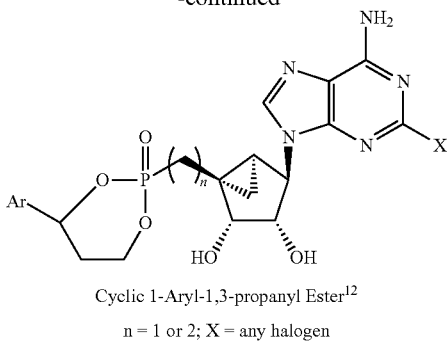

Cyclic 1-Aryl-1,3-propanyl Ester[12]

n = 1 or 2; X = any halogen

Without being held to theory, it is believed that the spacing of the phosphorus relative to the methanocarba ring is important for in vivo activity. Among the phosphonate derivatives tested, only the longer spacer of 2 carbons in 11a resulted in effective cardioprotection by prodrug ester derivatives, even though the precursors or unblocked nucleotides, i.e. 4 and its higher homologue 9, were active in both cases. Thus, both the masked diester 11a and its charged precursor 9 were clearly protective in vivo. This suggested that enzymatic unblocking of the esters in vivo depended on unhindered steric access to the phosphonyl group.

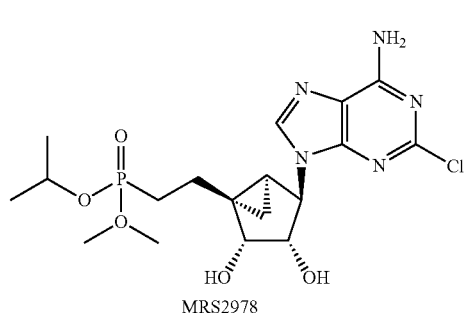

MRS2978

The phosphonate or phosphinate N-methanocarba derivatives of AMP have an affinity for P2X receptors, including cardiac and vascular P2X receptors. The P2X receptor affinity can be determined by the dose-response of increases in contractility for the different compounds. Changes in contractility can be measured as changes in sarcomere length and $Ca^{2+}$ transients recorded from single isolated myocytes using an epi-fluorescence inverted microscope.

In one embodiment, phosphonate or phosphinate N-methanocarba derivatives of AMP are useful in the treatment of cardiac diseases responsive to activation of the cardiac P2X receptor such as, for example, cardiac hypertrophy and/or cardiac failure resulting from abnormal $Ca^{2+}$ homeostasis.

In one embodiment, the compounds disclosed herein are used in the treatment of cardiac diseases responsive to activation of the cardiac P2X receptor such as cardiomyopathy. Cardiac diseases responsive to activation of cardiac P2X receptors include, for example, cardiac hypertrophy and/or cardiac failure resulting from abnormal $Ca^{2+}$ homeostasis. Cardiac hypertrophy is a thickening of the heart muscle (myocardium), which results in a decrease in size of the chamber of the heart, including the left and right ventricles. Alterations in $Ca^{2+}$ handling are known to be associated with cardiac hypertrophy. Cardiac failure is the failure of the heart to maintain a cardiac output sufficient to meet the metabolic demands of the body. Cardiac failure can result from any structural or functional cardiac disorder that impairs the ability of the heart to fill with or pump a sufficient amount of blood throughout the body. The compounds disclosed herein are particularly useful in the treatment if cardiac failure resulting from abnormal $Ca^{2+}$ homeostasis.

The compounds disclosed herein are particularly useful in the treatment of cardiac diseases responsive to activation of the cardiac P2X receptor associated with defects in cardiac contractility. Such diseases include myocardial infarction. As used herein, myocardial infarction, commonly known as a heart attack, is a disease state that occurs when the blood supply to a part of the heart is interrupted. The resulting ischemia or oxygen shortage causes damage and potential death of heart tissue. In one embodiment, treatment is done within the within the short-term post-infarction period. As used herein, the short term post-infarction period is within 48 hours of myocardial infarction. The advantage of treating in the short term post infarction period is to block the stimulus for cardiac hypertrophy and adverse remodeling at an early stage of the heart failure progression after myocardial infarction.

In a related embodiment, the compounds have affinity for vascular P2X receptors and can be used to treat conditions associated with vascular P2X receptors. Without being held to theory, it is believed that vascular P2X receptors produce nitric oxide, which can diffuse to myocytes and improve the function of the myocytes. Thus, by binding vascular P2X receptors such as endothelial receptors, the phosphonate or phosphinate N-methanocarba derivatives of AMP can be used to treat conditions responsive to an increase in nitric oxide.

Additionally, the compounds disclosed herein are useful for enhancing cardiac function by increasing cardiac muscle contractility and/or increasing diastolic cardiac muscle relaxation. Included herein are thus methods of improving cardiac contractile performance in a mammal in need thereof comprising administering a therapeutically effective amount of a phosphonate or phosphinate N-methanocarba derivative of AMP. In one embodiment, the mammal has had or is suspected of having a myocardial infarction. In another embodiment, administering is performed within the short-term post-infarction period.

The compounds disclosed herein are also useful for improving cardiac function by administering to a mammal in need of such treatment. As used herein, improving cardiac function can include, for example, improving the ability of the heart to relax, providing favorable remodeling in a subject with heart failure, decreasing fibrosis, decreasing the hypertrophy of cardiac myocytes, and/or improving calcium handling in myocytes in a heart failure subject.

The compounds disclosed herein can be used to treat systolic or diastolic heart failure. 'Systole' occurs when the heart contracts and 'diastole' is the relaxation phase of the heart. The increase in −dP/dt or rate of relaxation of the heart muscle in transgenic animals overexpressing the $P2X_4$ receptor suggests that activation of the cardiac P2X receptor can be used to treat diastolic heart failure. Like $P2X_4$ receptor overexpression, treatment with the N-methanocarba derivatives of AMP may be employed for individuals in need of treatment for diastolic heart failure. Diastolic heart failure is caused when the heart does not fully relax, so it does not fill properly with blood. By increasing the rate of relaxation of the heart muscle, the N-methanocarba derivatives of AMP will improve cardiac function in individuals with diastolic heart failure. Systolic heart failure is sometimes referred to as left ventricular failure, and results from a defect or abnormality in the systolic, that is contraction, function during the expulsion of blood to the rest of the body. As a result, the amount of blood pumped to the body and to the lungs is reduced, and the ventricle, usually enlarges.

In another embodiment, the compounds disclosed herein are used to treat adverse remodeling and injury following ischemia/reperfusion injury. In one embodiment, the P2X receptor agonists are used to treat individuals in need of treatment for ischemia and reperfusion injury. Ischemia is a deficiency of oxygen in a part of the body causing metabolic changes, usually temporary, which can be due to a constriction or an obstruction in the blood vessel supplying that part. Reperfusion is the restoration of blood flow to an organ or tissue. Ischemia and reperfusion of the heart muscle can cause significant injury with deleterious consequences. Effective therapies that reduce such injury will have significant benefits in treatment of myocardial infarction and reperfusion injury.

The phosphonate or phosphinate N-methanocarba derivatives of AMP are used to treat a mammal such as a human being.

In one embodiment, the phosphonate or phosphinate N-methanocarba derivative of AMP is co-administered with an additional agent such as, for example, a beta-adrenergic receptor blocker, an angiotensin receptor blocker or an angiotensin converting enzyme inhibitor or an aldosterone receptor blocker.

In one embodiment, included herein is a composition comprising a phosphonate or phosphinate N-methanocarba derivative of AMP and a pharmaceutically acceptable excipient.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art.

Preparations for oral administration can be suitably formulated to give controlled release of the active compound.

For buccal administration, the compositions can take the form of tablets or lozenges formulated in conventional manner.

For administration by inhalation, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion via either intravenous, intraperitoneal or subcutaneous injection. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compositions can be formulated into creams, lotions, ointments or tinctures, e.g., containing conventional bases, such as hydrocarbons, petrolatum, lanolin, waxes, glycerin, or alcohol. The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (e.g., subcutaneously or intramuscularly) or by intramuscular injection. Thus, for example, the compositions can be formulated with suitable polymeric or hydrophobic materials (e.g., as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions can, if desired, be presented in a pack or dispenser device, which can contain one or more unit dosage forms containing the active ingredient. The pack can for example comprise metal or plastic foil, such as a blister pack. The pack or dispenser device can be accompanied by instructions for administration.

The amount of phosphonate or phosphinate N-methanocarba derivative of AMP that may be combined with pharmaceutically acceptable excipients to produce a single dosage form will vary depending upon the host treated and the particular mode of administration. The specific therapeutically effective amount for a particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. The concentrations of the compounds described herein found in therapeutic compositions will vary depending upon a number of factors, including the dosage of the drug to be administered, the chemical characteristics (e.g., hydrophobicity) of the compounds employed, and the route of administration. In general terms, the phosphonate or phosphinate N-methanocarba derivatives of AMP may be provided in an aqueous physiological buffer solution (for example, 1 cc) containing about 0.2% w/v compound for oral administration. Typical dose ranges are about 285 µg/kg of body weight per day in three divided doses; a preferred dose range is from about 42 µg/kg to about 171 µg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors. For example, if the compound is metabolized in the liver or excreted in bile, some of the active compound absorbed from the gastrointestinal tract will be inactivated by the liver before it can reach the general circulation and be distributed to its sites of action. It is not believed that the phosphonate or phosphinate N-methanocarba derivatives of AMP will be subject to this first-pass loss. Additionally, because these compounds are polar and water soluble, it is expected that they will have a small volume of distribution, and thus be readily eliminated by the kidney. Moreover, binding of the instant compounds to plasma proteins may limit their free concentrations in tissues and at their locus of action since it is only the unbound drug which equilibriums across the membrane receptor sites. It is anticipated that the phosphate moiety of the instant compounds may facilitate binding of the compounds to plasma albumins, which will in turn influence the amount of free compound available to activate muscle cell P2 purinergic receptors. However, it is expected that such binding to plasma protein will not generally limit renal tubular secretion of biotransformation since these processes lower the free drug concentration and this is rapidly followed by the association of this drug-protein complex. Another factor affecting bioavailability is the distribution of the compounds to tissues. Given the relatively small size of the compounds and their water solubility, it is anticipated that the compounds will have a relatively fast second phase of drug distribution. This distribution is determined by both the blood flow to the particular tissue of the organ, such as the heart, as well as the rate at which the compounds diffuse into the interstitial compartment from the general circulation through the highly permeable capillary endothelium (except in the brain). Due to the relative hydrophilicity of these compounds, it is anticipated that there will be no fat or other significant tissue reservoir of the compounds, which would account for a third phase of distribution-accumulation.

The invention is further illustrated by the following non-limiting examples.

EXAMPLES

Example 1

Chemical Synthesis

The phosphonate derivatives on varied carbon skeletons (Table 1) were synthesized by the methods shown in Schemes 1-6. In some cases, the phosphorous atom was bonded directly to the 5' carbon atom (Schemes 1, 2), while in other cases, a carbon atom was added at that position to form either a saturated or unsaturated nucleotide analogue (Schemes 3-5). Alternately, a methylphosphonate group was included in compounds 11 and 12, which were otherwise equivalent to 4 and 5, respectively (Scheme 6). The 2 position contained either hydrogen (in compounds 5, 8, 10, 12) or Cl (as in the known active compound 3 and the novel analogues 4, 7, 9, 11). The reference compound 3 was synthesized by a modification of the reported method, which lead to improved yields.

Known alcohol 13 was protected as a O-tert-butyldimethylsilyl ether using TBDPS-Cl, imidazole and DMAP to get compound 14, followed by the reduction of the ethyl ester using DIBAL-H in anhydrous THF resulting in compound 15 in very good yield (Scheme 1). In order to introduce an iodo group at the 5' position, a classical two step procedure was implemented. This involved the initial activation of the 5'-alcohol as a mesylate followed by an $S_N2$ nucleophilic attack of iodide on the activated 5'-position resulting in the 5'-iodo compound 17 in 95% yield. The iodo compound 17 was subjected to classical Michaelis-Arbuzov reaction conditions with excess triethylphosphite and heating up to 110° C. for 17 h to provide a phosphonate diester 18 in excellent 94% yield (Scheme 1). Desilylation using TBAF resulted in alcohol 19, which was a suitable substrate for Mitsunobu base coupling reactions.

The alcohol 19 was used as a common key intermediate to synthesize phosphonates 4 and 5 (Scheme 2). Synthetic procedures for phosphonates 4 and 5 involved initial Mitsunobu base coupling reaction using triphenylphosphine, diisopropyl azodicarboxylate, and the corresponding purine base followed by amination at the 6 position of the purine ring using 2M $NH_3$ in isopropanol (Scheme 2). Finally, the simultaneous deprotection of both the phosphonate diester and the acetonide of 21 and 23 was achieved upon treatment with freshly opened iodotrimethylsilane to get target phosphonates 4 and 5, respectively (Scheme 2). Efforts to use alternative relatively milder reagents, bromotrimethylsilane and Dowex-50 ion exchange resin, resulted in partial deprotection (results not shown).

The synthetic routes to the elongated saturated and unsaturated phosphonate derivatives 7-10 are shown in Schemes 3-5. The saturated phosphonate 10 was synthesized by oxidation of known alcohol 24 to the 5'-aldehyde 25 in 80% yield. It is noteworthy that not even a small amount of decomposition of the aldehyde was observed after storage at room temperature (rt) for several days. The α,β-unsaturated alkyl phosphonate ester 26 was prepared from aldehyde 25 in a Wittig-type reaction using tetraisopropyl methylenediphosphonate and sodium hydride in anhydrous THF. The E-configuration of the resulting alkene could be inferred from the large coupling constant ($^3J$=17.1 Hz). Amination followed by hydrolysis of phosphonate diester and acetonide resulted in α,β-unsaturated alkyl phosphonate 27 (Scheme 3).

Catalytic hydrogenation of 27 in the presence of $H_2$ (3 bar), palladium on carbon and MeOH:2M aq. NaOH (1:1, v/v) resulted in the expected olefin reduction and dechlorination to give the corresponding saturated phosphonate diester 28. Compound 28 was converted to the long chain saturated alkyl phosphonate 10 using the previously described iodotrimethylsilane deprotection reaction conditions. To our surprise, our various efforts to synthesize 36 (Scheme 5) from 27 by olefin reduction, running the reaction at atmospheric pressure and using less weight percent of catalyst, either resulted in an incomplete reaction or generated an inseparable mixture of dehalogenated and halogenated products (results not shown).

Hence, in order to synthesize phosphonates 8 and 9, we decided to install the phosphonate diester before the Mitsunobu base coupling reaction, as described in Schemes 4 and 5. The 5'-alcohol of compound 15 was oxidized using Dess-Martin periodinane reaction to get aldehyde 29. Similar to the aldehyde 25, aldehyde 29 also displayed considerable stability at rt. The α,β-unsaturated alkyl phosphonate diester 30 was obtained using the previously described Wittig-type reaction conditions. Desilylation under standard conditions resulted in the formation of alcohol 31, which served as the key intermediate for the synthesis of long chain unsaturated and saturated alkyl phosphonates 8 and 9, respectively.

A Mitsunobu base coupling reaction on compound 31 using triphenylphosphine, 6-chloropurine, and diisopropyl azodicarboxylate followed by amination and hydrolysis of the phosphonate diester and acetonide resulted in formation of long chain α,β-unsaturated alkyl phosphonate 8. Sequential catalytic hydrogenation of the resulting vinyl phosphonate diester 31 in the presence of palladium on carbon, a Mitsunobu base coupling reaction, and amination provided the long chain saturated phosphonate diester 36. Simultaneous deprotection of the phosphonate diester and the acetonide using iodotrimethylsilane resulted in the desired phosphonate 9 along with the formation of corresponding dehalogenated product to yield phosphonate 10.

The synthetic approach to methylphosphonates 11 and 12 is shown in Scheme 6. It involved initial 5'-bromination using $CBr_4$ and treatment with triphenylphosphine and triethylamine to result in 5'-bromosugar 37 in 81% yield. A subsequent Michaelis-Arbuzov reaction using diethyl methylphosphite, followed by desilylation with TBAF gave the 5'-methylphosphonate monoester 38 with 1-alcohol 39 as an inseparable mixture of diastereomers. A further Mitsunobu base coupling reaction with 2,6-dichloropurine, followed by amination and final deprotection gave the desired methylphosphonate 11 along with corresponding dehalogenated methylphosphonate 12.

Example 3

Biological Evaluation

Figure 1B:
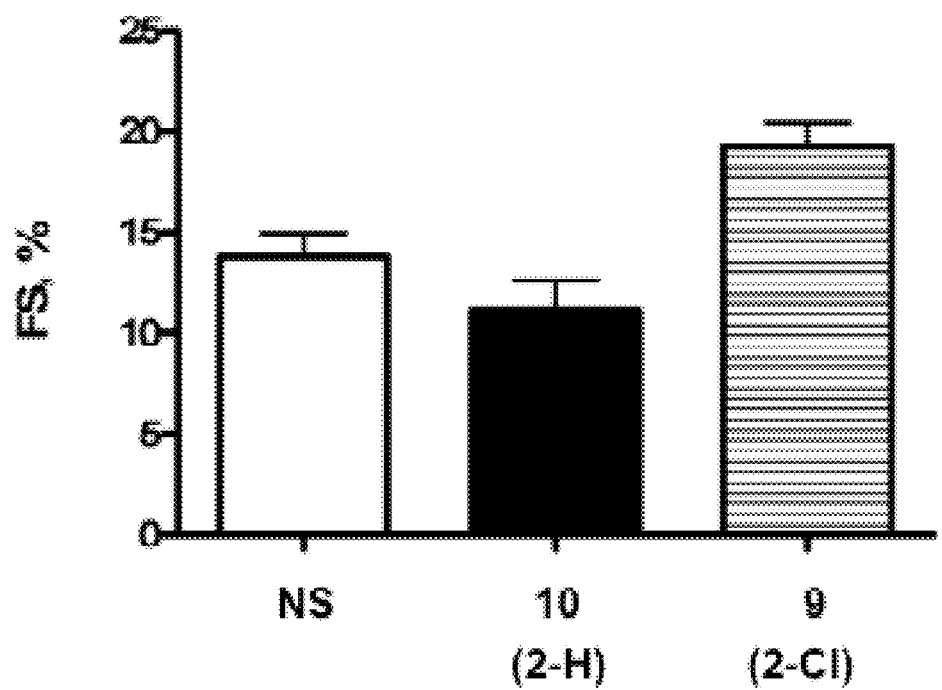

Various phosphonate derivatives were infused subcutaneously individually via an Alzet minipump in CSQ mice. After 28 days of infusion, the in vivo heart function was assessed using echocardiography-derived fractional shortening (FS), which is the ratio of the change in the diameter of the left ventricle between the contracted and relaxed states. Thus, a lower percentage represents a decrease in function. Two of the phosphonates, 4 and 9, were able to cause an improved FS as compared to vehicle (FIG. 1, Table 1) and in comparison to the reference nucleotide 3. Other analogues tested in this model (2-H analogues 5, 8, and 10, and 2-Cl analogues 7 and 11) had lower FS values. Compounds 7, 8, and 10 were not protective at this dose, i.e., FS in vehicle control-treated CSQ mice was similar to that from mice treated chronically with these nucleotides. Thus, in the saturated phosphonate series, the orientation of the phosphorous relative to the methanocarba ring was somewhat structurally permissive, although inclusion of an olefin in the spacer prevented the cardioprotective action. In 11, one OH group of the phosphonate has been replaced with $CH_3$. This reduces the overall charge on the molecule and is intended to make it more bioavailable. Evidently, the binding site of the receptor requires both oxygens for the most favorable improvement in FS. Therefore, as summarized in FIG. 1, the most significant improvement in FS was associated with the saturated homologues containing a 2-Cl substitution and an unmodified phosphonate group, 4 and 9.

Figure 2:
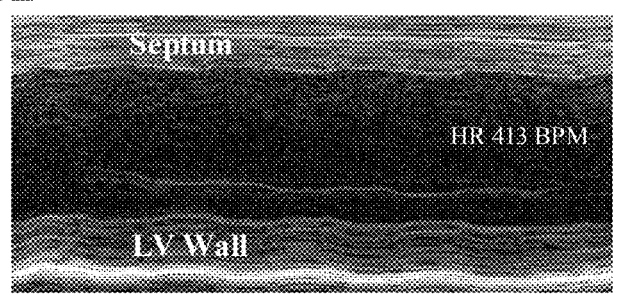
FIG. 2 shows that chronic infusion of compound 4 resulted in improved echocardiographically derived FS in CSQ heart failure mice. Following chronic subcutaneous infusion of NS or compound 4, two-dimensional directed M-mode echocardiography was carried out as described in Methods. The heart rate (HR) is indicated on each figure. Representative M-mode echocardiography was shown for a CSQ animal infused with normal saline (NS) (A) and for a CSQ mouse infused with compound 4 (B). A heart from the NS-infused mice showed less shortening of both septum and LV free wall than did compound 4-infused mice.
Figure 2:
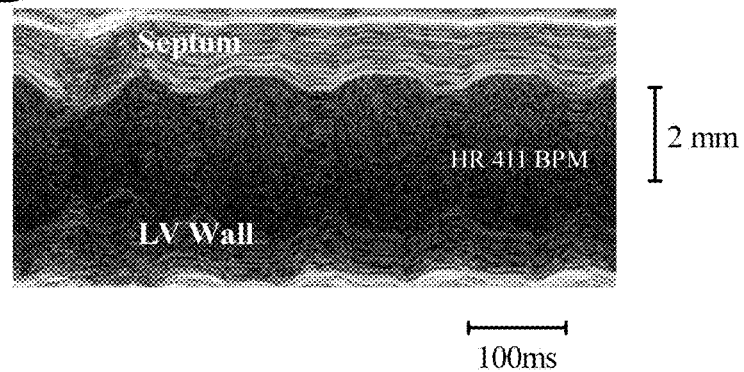

An echocardiographic image of compound 4-versus normal saline (NS)-infused CSQ hearts is shown in FIG. 2. An increased shortening of both the septum and left ventricular (LV) free wall was evident in the heart from mice treated with 4 in comparison to that from vehicle (NS)-infused mice.

Figure 3:
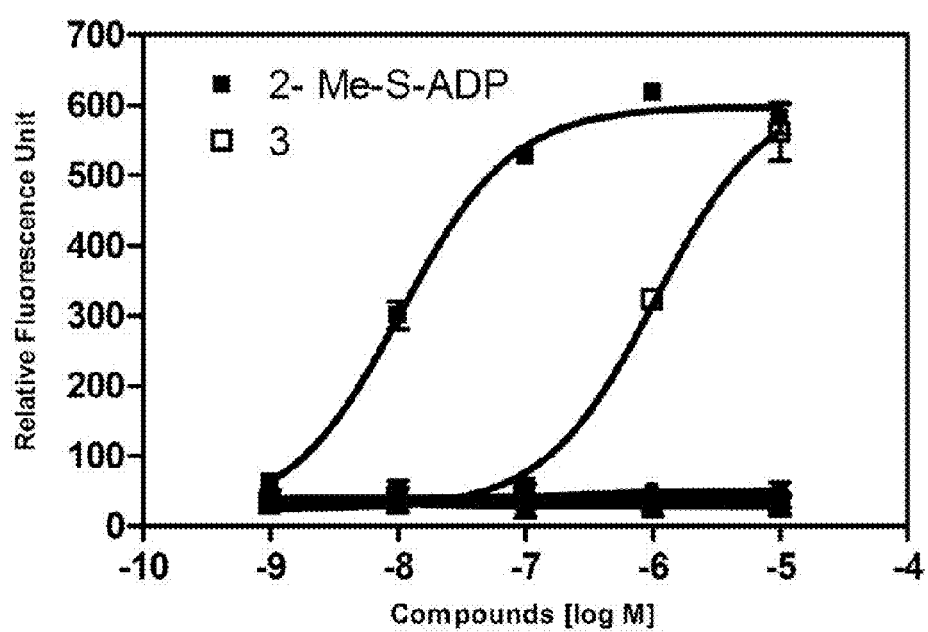
FIG. 3 shows changes in intracellular calcium in 1321N1 human astrocytoma cells stably expressing the hP2Y$_1$ receptor. Fluorescence in response to a known hP2Y$_1$ receptor agonist 2-MeSADP (EC$_{50}$ 10.3±0.4 nM), compound 3 (EC$_{50}$ 722±55 nM), or the phosphonate analogues (compounds 4-11, all inactive at 10 µM) was quantified using a FLIPR-Tetra.

The ability of the nucleotide analogues to activate the human $P2Y_1$ receptor (Table 1) was also investigated. This receptor is vasodilatory, and agonist action at this subtype would be expected to be relevant to the observed cardiac effects. Compound 3 was previously reported to activate phospholipase C (PLC) mediated by the human $P2Y_1$ receptor. The phosphonate derivatives were tested in a FLIPR assay of calcium flux induced in 1321N1 astrocytoma cells stably expressing the human $P2Y_1$ receptor. The known $P2Y_1$ receptor agonist 2-MeSADP induced a $Ca^{2+}$ flux with an $EC_{50}$ of 10.3±0.4 nM (n=3) in the transfected cells (FIG. 3), but in control 1321N1 astrocytoma cells there was no change in intracellular $Ca^{2+}$ in response to 10 μM 2-MeSADP. At concentrations up to 10 μM, the phosphonate analogues 4-11 produced no effect in the same assay. However, compound 3 was active in this assay as an agonist, with an $EC_{50}$ of 722±55 nM (n=3). The maximal effect of 3 was about 80% of that of the full agonist 2-MeSADP.

In conclusion, the range of carbocyclic nucleotide analogues that represent potential candidates for the treatment of heart failure has been expanded. A more chemically and biologically stable linkage than the phosphate group in compound 3 has been introduced in the form of phosphonate groups, which in several cases preserve heart contractile function in a genetic model of heart failure. Facile routes for the synthesis of phosphonate analogues of compound 3 in the conformationally constrained (N)-methanocarba series were developed using Michaelis-Arbuzov and Wittig reactions. A further advantage of the phosphonate linkage is that the undesired activity as agonist of the $P2Y_1$ receptor has been eliminated. The beneficial effects of these nucleotidase-resistant agonists can now be explored in additional models of cardiac failure and cardiomyopathy.

Example 3

Additional Chemical Synthesis

The novel, charged 5'-phosphonate (4a-7a, Table 2a) and 5'-ester derivatives (8a-17a, Table 2) in the (N)-methanocarba series were synthesized by the methods shown in Schemes 1a-4a. Modifications of compound 3 include S substitution of O at phosphorus (4a, 5a) (Scheme 1a) and the introduction of deuterium at the 5' position in 6a (Scheme 2a), both of which are believed to improve stability in vivo. Compound 7a was prepared as the 2-iodo equivalent of 4 (Scheme 3a). The corresponding ester-masked derivatives (8a-17a), including prodrug derivatives of the reference compounds 3, 4, and 7, were prepared, either from intermediates or as shown in Schemes 1a-4a. Most of the esters consisted of diethyl esters, but one diisopropyl ester 11a was included. Phosphotriester derivatives included 8a (and its dideuterated equivalent 15a) and thio derivatives 12a-14a. In some cases, the phosphorus atom of a phosphonate was bonded directly to the 5' carbon atom, e.g. in 2-iodo derivative 16a, while in other cases, a carbon atom was added at that position to form an extended saturated phosphonate analogue, e.g. in diethylester derivative 10a. Compound 17a was prepared as the 2-ethynyl equivalent of 9a.

The synthetic route for various thio derivatives is shown in Scheme 1a. Previously reported nucleoside 18a used as key intermediate to generate these thio analogues, initial acetonide deprotection using 10% aqueous trifluoroacetic acid in $CH_2Cl_2$ afforded the 2',3' and 5'-trihydroxy nucleoside 19a. 5'-Thiophosphate 5a could be generated from intermediate 19a by treating it with thiophosphoryl chloride, 1,8-bis-(dimethylamino)naphthalene (proton sponge) and pyridine followed by quenching the reaction with tetraethylammonium bicarbonate (TEAB). However, we anticipate that subjecting nucleoside 19a to the same conditions followed by quenching with EtOH should provide 5'-thiophosphate-diethylester 13a. 5'-Iodination of the nucleoside intermediate 18a using $PPh_3$, $I_2$, and imidazole in anhydrous THF afforded the 5'-iodo nucleoside 29a. Subsequent deprotection of the acetonide protecting group of 29a using Dowex-50 resin afforded the 5'-iodo-2',3'-dihydroxy nucleoside 21a (Scheme 1a) as a key intermediate to generate 5'-phosphorothiate 12a, 5'-phosphorothiate diethylester 4a and 5'-phosphorodithioate diethylester 14a (Scheme 1a). Treating key nucleotide 21a with sodium O,O-diethylthiophosphate in EtOH could generate 5'-phosphorothiate diethylester 4a. Treatment of nucleoside 21a with trisodium thiophosphate in H$_2$O for 3 d afforded 5'-phosphorothiate 12a in 57% yield. Alternately, reacting the nucleotide 21a with the diethyl dithiophosphate potassium salt in DMF would yield 5'-phosphorodithioate diethylester 14a (Scheme 1a).

5'-Dideuteromethyl (N)-methanocarba monophosphate 6a and its diethyl ester analogue 15a were synthesized from nucleoside 22a (Scheme 2a). Initial amination at the C6 position of the purine base using 2M NH$_3$/i-ProH followed by reduction of the ethyl ester using LiBD$_4$ in anhydrous THF provided the 5'-hydroxyduetiromethyl nucleoside 24a. The nucleoside 24a was phosphorylated by first reacting with either di-t-butyl or di-ethyl analogue of N,N-diethylphosphoramidite and tetrazole followed by treatment with m-chloroperbenzoic acid to afford the corresponding di-t-butyl or di-ethyl phosphate diester derivatives 25a and 26a, respectively. Both t-butyl groups and the acetonide group in 26a were deprotected simultaneously by using Dowex-50 resin in the acid form to afford the 5'-dideuteromethyl monophosphate 6a. The synthesis of dideuteromethyl phosphonate diethylester 15a could be achieved by chemoselectively deprotection of acetonide group of nucleotide 25a using Dowex-50 resin (Scheme 2a).

Synthetic procedures for various 2-position substituted adenine phosphonates (7a, 32a) and phosphonate diethylesters (9a, 16a, 17a) started with installation of the nucleobase on a previously described sugar 27a by a Mitsunobu base coupling reaction using PPh$_3$, diisopropyl azodicarboxylate, and 6-chloro-2-iodopurine to generate 6-chloro-2-iodo-purine nucleotide 28a. Next, amination at the C6 position of compound 28a using 2M NH$_3$ in isopropanol (Scheme 3a) afforded the nucleotide 29a. Finally, simultaneous deprotection of both the phosphonate diester and acetonide of 29a was achieved upon treatment with freshly opened iodotrimethylsilane in CH$_2$Cl$_2$ to obtain target phosphonate 7a in 49% yield. Alternately, treatment of 2-chloro (30a) and 2-iodo (29a) nucleotides with Dowex-50 ion-exchange resin resulted in a chemo-selective deprotection of acetonide and resulted in a formation of corresponding 2-chloro and 2-iodo diethyl phosphonate esters 9a and 16a, respectively. 2-Ethynyl-substituted phosphonate diethylester 17a and phosphonate 32a derivatives were generated using initial installation of acetylene group following the classical Sonogashira coupling protocol using trimethylsilylacetylene, Pd(Ph$_3$)$_4$, CuI, TEA in anhydrous DMF. Subsequently, TMS protection at acetylene was removed using TBAF in anhydrous THF to afford 2-ethynyl-substituted phosphonate diester 31a. Similar to the other derivatives, 2-ethynyl-substituted adenine phosphonates (32a) and phosphonate diethylesters (17a) were synthesized using the Dowex-based chemoselective and iodotrimethylsilylane-based full deprotection protocols, respectively.

The saturated long-chain phosphonate esters 10a and 11a were synthesized by oxidation of known alcohol 33a to the 5'-aldehyde 34a in 80% yield. It is noteworthy that not even a small amount of decomposition of the aldehyde was observed after storage at room temperature (rt) for several d. The α,β-unsaturated alkyl phosphonate ester 35a could be prepared from aldehyde 34a in a Wittig-type reaction using tetraethyl methylenediphosphonate and sodium hydride in anhydrous THF. Amination at the 6-position of purine base would give us compound 36a, which could be subjected to chemo selective reduction of alkene using the diimide generated in situ from O-nitrobenzenesulfonylhydrazide, Et$_3$N in CH$_2$Cl$_2$ to get the long-chain saturated phosphonate diethyl ester 37a. Acetonide deprotection of compounds 37a and 38a using Dowex-50 resin resulted in formation of diethyl and diisopropyl phosphonate esters, target compounds 10a and 11a, respectively.

Example 4

Additional Biological Evaluation

Various phosphonate derivatives were infused subcutaneously individually via an Alzet minipump in CSQ mice. After 14 days of infusion, the in vivo heart function was assessed using echocardiography-derived fractional shortening (FS), which is the ratio of the change in the diameter of the left ventricle between the contracted and relaxed states (Table 2). Thus, a lower percentage represents a decrease in function.

The structure activity relationships (SARs) of the charged nucleotide analogs were explored. Two-week infusion of the 2-iodo phosphonate derivative 7a (n=5 mice) did not improve FS or prevent LV wall thinning in mice with heart failure (data not shown). Thus, 2-Cl substitution of the adenine moiety as in phosphonate 4 was essential for activity; substitution with iodo in 7a abolished protection. Several new phosphate and phosphonate analogues, such as thio derivatives, were compared. A 2-week infusion of thiophosphate 4a (n=5), containing a 5'-thioester, could protect the CSQ mice with a better preservation of LV septal (0.492±0.012 mm) and posterior (0.493±0.016 mm) wall thickness as compared those obtained in NS-infused (both septal and posterior: 0.450±0.007 mm) CSQ mice (P<0.05, data not shown). Thus, substitution of oxygen with sulfur was tolerated.

Figure 4:
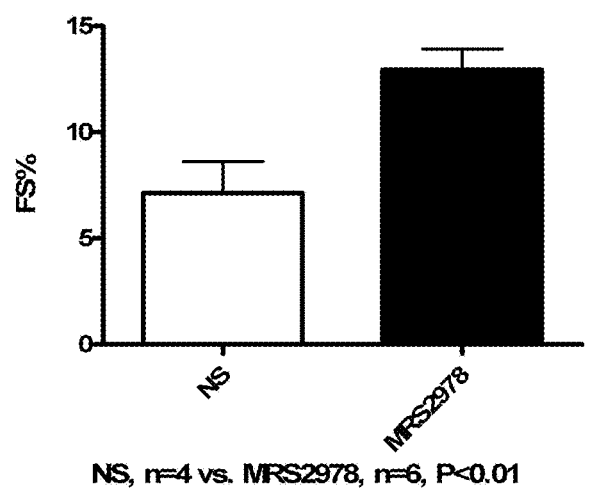
FIG. 4 shows chronic infusion of compound 11a caused an increased LV contractile fractional shortening in calsequestrin (CSQ)-overexpressing model of heart failure. Following 14 days of infusion of compound 11a (n=6 mice) or normal saline (NS, n=4) in CSQ mice, LV fractional shortening (FS) was compared between the two groups. Treatment with compound 11a resulted in improved in vivo LV contractile function in animals with heart failure. Data are mean and standard error.
Figure 5A:
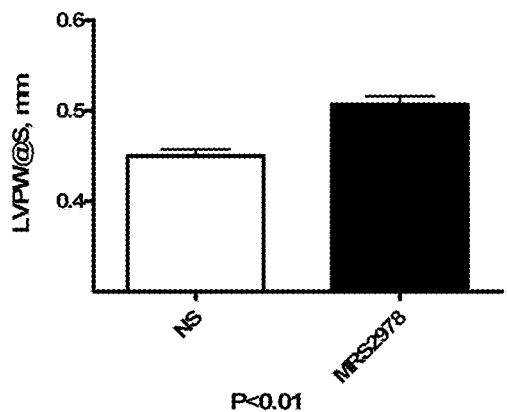
FIG. 5 shows chronic infusion of compound 11a resulted in preservation of LV wall thickness in CSQ-overexpressing heart failure mice. The in vivo cardiac wall thickening was assessed by echocardiography following 14 days of infusion of compound 11a or NS in CSQ mice. a: In compound 11a-infused animals, the LV posterior wall thickness during systole (LVPW@S) was greater (P<0.05) than that in NS-infused CSQ mice (P<0.01). b: Similar data were obtained when septal thickness during systole (IVS@S) was compared between compound 11a-treated and NS-treated CSQ mice, P<MRS 0.01. c: LV posterior wall thickness during diastole was also greater in compound 11a-infused than in NS-infused CSQ mice, P<0.05. Data are expressed as mean±SEM. The data suggest that treatment with compound 11a was able to prevent LV wall thinning in heart failure.
Figure 5B:
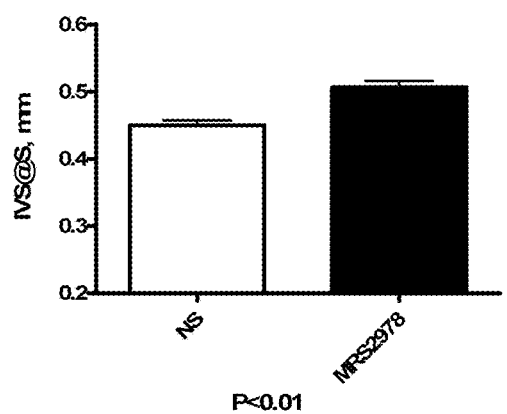
Figure 5C:
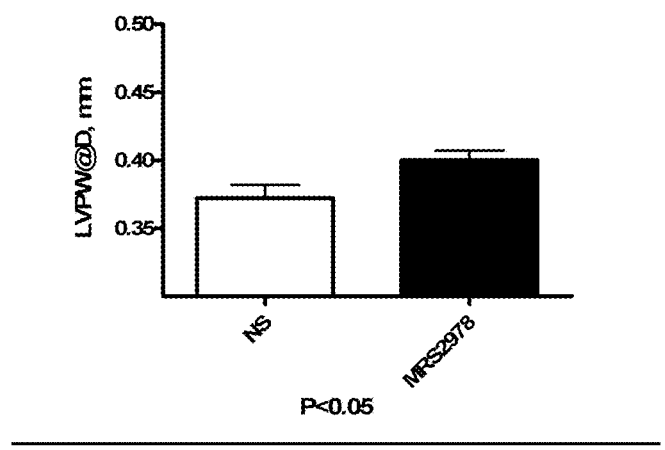

The structure activity relationships (SARs) of the masked (uncharged) nucleotide analogs was explored using the same experimental model. Only some of the ester derivatives of the previously characterized cardioprotective agents 3, 4, and 9 were shown to act in vivo. These findings implied that a cleavage step in vivo to liberate the charged nucleotide active drug was necessary. Among the prodrug derivatives, diisopropyl ester 11a of phosphonate (1'S,2'R,3'S,4'R,5'S)-4'-(6-amino-2-chloropurin-9-yl)-2',3'-(dihydroxy)-1'-(phosphonoethylene)-bicyclo[3.1.0]hexane 9 was highly efficacious. This phosphonate diester resulted in an improved FS as compared to vehicle (FIG. 4, Table 2). In mice infused with compound 11a, the LV posterior wall thickness and septal thickness during systole and the LV posterior wall thickness during diastole were greater than those in NS-infused CSQ mice (FIG. 5). Other analogues tested in this model, e.g. 7a and 9a, had lower FS values and were not protective at this dose, i.e., FS in CSQ mice infused with compounds 7a and 9a was similar to that from normal saline-infused control mice. Furthermore, two-week infusion of 7 (n=5 mice) or 9a (n=4) did not improve FS or prevent LV wall thinning in CSQ mice with heart failure (data not shown). Thus, the lower homologue 1'-(phosphonoethylene) derivative 9a was less active than 11a, suggesting that unblocking of the esters in vivo depended on unhindered steric access to the phosphonyl group.

Experimental Procedures for Example 1

General Methods:

Compound 13 was either synthesized as reported or obtained as a custom synthesis from Natland International Corporation (Research Triangle Park, N.C.). All other reagents and solvents (regular and anhydrous) were of analytical grade and obtained from commercial suppliers and used without further purification. Reactions were conducted under an atmosphere of argon whenever anhydrous solvents were used. All reactions were monitored by thin-layer chromatography (TLC) using silica gel coated plates with a fluorescence indicator which were visualized: a) under UV light, b) by dipping in 5% conc. $H_2SO_4$ in absolute ethanol (v/v) followed by heating, or c) by dipping in a solution of anisaldehyde:$H_2SO_4$ (1:2, v/v) in MeOH followed by heating. Silica gel column chromatography was performed with silica gel ($SiO_2$, 200-400 mesh, 60 Å) using moderate air pressure. Evaporation of solvents was carried out under reduced pressure at a temperature below 50° C. After column chromatography, appropriate fractions were pooled, evaporated and dried at high vacuum for at least 12 h to give the obtained products in high purity. $^1$H NMR and $^{31}$P NMR ascertained sample purity. No corrections in yields were made for solvent of crystallization. $^1$H NMR and $^{31}$P NMR spectra were recorded at 300 MHz and 121.5 MHz, respectively. Chemical shifts are reported in parts per million (ppm) relative to tetramethylsilane or deuterated solvent as the internal standard (dH: $CDCl_3$ 7.26 ppm). For compounds 38-41, the integral of the H3'-signal of the least predominant isomer was set to 1.0. Systematic compound names for bicyclic nucleosides are given according to the von Baeyer nomenclature. High resolution mass spectroscopic (HRMS) measurements were performed on a proteomics optimized Q-TOF-2 (Micromass-Waters) using external calibration with polyalanine. Observed mass accuracies are those expected on the basis of known performance of the instrument as well as the trends in masses of standard compounds observed at intervals during the series of measurements. Reported masses are observed masses uncorrected for this time-dependent drift in mass accuracy.

Purification of the nucleotide derivatives for biological testing was performed by HPLC with a Luna 5 μm RP-C18(2) semipreparative column (250×10.0 mm; Phenomenex, Torrance, Calif.) under the following conditions: flow rate of 2 mL/min; 10 mM triethylammonium acetate (TEAA)-$CH_3CN$ from 100:0 (v/v) to 70:30 (v/v) in 30 min and isolated in the triethylammonium salt form. Analytical purity of compounds was checked using a Hewlett-Packard 1100 HPLC equipped with Zorbax SB-Aq 5 μm analytical column (50×4.6 mm; Agilent Technologies Inc, Palo Alto, Calif.). Mobile phase: linear gradient solvent system: 5 mM TBAP (tetrabutylammonium dihydrogenphosphate)-$CH_3CN$ from 80:20 to 40:60 in 13 min; the flow rate was 0.5 mL/min. Peaks were detected by UV absorption with a diode array detector at 254, 275, and 280 nm. All derivatives tested for biological activity showed >99% purity by HPLC analysis (detection at 254 nm).

Ethyl-(1S,2R,3S,4S,5S)-2,3-O-(isopropylidene)-4-O-(tert-butyldimethylsilyl)-bicyclo[3.1.0]hexanecarboxylate (14): Known alcohol 13 (0.83 g, 3.40 mmol) was coevaporated with anhydrous toluene (2×10 mL) and dissolved in anhydrous $CH_2Cl_2$ (25 mL). Imidazole (0.69 g, 10.20 mmol), DMAP (0.04 g, 0.34 mmol) and tert-butylchlorodiphenylsilane (1.74 mL, 6.81 mmol) were added. After stirring at rt for 16 h, the reaction mixture was diluted with $CH_2Cl_2$ (50 mL) and washed with sat. aq. $NaHCO_3$ (1×30 mL). The aqueous phase was back-extracted with $CH_2Cl_2$ (2×50 mL). The combined organic phase was evaporated to dryness, and the resulting crude residue was purified by silica gel column chromatography (0-8% EtOAc in petroleum ether, v/v) to afford compound 14 (1.52 mg, 93%) as a colorless oil. $R_f$=0.3 (10% EtOAc in $CH_2Cl_2$, v/v); ESI-HRMS m/z 519.1981 ([M+K]$^+$, $C_{28}H_{36}O_5Si.K^+$: Calcd. 519.1969); $^1$H NMR ($CDCl_3$) δ 7.69-7.80 (m, 4H, Ph), 7.32-7.45 (m, 6H, Ph), 5.11 (d, 1H, J=6.6 Hz), 4.42 (t, 1H, J=6.1 Hz), 3.99-4.18 (m, 3H), 2.17-2.25 (m, 1H), 1.91 (t, 1H, J=5.5 Hz), 1.57 (s, 3H), 1.45-1.53 (m, 1H), 1.18-1.24 (m, 6H), 1.07 (s, 9H).

(1S,2R,3S,4S,5S)-1-Hydroxymethyl-2,3-O-(isopropylidene)-4-O-(tert-butyldimethylsilyl)-bicyclo[3.1.0]hexane (15): Compound 14 (0.98 g, 2.04 mmol) was coevaporated with anhydrous toluene (2×20 mL), dissolved in anhydrous THF (30 mL) and cooled to −70° C. DIBAL-H (1.5 M in toluene 10.8 mL, 16.32 mmol) was added slowly to this solution over 20 min. After stirring at −70° C. for 3 h, the reaction was quenched with the very careful addition of ice-cold MeOH (20 mL), followed by warming the reaction mixture to rt. 1 M cold $H_2SO_4$ (20 mL) was added to the mixture and it was stirred for 1 h, followed by addition of $CH_2Cl_2$ (100 mL). The phases were separated, and the aqueous phase was extracted with $CH_2Cl_2$ (3×35 mL). The combined organic phase was evaporated to dryness, and the resulting residue was purified by silica gel column chromatography (0-45% EtOAc in petroleum ether, v/v) to afford compound 15 (0.74 g, 82%) as a colorless oil. $R_f$=0.4 (50% EtOAc in petroleum ether, v/v); ESI-HRMS m/z 461.2112 ([M+Na]$^+$, $C_{26}H_{34}O_4Si.Na^+$: Calcd. 461.2124); $^1$H NMR ($CDCl_3$) δ 7.71-7.78 (m, 4H, Ph), 7.31-7.44 (m, 6H, Ph), 4.73 (d, 1H, J=6.5 Hz), 4.44 (t, 1H, J=6.5 Hz), 4.09 (t, 1H, J=6.5 Hz), 3.59-3.67 (m, 1H), 3.41-3.49 (m, 1H), 1.57-1.59 (m, 4H), 1.33 (t, 1H, J=5.5 Hz), 1.20 (s, 3H), 1.07 (s, 9H), 0.56-0.68 (m, 1H).

(1S,2R,3S,4S,5S)-2,3-O-(Isopropylidene)-1-methanesulfonyloxymethyl-4-O-(tert-butyldimethylsilyl)-bicyclo[3.1.0]hexane (16): Compound 15 (0.59 g, 1.36 mmol) was coevaporated with anhydrous toluene (2×20 mL), dissolved in anhydrous $CH_2Cl_2$ (30 mL) and cooled to 0° C. Triethylamine (0.95 mL, 6.79 mmol) and methanesulfonyl chloride (0.22 mL, 2.72 mol) were added at 0° C. over 10 min. After warming the reaction mixture to rt, it was stirred for 17 h. Then, ice-cold $H_2O$ (25 mL) was added and the mixture was extracted with EtOAc (2×45 mL). The combined organic phase was washed with sat. aq. $NaHCO_3$ (2×35 mL) and evaporated to dryness. The resulting residue was purified by silica gel column chromatography (0-50% EtOAc in petroleum ether, v/v) to afford compound 16 (0.68 g, 96%) as a colorless oil. $R_f$=0.5 (50% EtOAc in petroleum ether, v/v); ESI-HRMS m/z 555.1623 ([M+K]$^+$, $C_{27}H_{36}O_6SSi.K^+$: Calcd. 555.1639); $^1$H NMR ($CDCl_3$) δ 7.69-7.77 (m, 4H, Ph), 7.31-7.45 (m, 6H, Ph), 4.69 (d, 1H, J=6.5 Hz), 4.47 (t, 1H, J=6.5 Hz), 4.37-4.43 (dd, 1H, J=10.9 Hz), 4.07 (t, 1H, J=6.5 Hz), 3.90-3.95 (dd, 1H, J=10.9 Hz), 2.99 (s, 3H), 1.67-1.72 (m, 2H), 1.55 (s, 3H), 1.20 (s, 3H), 1.08 (s, 9H), 0.72-0.79 (m, 1H).

(1S,2R,3S,4S,5S)-1-Iodomethyl-2,3-O-(isopropylidene)-4-O-(tert-butyldimethylsilyl)-bicyclo[3.1.0]hexane (17): Compound 16 (0.68 g, 1.32 mmol) was coevaporated with anhydrous toluene (2×20 mL), and the residue dissolved in anhydrous 1,4-dioxane (25 mL). NaI (0.59 g, 3.94 mol) was added to the mixture, and it was heated to 65° C. After stirring for 17 h, the reaction mixture was cooled to rt and diluted with $H_2O$ (25 mL) and $CH_2Cl_2$ (75 mL). The phases were separated, and the aqueous phase was extracted with $CH_2Cl_2$ (3×35 mL). The combined organic phase was evaporated to dryness, and the resulting residue was purified by silica gel column chromatography (0-20% EtOAc in petroleum ether, v/v) to afford compound 17 (0.69 g, 95%) as a colorless oil. $R_f$=0.5 (20% EtOAc in petroleum ether, v/v); ESI-HRMS m/z 549.1322 ([M+H]$^+$, $C_{26}H_{33}IO_3Si.H^+$: Calcd. 549.1322); $^1$H NMR ($CDCl_3$) δ 7.68-7.77 (m, 4H, Ph), 7.32-7.46 (m, 6H, Ph), 4.69 (d, 1H, J=6.5 Hz), 4.43 (t, 1H, J=6.5 Hz), 4.09 (t, 1H, J=6.5 Hz), 3.55-3.60 (dd, 1H, J=10.5 Hz), 3.97-4.02 (dd, 1H, J=10.5 Hz), 2.02 (t, 1H, J=4.9 Hz), 1.54-1.57 (s, 4H), 1.20 (s, 3H), 1.07 (s, 9H), 0.83-0.90 (m, 1H).

Diethyl-(1S,2R,3S,4S,5S)-2,3-O-(isopropylidene)-4-O-(tert-butyldimethylsilyl)-bicyclo[3.1.0]hexane phosphonate (18): Compound 17 (0.68 g, 1.23 mmol) was dissolved in triethylphosphite (17 mL), and the mixture was heated to 110° C. After stirring for 17 h, the reaction mixture was cooled to rt and evaporated to dryness. The resulting residue was purified by silica gel column chromatography (0-90% EtOAc in petroleum ether, v/v) to afford compound 18 (0.65 g, 94%) as a colorless oil. $R_f$=0.3 (EtOAc); ESI-HRMS m/z 559.2665 ([M+H]$^+$, $C_{30}H_{43}O_6PSi.H^+$: Calcd. 559.2645); $^1$H NMR (CDCl$_3$) δ 7.71-7.77 (m, 4H, Ph), 7.30-7.43 (m, 6H, Ph), 4.80 (d, 1H, J=6.5 Hz), 4.47 (t, 1H, J=6.5 Hz), 4.10 (t, 1H, J=6.5 Hz), 3.91-4.05 (m, 4H), 2.22 (t, 1H, J=16.5 Hz), 1.63-1.71 (m, 1H), 1.57-1.61 (m, 2H), 1.55 (s, 3H), 1.22 (t, 3H, J=7.2 Hz), 1.20 (t, 3H, J=7.2 Hz), 1.19 (s, 3H), 1.07 (s, 9H), 0.53-0.60 (m, 1H). $^{31}$P NMR (CDCl$_3$) δ29.93.

Diethyl-(1S,2R,3S,4S,5S)-4-hydroxy-2,3-O-(isopropylidene)-bicyclo[3.1.0]hexane phosphonate (19): Compound 18 (0.65 g, 1.16 mmol) was dissolved in a mixture of THF (20 mL) and tetrabutylammonium fluoride (1 M in THF, 2.91 mL, 2.91 mmol). After stirring for 17 h, the reaction mixture was evaporated to dryness. The resulting residue was purified by silica gel column chromatography (0-7% MeOH in EtOAc, v/v) to afford compound 19 (0.33 g, 88%) as a colorless oil. $R_f$=0.3 (5% MeOH in EtOAc, v/v); ESI-HRMS m/z 321.1466 [M+H]$^+$, $C_{14}H_{25}O_6P.H^+$: Calcd. 321.1467); $^1$H NMR (CDCl$_3$) δ 5.02 (d, 1H, J=6.1 Hz), 4.50-4.58 (m, 2H), 4.02-4.17 (m, 4H), 2.32-2.37 (m, 1H), 2.26 (t, 1H, J=16.5 Hz), 1.88-1.96 (m, 1H), 1.61-1.74 (m, 1H), 1.54 (s, 3H), 1.32 (t, 6H, J=7.2 Hz), 1.28 (s, 3H), 1.21-1.27 (m, 1H), 0.60-0.67 (m, 1H). $^{31}$P NMR (CDCl$_3$) δ29.01.

Diethyl-(1'S,2'R,3'S,4'R,5'S)-4'-(2,6-dichloropurin-9-yl)-2',3'-O-(isopropylidene)-bicyclo[3.1.0]hexane phosphonate (20): Diisopropyl azodicarboxylate (97 μL, 0.49 mmol) was added at rt to a mixture of triphenylphosphine (128 mg, 0.49 mmol) and 2,6-dichloropurine (92 mg, 0.49 mmol) in anhydrous THF (3 mL). After stirring for 30 min, a solution of compound 19 (78 mg, 0.25 mmol) in THF (3 mL) was added to the mixture. After stirring for 51 h, the reaction mixture was evaporated to dryness. The resulting residue was purified by silica gel column chromatography (0-4% MeOH in EtOAc, v/v) to afford nucleoside 20 (90 mg, 75%) as a white solid material. $R_f$=0.5 (5% MeOH in EtOAc, v/v); ESI-HRMS m/z 491.1013 [M+H]$^+$, $C_{19}H_{25}Cl_2N_4O_5P.H^+$: Calcd. 491.1018); $^1$H NMR (CDCl$_3$) δ 8.82 (s, 1H), 5.39 (d, 1H, J=6.5 Hz), 5.10 (s, 1H), 4.61 (d, 1H, J=6.5 Hz), 4.02-4.21 (m, 4H), 2.46 (t, 1H, J=16.5 Hz), 1.91-2.06 (m, 1H), 1.74-1.82 (m, 1H), 1.54 (s, 3H), 1.32 (t, 3H, J=7.2 Hz), 1.26 (t, 3H, J=7.2 Hz), 1.24 (s, 3H), 1.08-1.21 (m, 1H), 0.97-1.06 (m, 1H).

Diethyl-(1'S,2'R,3'S,4'R,5'S)-4'-(6-amino-2-chloropurin-9-yl)-2',3'-O-(isopropylidene)-bicyclo[3.1.0]hexane phosphonate (21): Nucleoside 20 (90 mg, 0.19 mmol) was treated with 2 M NH$_3$ in i-PrOH (5 mL), and the mixture was heated to 70° C. and stirred for 17 h. The reaction mixture was evaporated to dryness, and the resulting residue was purified by silica gel column chromatography (0-5% MeOH in CH$_2$Cl$_2$, v/v) to afford nucleoside 21 (70 mg, 80%) as a white solid material. $R_f$=0.5 (5% MeOH in CH$_2$Cl$_2$, v/v); ESI-HRMS m/z 472.1519 [M+H]$^+$, $C_{19}H_{27}ClN_5O_5P.H^+$: Calcd. 472.1517); $^1$H NMR (CDCl$_3$) δ 8.31 (s, 1H), 5.98 (s, 2H), 5.36 (d, 1H, J=7.1 Hz), 4.97 (s, 1H), 4.61 (d, 1H, J=6.5 Hz), 4.03-4.19 (m, 4H), 2.39 (t, 1H, J=16.5 Hz), 2.03-2.17 (m, 1H), 1.70-1.77 (m, 1H), 1.52 (s, 3H), 1.32 (t, 3H, J=7.2 Hz), 1.25 (t, 3H, J=7.2 Hz), 1.23 (s, 3H), 1.18-1.21 (m, 1H), 0.96-1.04 (m, 1H).

(1'S,2'R,3'S,4'R,5'S)-4'-(6-Amino-2-chloropurin-9-yl)-2',3'-(dihydroxy)-1'-(phosphonomethylene)-bicyclo[3.1.0]hexane (4): Nucleoside 21 (30 mg, 0.064 mmol) was coevaporated with anhydrous toluene (3×3 mL) and dissolved in anhydrous CH$_2$Cl$_2$ (3 mL). To this solution was added iodotrimethylsilane (91 μL, 0.64 mmol). After stirring for 17 h, the reaction mixture was cooled to 0° C. followed by the addition of ice-cold H$_2$O (25 mL) and CH$_2$Cl$_2$ (25 mL). The phases were separated, and the aqueous phase washed with CH$_2$Cl$_2$ (1×35 mL) and diethyl ether (3×35 mL). The resulting aqueous phase evaporated to dryness and purified by HPLC (retention time: 19.1 min) to afford 4 (8.5 mg, 23%) as a white solid material. ESI-HRMS m/z 374.0397 [M−H]$^-$, $C_{12}H_{14}ClN_5O_5P^-$: Calcd. 374.0421); $^1$H NMR (D$_2$O) δ8.21 (s, 1H), 4.71 (s, 1H), 4.57 (d, 1H, J=6.6 Hz), 4.01 (d, 1H, J=6.6 Hz), 3.19 (q, 24H, J=7.2 Hz), 2.23 (t, 1H, 15.5 Hz), 1.63-1.77 (m, 2H), 1.42-1.49 (m, 1H), 1.26 (t, 36H), 0.96-1.04 (m, 1H). $^{31}$P NMR (D$_2$O) δ 23.68. Purity >99% by HPLC (retention time: 4.51 min).

Diethyl-(1'S,2'R,3'S,4'R,5'S)-4'-(6-chloropurin-9-yl)-2',3'-O-(isopropylidene)-bicyclo[3.1.0]hexane phosphonate (22): Diisopropyl azodicarboxylate (100 μL, 0.50 mmol) was added at rt to a mixture of triphenylphosphine (133 mg, 0.50 mmol) and 6-chloropurine (96 mg, 0.50 mmol) in anhydrous THF (3 mL). After stirring the mixture for 30 min, a solution of compound 19 (81 mg, 0.26 mmol) in THF (3 mL) was added. After stirring for 17 h, the reaction mixture was evaporated to dryness. The resulting residue was purified by silica gel column chromatography (0-4% MeOH in EtOAc, v/v) to afford nucleoside 22 (100 mg, 87%) as a white solid material. $R_f$=0.5 (5% MeOH in EtOAc, v/v); ESI-HRMS m/z 457.1417 [M+H]$^+$, $C_{19}H_{26}ClN_4O_5P.H^+$: Calcd. 457.1408); $^1$H NMR (CDCl$_3$) δ 8.84 (s, 1H), 8.78 (s, 1H), 5.39 (d, 1H, J=6.5 Hz), 5.15 (s, 1H), 4.62 (d, 1H, J=6.5 Hz), 4.07-4.21 (m, 4H), 2.44 (t, 1H, J=16.5 Hz), 1.94-2.18 (m, 1H), 1.83-1.90 (m, 1H), 1.58 (s, 3H), 1.33 (t, 3H, J=7.2 Hz), 1.24-1.30 (m, 4H), 0.97-1.06 (m, 1H).

Diethyl-(1'S,2'R,3'S,4'R,5'S)-4'-(6-aminopurin-9-yl)-2',3'-O-(isopropylidene)-bicyclo[3.1.0]hexane phosphonate (23): Nucleoside 22 (100 mg, 0.22 mmol) was treated with 2 M NH$_3$ in i-PrOH (5 mL) and heated up to 70° C. After stirring for 19 h, the reaction mixture was evaporated to dryness. The resulting residue was purified by silica gel column chromatography (0-6% MeOH in CH$_2$Cl$_2$, v/v) to afford nucleoside 23 (75 mg, 79%) as a white solid material. $R_f$=0.4 (5% MeOH in CH$_2$Cl$_2$, v/v); ESI-HRMS m/z 438.1912 [M+H]$^+$, $C_{19}H_{28}N_5O_5P.H^+$: Calcd. 438.1906); $^1$H NMR (CDCl$_3$) δ8.38 (s, 1H), 8.36 (s, 1H), 5.54 (s, 2H), 5.36 (d, 1H, J=7.2 Hz), 5.03 (s, 1H), 4.63 (d, 1H, J=7.2 Hz), 4.06-4.20 (m, 4H), 2.38 (t, 1H, J=16.5 Hz), 1.97-2.11 (m, 1H), 1.78-1.85 (m, 1H), 1.68 (s, 3H), 1.32 (t, 3H, J=7.2 Hz), 1.27 (t, 3H, J=7.2 Hz), 1.23 (s, 3H), 1.18-1.21 (m, 1H), 0.95-1.02 (m, 1H).

(1'S,2'R,3'S,4'R,5'S)-4'-(6-Aminopurin-9-yl)-2',3'-(dihydroxy)-1'-(phosphonomethylene)-bicyclo[3.1.0]hexane (5): Nucleoside 23 (25 mg, 0.057 mmol) was coevaporated with anhydrous toluene (3×3 mL) and dissolved in anhydrous CH$_2$Cl$_2$ (3 mL). Iodotrimethylsilane (83 μL, 0.57 mmol) was added. After stirring for 15 h, the reaction mixture was cooled to 0° C. followed by the addition of ice-cold H$_2$O (25 mL) and CH$_2$Cl$_2$ (25 mL). The phases were separated, and the aqueous phase was washed with CH$_2$Cl$_2$ (1×35 mL) and diethyl ether (3×35 mL). The resulting aqueous phase was evaporated to dryness and purified by HPLC (retention time: 17.5 min) to afford 5 (6.8 mg, 27%) as a white solid material. ESI-HRMS m/z 340.0817 [M−H]$^-$, $C_{12}H_{15}N_5O_5P^-$: Calcd. 340.0811); $^1$H NMR (D$_2$O) δ 8.36 (s, 1H), 8.20 (s, 1H) 4.75 (s, 1H), 4.63 (d, 1H, J=6.1 Hz), 4.09 (d, 1H, J=6.1 Hz), 3.19 (q, 6H, J=7.2

Hz), 1.95-2.18 (m, 2H), 1.75-1.84 (m, 1H), 1.40-1.46 (m, 1H), 1.26 (t, 9H, J=7.2 Hz), 0.92-1.02 (m, 1H). $^{31}$P NMR (D$_2$O) δ 25.36. Purity >99% by HPLC (retention time: 2.9 min).

(1'S,2'R,3'S,4'R,5'S)-4'-(2,6-Dichloropurin-9-yl)-1'-formyl-2,3-O-(isopropylidine)-bicyclo[3.1.0]hexane (25): Known nucleoside 24 (150 mg, 0.41 mmol) was coevaporated with anhydrous toluene (2×8 mL) and dissolved in anhydrous CH$_2$Cl$_2$ (8 mL). Dess-Martin periodinane (257 mg, 0.61 mmol) was added. After stirring for 1 h, the reaction mixture was diluted with EtOAc (50 mL) and washed with an aqueous mixture of Na$_2$S$_2$O$_3$ and NaHCO$_3$ (3×35 mL). The aqueous phase was then extracted with EtOAc (2×35 mL). The combined organic phase was evaporated to dryness, and the resulting residue was purified by silica gel column chromatography (0-100% EtOAc in petroleum ether, v/v) to afford compound 25 (120 mg, 80%) as a white solid material. R$_f$=0.6 (EtOAc); ESI-HRMS m/z 369.0527 ([M+H]$^+$, C$_{15}$H$_{14}$Cl$_2$N$_4$O$_3$.H$^+$: Calcd. 369.0521); $^1$H NMR (CDCl$_3$) δ9.62 (s, 1H), 8.05 (s, 1H), 5.94 (d, 1H, J=7.2 Hz), 4.97 (s, 1H), 4.83 (d, 1H, J=7.2 Hz), 2.22-2.29 (m, 1H), 1.73 (t, 1H, J=6.1 Hz), 1.57 (s, 3H), 1.30 (s, 3H).

(1'S,2'R,3'S,4'R,5'S)-4'-(2,6-Dichloropurin-9-yl)-1'-[diisopropyl-(E)-ethenylphosphonate]-2',3'-O-(isopropylidine)-bicyclo[3.1.0]hexane (26): Tetraisopropyl methylenediphosphonate (165 μL, 0.51 mmol) was added to a suspension of NaH (60% dispersion in mineral oil, 25 mg, 1.02 mmol) in anhydrous THF (2 mL) at 0° C. After H$_2$ evolution ceased, a solution of aldehyde 25 (125 mg, 0.34 mmol) in anhydrous THF (3 mL) was added dropwise carefully at 0° C. After stirring at 0° C. for 1 h, the mixture was warmed to rt. After stirring at rt for 1 h, the reaction mixture was cooled to 0° C., and ice-cold H$_2$O (20 mL) was added. The phases were separated, and the aqueous phase was extracted with EtOAc (3×35 mL). The combined organic phase was evaporated to dryness, and the resulting residue was purified by silica gel column chromatography (0-4% MeOH in EtOAc, v/v) to afford nucleoside 26 (150 mg, 83%) as a white solid material. R$_f$=0.3 (EtOAc); ESI-HRMS m/z 531.1313 ([M+H]$^+$, C$_{22}$H$_{29}$Cl$_2$N$_4$O$_5$P.H$^+$: Calcd. 531.1331); $^1$H NMR (CDCl$_3$) δ 8.04 (s, 1H), 6.50-6.65 (m, 1H), 5.97 (t, 1H, J=17.1 Hz), 5.53 (d, 1H, J=7.2 Hz), 4.98 (s, 1H), 4.77 (d, 1H, J=7.2 Hz), 4.60-4.74 (m, 2H), 1.82-1.90 (m, 1H), 1.59 (s, 3H), 1.22-1.38 (m, 16H), 0.83-0.90 (m, 1H). $^{31}$P NMR (CDCl$_3$) δ16.64.

(1'S,2'R,3'S,4'R,5'S)-4'-(6-Amino-2-chloropurin-9-yl)-1'-[diisopropyl-(E)-ethenylphosphonate]-2,3-O-(isopropylidine)-bicyclo-[3.1.0]-hexane (27): Nucleoside 26 (100 mg, 0.19 mmol) was treated with 2 M NH$_3$ in i-PrOH (5 mL) and heated to 70° C. After stirring for 16 h, the reaction mixture was evaporated to dryness. The resulting residue was purified by silica gel column chromatography (0-8% MeOH in CH$_2$Cl$_2$, v/v) to afford nucleoside 27 (85 mg, 88%) as a white solid material. R$_f$=0.3 (5% MeoH in EtOAc, v/v); ESI-HRMS m/z 512.1821 ([M+H]$^+$, C$_{22}$H$_{31}$ClN$_5$O$_5$P.H$^+$: Calcd. 512.1830); $^1$H NMR (CDCl$_3$) δ7.69 (s, 1H), 6.52-6.68 (m, 1H), 5.94 (t, 1H, J=17.5 Hz), 5.75 (s, 2H), 5.51 (d, 1H, J=7.2 Hz), 4.91 (s, 1H), 4.76 (d, 1H, J=7.2 Hz), 4.59-4.73 (m, 2H), 1.80-1.89 (m, 1H), 1.61 (s, 3H), 1.21-1.37 (m, 15H), 1.08-1.17 (m, 1H), 0.77-0.95 (m, 1H).

(1'S,2'R,3'S,4'R,5'S)-4'-(6-Amino-2-chloropurin-9-yl)-2',3'-(dihydroxy)-1'-[(E)-phosphonoethenyl]-bicyclo[3.1.0]-hexane (7): Nucleoside 27 (12 mg, 0.023 mmol) was coevaporated with anhydrous toluene (3×2 mL) and dissolved in anhydrous CH$_2$Cl$_2$ (2 mL). Iodotrimethylsilane (35 μl, 0.24 mmol) was added. After stirring for 18 h, the reaction mixture was cooled to 0° C., followed by the addition of ice-cold H$_2$O (15 mL) and CH$_2$Cl$_2$ (15 mL). The phases were separated, and the aqueous phase was washed with CH$_2$Cl$_2$ (1×25 mL) and diethyl ether (3×35 mL). The resulting aqueous phase was evaporated to dryness and purified by HPLC (retention time: 22.8 min) to afford 7 (2.5 mg, 28%) as a white solid material. ESI-HRMS m/z 386.0403 [M−H]$^-$, C$_{13}$H$_{14}$N$_5$ClO$_5$P$^-$: Calcd. 386.0421); $^1$H NMR (D$_2$O) δ 7.99 (s, 1H), 6.21-6.36 (m, 1H), 6.06 (t, 1H, J=17.5 Hz), 4.84-4.89 (m, 1H), 4.06 (d, 1H, J=6.6 Hz), 3.22 (q, 3H, J=7.2 Hz), 1.99-2.06 (m, 1H), 1.78-1.87 (m, 1H), 1.29 (t, 6H, J=7.2 Hz), 1.21-1.26 (m, 1H). $^{31}$P NMR (D$_2$O) δ 14.68. Purity >99% by HPLC (retention time: 4.3 min)

(1'S,2'R,3'S,4'R,5'S)-4'-(6-Aminopurin-9-yl)-1'-(diisopropyl-phosphonoethenyl)-2',3'-O-(isopropylidine)-bicyclo[3.1.0]hexane (28): Nucleoside 27 (20 mg, 0.04 mmol) was dissolved in a mixture of MeOH and aqueous 2 M NaOH (3 mL, 2:1, v/v). 10% Pd/C (20 mg) and H$_2$ (3 bar) were added to this solution. After stirring the mixture for 19 h, the catalyst was removed by filtration through a Celite pad, which was washed with MeOH (40 mL), and the filtrate was evaporated to dryness. The resulting residue was purified by silica gel column chromatography (0-10% MeOH in EtOAc, v/v) to afford nucleoside 28 (15 mg, 79%) as white solid material. R$_f$=0.5 (15% MeOH in EtOAc, v/v); ESI-HRMS m/z 480.2385 ([M+H]$^+$, C$_{22}$H$_{34}$N$_5$O$_5$P.H$^+$: Calcd. 480.2376); $^1$H NMR (CDCl$_3$) δ 8.32 (s, 1H), 7.79 (s, 1H), 5.80 (s, 2H), 5.19 (d, 1H, J=7.2 Hz), 4.83 (s, 1H), 4.74 (d, 1H, J=7.2 Hz), 4.63-4.73 (m, 2H), 1.60-2.35 (m, 4H), 1.52 (s, 3H), 1.44-1.51 (m, 1H), 1.33 (s, 6H), 1.31 (s, 6H), 1.23 (s, 3H), 1.04-1.09 (m, 1H), 0.76-0.83 (m, 1H). $^{31}$P NMR (CDCl$_3$) δ0.04.

(1'S,2'R,3'S,4'R,5'S)-4'-(6-Aminopurin-9-yl)-2',3'-(dihydroxy)-1'-(phosphonoethenyl)-bicyclo[3.1.0]hexane (10): Nucleoside 28 (15 mg, 0.032 mmol) was coevaporated with anhydrous toluene (3×2 mL) and dissolved in anhydrous CH$_2$Cl$_2$ (2 mL). Iodotrimethylsilane (45 μl, 0.32 mmol) was added. After stirring for 15 h, the reaction mixture was cooled to 0° C. followed by the addition of ice-cold H$_2$O (15 mL) and CH$_2$Cl$_2$ (15 mL). The phases were separated, and the aqueous phase was washed with CH$_2$Cl$_2$ (1×25 mL) and diethyl ether (3×35 mL). The resulting aqueous phase was evaporated to dryness and purified by HPLC (retention time: 16.6 min) to afford 10 (6.7 mg, 47%) as a white solid material. ESI-HRMS m/z 354.0970 [M−H]$^-$, C$_{13}$H$_{17}$N$_5$O$_5$P$^-$: Calcd. 354.0967); $^1$H NMR (CDCl$_3$) δ 8.20 (s, 1H), 8.14 (s, 1H), 4.76 (s, 1H), 4.58 (d, 1H, J=6.1 Hz), 4.09 (d, 1H, J=6.1 Hz), 3.21 (q, 3H, J=7.2 Hz), 1.69-2.14 (m, 4H), 1.59-1.69 (m, 1H), 1.39-1.349 (m, 1H), 1.29 (t, 6H, J=7.2 Hz), 0.81-0.92 (m, 1H). $^{31}$P NMR (D$_2$O) δ 27.95. Purity >99% by HPLC (retention time: 2.91 min)

(1S,2R,3S,4S,5S)-1-Formyl-2,3-O-(isopropylidene)-4-O-(tert-butyldimethylsilyl)-bicyclo[3.1.0]hexane (29): Compound 15 (0.63 g, 1.43 mmol) was coevaporated with anhydrous toluene (2×25 mL) and dissolved in anhydrous CH$_2$Cl$_2$ (25 mL). Dess-Martin periodinane (0.91 g, 2.13 mmol) was added to this solution. After stirring for 4 h, the reaction mixture was diluted with EtOAc (50 mL) and washed with an aqueous mixture of Na$_2$S$_2$O$_3$ and NaHCO$_3$ (3×50 mL). The aqueous phase was extracted with EtOAc (2×50 mL). The combined organic phase was evaporated to dryness and the resulting residue was purified by silica gel column chromatography (0-25% EtOAc in petroleum ether, v/v) to afford aldehyde 29 (452 mg, 73%) as a colorless oil. R$_f$=0.6 (50% EtOAc in petroleum ether, v/v); ESI-HRMS m/z 459.1986 ([M+Na]$^+$, C$_{26}$H$_{32}$O$_4$Si.Na$^+$: Calcd. 459.1968); $^1$H NMR (CDCl$_3$) δ8.92 (s, 1H), 7.68-7.78 (m, 4H, Ph), 7.31-7.48 (m, 6H, Ph), 5.13 (d, 1H, J=6.5 Hz), 4.41 (t, 1H, J=6.5 Hz), 4.16

(t, 1H, J=6.5 Hz), 2.19-2.28 (m, 1H), 2.10-2.18 (m, 1H), 1.55 (s, 3H), 1.43-1.51 (m, 1H), 1.23 (s, 3H), 1.09 (s, 9H).

(1S,2R,3S,4S,5S)-1-[Diisopropyl-(E)-phosphonoethenyl]-2,3-O-(isopropylidene)-4-O-(tert-butyldimethylsilyl)-bicyclo[3.1.0]hexane (30): Tetraisopropyl methylenediphosphonate (475 μL, 1.47 mmol) was added to a suspension of sodium hydride (71 mg, 2.95 mmol, 60% dispersion in mineral oil) in anhydrous THF (6 mL) at 0° C. After $H_2$ evolution ceased, a solution of aldehyde 29 (0.43 g, 0.98 mmol) in anhydrous THF (4 mL) was added dropwise carefully at 0° C. After stirring at 0° C. for 1 h, the mixture was warmed to rt. After stirring at rt for 1 h, the mixture was cooled to 0° C., and ice-cold $H_2O$ (20 mL) was added. The phases were separated, and the aqueous phase was extracted with EtOAc (3×35 mL). The combined organic phase was evaporated to dryness and the resulting residue was purified by silica gel column chromatography (0-70% EtOAc in petroleum ether, v/v) to afford nucleoside 30 (0.24 mg, 48%) as a white solid material. $R_f$=0.4 (70% EtOAc in petroleum ether, v/v); ESI-HRMS m/z 599.2938 ([M+H]$^+$, $C_{33}H_{47}O_6PSi.H^+$: Calcd. 599.2958); $^1$H NMR (CDCl$_3$) δ 7.69-7.77 (m, 4H, Ph), 7.31-7.45 (m, 6H, Ph), 6.24-6.40 (m, 1H), 5.66 (t, 1H, J=17.5 Hz), 4.75 (d, 1H, J=6.5 Hz), 4.52-4.64 (m, 2H) 4.42 (t, 1H, J=6.5 Hz), 4.11 (t, 1H, J=6.5 Hz), 1.93-1.99 (m, 1H), 1.78-1.85 (m, 1H), 1.57 (s, 3H), 1.19-1.32 (m, 15H), 1.07 (s, 9H), 0.93-1.01 (m, 1H).

(1S,2R,3S,4S,5S)-1-[Diisopropyl-(E)-phosphonoethenyl]-4-(hydroxy)-2,3-O-(isopropylidene)-bicyclo[3.1.0] hexane (31): Compound 30 (0.45 g, 0.76 mmol) was dissolved in THF (10 mL) and tetrabutylammonium fluoride (1.0 M in THF, 2.3 mL, 2.3 mmol) was added. After stirring for 13 h, the reaction mixture was evaporated to dryness. The resulting residue was purified by silica gel column chromatography (0-7% MeOH in EtOAc, v/v) to afford compound 31 (0.26 g, 98%) as a colorless oil. $R_f$=0.3 (EtOAc); ESI-HRMS m/z 361.1790 ([M+H]$^+$, $C_{17}H_{29}O_6P.H^+$: Calcd. 361.1780); $^1$H NMR (CDCl$_3$) δ6.34-6.49 (m, 1H), 5.74 (t, 1H, J=17.5 Hz), 4.99 (d, 1H, J=6.5 Hz), 4.47-4.69 (m, 4H), 2.40 (d, 1H, J=9.5 Hz), 2.07-2.15 (M, 1H), 1.59-1.63 (m, 1H), 1.58 (s, 3H), 1.22-1.34 (m, 15H), 0.93-1.07 (m, 1H).

(1'S,2'R,3'S,4'R,5'S)-4'-(6-Chloropurin-9-yl)-1'-[diisopropyl-(E)-phosphonoethenyl]-2',3'-O-(isopropylidene)-bicyclo[3.1.0]hexane (32): Diisopropyl azodicarboxylate (90 μL, 0.45 mmol) was added at rt to a mixture of triphenylphosphine (117 mg, 0.45 mmol) and 6-chloropurine (70 mg, 0.45 mmol) in anhydrous THF (5 mL). After stirring for 30 min, a solution of the compound 31 (80 mg, 0.23 mmol) in THF (5 mL) was added. After stirring for 60 h, the reaction mixture was evaporated to dryness. The resulting residue was purified by silica gel column chromatography (0-55% acetone in petroleum ether, v/v) to afford nucleoside 32 (92 mg, 85%) as a white solid material. $R_f$=0.4 (60% acetone in petroleum ether, v/v); ESI-HRMS m/z 519.1532 ([M+Na]$^+$, $C_{22}H_{30}ClN_4O_5P.Na^+$: Calcd. 519.1540); $^1$H NMR (CDCl$_3$) δ 8.71 (s, 1H), 8.07 (s, 1H), 6.49-6.63 (m, 1H), 5.96 (t, 1H, J=17.5), 5.53 (d, 1H, J=6.5 Hz), 5.02 (s, 1H), 4.79 (d, 1H, J=6.5 Hz), 4.61-4.73 (m, 2H), 1.86-1.92 (m, 1H), 1.58-1.63 (m, 1H), 1.54 (s, 3H), 1.22-1.38 (m, 16H).

(1'S,2'R,3'S,4'R,5'S)-4'-(6-Aminopurin-9-yl)-1'-[diisopropyl-(E)-phosphonoethenyl]-2',3'-O-(isopropylidene)-bicyclo[3.1.0]hexane (33): Nucleoside 32 (90 mg, 0.19 mmol) was treated with 2 M NH$_3$ in i-PrOH (7 mL) and heated to 70° C. After stirring for 17 h, the reaction mixture was evaporated to dryness. The resulting residue was purified by silica gel column chromatography (0-12% MeOH in CH$_2$Cl$_2$, v/v) to afford nucleoside 33 (74 mg, 85%) as a white solid material. $R_f$=0.2 (10% MeOH in EtOAc, v/v); ESI-HRMS m/z 478.2198 ([M+H]$^+$, $C_{22}H_{32}N_5O_5P.H^+$: Calcd. 478.2219); $^1$H NMR (CDCl$_3$) δ 8.30 (s, 1H), 7.73 (s, 1H), 6.51-6.66 (m, 1H), 5.96 (t, 1H, J=17.5), 5.47-5.54 (m, 3H), 4.95 (s, 1H), 4.78 (d, 1H, J=6.5 Hz), 4.60-4.72 (m, 2H), 1.86-1.94 (m, 1H), 1.53-1.57 (m, 4H), 1.24-1.37 (m, 16H).

(1'S,2'R,3'S,4'R,5'S)-4'-(6-Aminopurin-9-yl)-2',3'-(dihydroxy)-1'-[(E)-phosphonoethenyl]-bicyclo[3.1.0]hexane (8): Nucleoside 33 (20 mg, 0.042 mmol) was coevaporated with anhydrous toluene (3×5 mL) and dissolved in anhydrous CH$_2$Cl$_2$ (5 mL). Iodotrimethylsilane (60 μl, 0.42 mmol) was added. After stirring for 17 h, the reaction mixture was cooled to 0° C., followed by the addition of ice-cold H$_2$O (25 mL) and CH$_2$Cl$_2$ (25 mL). The phases were separated and the aqueous phase was washed with CH$_2$Cl$_2$ (1×35 mL) and diethyl ether (3×35 mL). The resulting aqueous phase was evaporated to dryness and purified by HPLC (retention time: 16.5 min) to afford 8 (11.8 mg, 78%) as a white solid material. ESI-HRMS m/z 352.0821 [M–H]$^-$, $C_{13}H_{15}N_5O_5P^+$: Calcd. 352.0811); $^1$H NMR (D$_2$O) δ 8.30 (s, 1H), 8.06 (s, 1H), 6.30-6.44 (m, 1H), 6.07 (t, 1H, J=17.5), 4.97 (s, 1H), 4.89 (d, 1H, J=7.2 Hz), 4.09 (d, 1H, J=7.2 Hz), 3.21 (q, 3H, J=7.2 Hz), 2.03-2.10 (m, 2H), 1.84-1.89 (m, 1H), 1.29 (t, 7H, J=7.2 Hz). $^{31}$P NMR (D$_2$O) δ 15.71. Purity >99% by HPLC (retention time: 3.5 min)

(1S,2R,3S,4S,5S)-1-(Diisopropyl-phosphonoethenyl)-4-(hydroxy)-2,3-O-(isopropylidene)-bicyclo[3.1.0]hexane (34): Compound 31 (30 mg, 0.083 mmol) was dissolved in MeOH (3 mL). 10% Pd/C (25 mg) and H$_2$ (3 bar) was added. After stirring the mixture for 17 h, the catalyst was removed by filtration through a Celite pad, which was washed with MeOH (40 mL), and the filtrate was evaporated to dryness. The resulting residue was purified by silica gel column chromatography (0-90% acetone in petroleum ether, v/v) to afford nucleoside 34 (22 mg, 72%) as white solid material. $R_f$=0.3 (5% MeOH in EtOAc, v/v); ESI-HRMS m/z 363.1933 ([M+H]$^+$, $C_{17}H_{31}O_6P.H^+$: Calcd. 363.1937); $^1$H NMR (CDCl$_3$) δ 4.61-4.76 (m, 2H), 4.43-4.54 (m, 2H), 4.17-4.35 (m, 1H), 2.32 (d, J=9.8 Hz, 1H), 1.43-1.93 (m, 8H), 1.22-1.37 (m, 15H), 1.07-1.14 (m, 1H), 0.47-0.56 (m, 1H).

(1'S,2'R,3'S,4'R,5'S)-4'-(2,6-Dichloropurin-9-yl)-1'-(diisopropyl-phosphonoethenyl)-2',3'-O-(isopropylidene)-bicyclo[3.1.0]hexane (35): Diisopropyl azodicarboxylate (93 μL, 0.47 mmol) was added at rt to a mixture of triphenylphosphine (123 mg, 0.47 mmol) and 2,6-dichloropurine (89 mg, 0.47 mmol) in anhydrous THF (4 mL). After stirring for 30 min, a solution of the compound 34 (85 mg, 0.24 mmol) in THF (4 mL) was added. After stirring for 65 h, the reaction mixture was evaporated to dryness. The resulting residue was purified by silica gel column chromatography (0-5% MeOH in EtOAc, v/v) to afford nucleoside 35 (50 mg, 40%) as a white solid material. $R_f$=0.4 (5% MeOH in EtOAc, v/v); ESI-HRMS m/z 533.1497 ([M+H]$^+$, $C_{22}H_{31}Cl_2N_4O_5P.H^+$: Calcd. 533.1487); $^1$H NMR (CDCl$_3$) δ8.09 (s, 1H), 5.20 (d, 1H, J=7.2 Hz), 4.86 (s, 1H), 4.73 (d, 1H, J=7.2 Hz), 4.63-4.73 (m, 2H), 2.25-2.44 (m, 1H), 1.79-2.09 (m, 2H), 1.58-1.70 (m, 1H), 1.52 (s, 3H), 1.43-1.52 (m, 1H), 1.28-1.35 (m, 12H), 1.24 (s, 3H), 1.04-1.11 (m, 1H), 0.78-0.87 (m, 1H).

(1'S,2'R,3'S,4'R,5'S)-4'-(6-Amino-2-chloropurin-9-yl)-1'-(diisopropyl-phosphonoethenyl)-2',3'-O-(isopropylidene)-bicyclo[3.1.0]hexane (36): Nucleoside 35 (50 mg, 0.094 mmol) was treated with 2 M NH$_3$ in i-PrOH (5 mL) and heated to 70° C. After stirring for 19 h, the reaction mixture was evaporated to dryness. The resulting residue was purified by silica gel column chromatography (0-10% MeOH in CH$_2$Cl$_2$, v/v) to afford nucleoside 36 (34 mg, 71%) as a white solid material. $R_f$=0.4 (8% MeOH in EtOAc, v/v); ESI-HRMS m/z 514.1978 ([M+H]$^+$, $C_{22}H_{33}ClN_5O_5P.H^+$: Calcd. 514.1986); $^1$H NMR (CDCl$_3$) δ7.73 (s, 1H), 5.84 (s, 2H), 5.20

(d, 1H, J=6.5 Hz), 4.76 (s, 1H), 4.72 (d, 1H, J=6.5 Hz), 4.62-4.71 (m, 2H), 2.24-2.40 (m, 1H), 1.75-2.08 (m, 1H), 1.56-1.74 (m, 5H), 1.40-1.47 (m, 1H), 1.28-1.35 (m, 12H), 1.24 (s, 1H), 1.01-1.06 (m, 1H), 0.74-0.82 (m, 1H).

(1'S,2'R,3'S,4'R,5'S)-4-(6-Amino-2-chloropurin-9-yl)-2',3'-(dihydroxy)-1'-(phosphonoethenyl)-bicyclo[3.1.0]hexane (9): Nucleoside 23 (25 mg, 0.049 mmol) was coevaporated with anhydrous toluene (3×4 mL) and dissolved in anhydrous $CH_2Cl_2$ (4 mL). Iodotrimethylsilane (70 µl, 0.49 mmol) was added. After stirring for 19 h, the reaction mixture was cooled to 0° C. followed by the addition of ice-cold $H_2O$ (25 mL) and $CH_2Cl_2$ (25 mL). The phases were separated, and the aqueous phase was washed with $CH_2Cl_2$ (1×35 mL) and diethyl ether (3×35 mL). The resulting aqueous phase was evaporated to dryness and purified by HPLC (retention time: 21.5 min) to afford 9 (8.5 mg) and 10 (1.3 mg, 53%, combined yield) as a white solid materials. ESI-HRMS m/z 388.0574 [M−H]$^-$, $C_{13}H_{16}ClN_5O_5P^-$: Calcd. 388.0578); $^1$H NMR (D$_2$O) δ 8.15 (s, 1H), 4.74 (s, 1H), 4.61 (d, 1H, J=7.2 Hz), 4.11 (d, 1H, J=7.2 Hz), 3.21 (q, 3H, J=7.2 Hz), 1.70-2.11 (m, 4H), 1.63-1.71 (m, 1H), 1.33-1.38 (m, 1H), 1.29 (t, 3H, J=7.2 Hz), 0.81-0.91 (m, 1H). $^{31}$P NMR (D$_2$O) δ 28.26. Purity >99% by HPLC (retention time: 4.6 min)

(1S,2R,3S,4S,5S)-1-Bromomethyl-2,3-O-(isopropylidene)-4-O-(tert-butyldimethylsilyl)-bicyclo[3.1.0]hexane (37): Compound 15 (0.30 g, 0.69 mmol) was coevaporated with anhydrous toluene (3×10 mL) and dissolved in anhydrous $CH_2Cl_2$ (8 mL). CBr$_4$ (0.46 g, 1.36 mmol) triphenylphosphine (0.36 g, 1.36 mmol), and triethylamine (0.3 mL, 2.07 mmol) were added. After stirring for 17 h, the reaction mixture was diluted with $CH_2Cl_2$ (50 mL) and sat. aqueous NaCl (25 mL). The phases were separated and aqueous phase was extracted with $CH_2Cl_2$ (3×25 mL). The combined organic phase was evaporated to dryness and the resulting residue was purified by silica gel column chromatography (0-20% EtOAc in petroleum ether, v/v) to afford compound 37 (0.28 g, 81%) as a colorless oil. $R_f$=0.8 (50% EtOAc in petroleum ether, v/v); ESI-HRMS m/z 523.1296 ([M+Na]$^+$, $C_{26}H_{33}BrO_3Si.Na^+$: Calcd. 523.1280); $^1$H NMR (CDCl$_3$) δ 7.67.77 (m, 4H, Ph), 7.30-7.45 (m, 6H, Ph), 4.77 (d, 1H, J=6.5 Hz), 4.44 (t, 1H, J=6.5 Hz), 4.08 (t, 1H, J=6.5 Hz), 3.76 (d, 1H, J=10.5 Hz), 3.13 (d, 1H, J=10.5 Hz), 1.80-1.87 (m, 1H), 1.60-1.70 (m, 1H), 1.55 (s, 3H), 1.21 (s, 3H), 1.05 (s, 9H), 0.71-0.86 (m, 1H).

(1S,2R,3S,4S,5S)-1-C-(Ethoxymethylphosphinyl)-2,3-O-(isopropylidene)-4-O-(tert-butyldimethylsilyl)-bicyclo[3.1.0]hexane (38): Compound 37 (0.28 g, 0.56 mmol) was dissolved in diethylmethylphosphite (4 mL) and heated up to 110° C. After stirring for 17 h, the reaction mixture was cooled to rt and evaporated to dryness. The resulting residue was purified by silica gel column chromatography (0-90% EtOAc in petroleum ether, v/v) to afford inseparable diastereomeric mixture of compound 38 (0.28 g, 95%) as a colorless oil. $R_f$=0.6 (5% MeOH in EtOAc, v/v); ESI-HRMS m/z 529.2532 ([M+H]$^+$, $C_{29}H_{41}O_5PSi.H^+$: Calcd. 529.2539); $^1$H NMR (CDCl$_3$) δ 7.68-7.77 (m, 6.8H, Ph), 7.29-7.46 (m, 10.2H, Ph), 4.75 (d, 0.7H, J=6.5 Hz), 4.68 (d, 1H, J=6.5 Hz), 4.43-4.49 (m, 1.7H), 3.87-4.14 (m, 5.1H), 1.73-1.92 (m, 3.4H), 1.62 (s, 5.1H), 1.57-1.60 (m, 1.7H), 1.48 (d, 3H, J=3.4 Hz), 1.44 (d, 2.1H, J=3.4 Hz), 1.26 (t, 3H, J=7.2 Hz), 1.22 (t, 2.1H, J=7.2 Hz), 1.19 (s, 2.1H), 1.18 (s, 3H), 1.09-1.13 (m, 1.7H), 1.07 (s, 15.3H), 0.52-0.69 (m, 1H).

(1S,2R,3S,4S,5S)-1-C-(Ethoxymethylphosphinyl)-4-hydroxy-2,3-O-(isopropylidene)-bicyclo[3.1.0]hexane (39): Compound 38 (0.30 g, 0.57 mmol) was dissolved in THF (10 mL) and tetrabutylammonium fluoride (1.0 M in THF, 1.70 mL, 1.70 mmol) was added. After stirring for 21 h, the reaction mixture was evaporated to dryness. The resulting residue was purified by silica gel column chromatography (0-15% MeOH in EtOAc, v/v) to afford an inseparable diastereomeric mixture of compound 39 (0.15 g, 91%) as a colorless oil. $R_f$=0.2 (15% MeOH in $CH_2Cl_2$, v/v); ESI-HRMS m/z 291.1366 ([M+H]$^+$, $C_{13}H_{23}O_5P.H^+$: Calcd. 291.1361); $^1$H NMR (CDCl$_3$) δ 4.89-5.03 (m, 2H), 4.50-4.60 (m, 4H), 3.97-4.14 (m, 4H), 2.34-2.40 (m, 2H), 1.95 (t, 2H, J=7.7 Hz), 1.90 (t, 2H, J=7.7 Hz), 1.78-1.87 (m, 2H), 1.66 (s, 6H), 1.55 (d, 3H, J=3.9 Hz), 1.50 (d, 3H, J=3.9 Hz), 1.29-1.35 (m, 6H), 1.28 (s, 6H), 1.23-1.26 (m, 2H), 0.60-0.71 (m, 2H).

(1'S,2'R,3'S,4'R,5'S)-1'-C-(Ethoxymethylphosphinyl)-4'-(2,6-dichloropurin-9-yl)-2',3'-O-(isopropylidene)-bicyclo[3.1.0]hexane (40): Diisopropyl azodicarboxylate (360 µL, 1.82 mmol) was added at rt to a mixture of triphenylphosphine (0.48 g, 1.82 mmol) and 2,6-dichloropurine (0.35 g, 1.82 mmol) in anhydrous THF (5 mL). After stirring for 30 min, a solution of the compound 39 (0.27 g, 0.91 mmol) in THF (5 mL) was added. After stirring for 60 h, the reaction mixture was evaporated to dryness. The resulting residue was purified by silica gel column chromatography (0-10% MeOH in EtOAc, v/v) to afford inseparable diastereomeric mixture of nucleoside 40 (0.25 mg, 60%) as a white solid material. $R_f$=0.2 (10% MeOH in EtOAc, v/v); ESI-HRMS m/z 461.0899 ([M+H]$^+$, $C_{18}H_{23}Cl_2N_4O_4P.H^+$: Calcd. 461.0912); $^1$H NMR (CDCl$_3$) δ 8.79 (s, 0.5H), 8.51 (s, 1H), 5.45 (d, 0.5H, J=7.2 Hz), 5.32 (d, 1H, J=7.2 Hz), 5.06 (s, 0.5H), 4.96 (s, 1H), 4.66 (d, 1.5H, J=7.2 Hz), 3.98-4.21 (m, 3H), 2.40-2.51 (m, 0.5H), 2.15-2.24 (m, 1H), 1.93-2.11 (m, 1.5H), 1.63-1.75 (m, 0.5H), 1.61 (s, 5.5H), 1.59 (d, 3H, J=3.9 Hz), 1.55 (d, 1.5H, J=3.9 Hz), 1.35 (t, 3H, J=7.2 Hz), 1.25 (t, 1.5H, J=7.2 Hz), 1.24 (s, 4.5H), 1.18-1.23 (m, 1.5H), 0.95-1.13 (m, 1.5H).

(1'S,2'R,3'S,4'R,5'S)-4'-(6-Amino-2-chloropurin-9-yl)-1'-C-(ethoxymethylphosphinyl)-2',3'-O-(isopropylidene)-bicyclo[3.1.0]hexane (41): Nucleoside 40 (0.20 g, 0.44 mmol) was treated with 2M NH$_3$ in i-PrOH (8 mL) and heated to 70° C. After stirring for 15 h, the reaction mixture was evaporated to dryness. The resulting residue was purified by silica gel column chromatography (0-7% MeOH in $CH_2Cl_2$, v/v) to afford nucleoside 41 (150 mg, 79%) as a white solid material. $R_f$=0.4 (10% MeOH in $CH_2Cl_2$, v/v); ESI-HRMS m/z 442.1416 ([M+H]$^+$, $C_{18}H_{26}ClN_5O_4P.H^+$: Calcd. 442.1411); $^1$H NMR (CDCl$_3$) δ 8.21 (s, 0.5H), 8.00 (s, 1H), 5.96 (s, 3H), 5.40 (d, 0.5H, J=6.5 Hz), 5.30 (d, 1H, J=6.5 Hz), 4.91 (s, 0.5H), 4.81 (s, 1H), 4.62-4.71 (d, 1.5H, J=7.2 Hz), 4.10-4.22 (m, 2H), 3.98-4.09 (m, 1H), 3.60-3.80 (m, 1H), 2.64 (t, 1H, J=15.3 Hz), 2.35 (t, 0.5H, J=15.3 Hz), 2.01-2.17 (m, 0.5H), 1.87 (t, 1.5H, J=15.8 Hz), 1.75 (s, 4.5H), 1.55-1.69 (m, 4.5H), 1.36 (t, 3H, J=7.2 Hz), 1.25 (t, 1.5H, J=7.2 Hz), 1.24 (s, 4.5H), 1.17-1.22 (m, 1.5H), 0.96-1.07 (m, 1.5H).

(1'S,2'R,3'S,4'R,5'S)-4'-(6-Amino-2-chloropurin-9-yl)-2',3'-dihydroxy-1'-(methylphosphonicacid)-bicyclo[3.1.0]hexane (11) and (1'S,2'R,3'S,4'R,5' S)-4'-(6-Aminopurin-9-yl)-2',3'-dihydroxy-1'-(methylphosphonicacid)-bicyclo[3.1.0]hexane (12): Nucleoside 29 (15 mg, 0.034 mmol) was coevaporated with anhydrous toluene (3×3 mL) and dissolved in anhydrous $CH_2Cl_2$ (4 mL). Iodotrimethylsilane (91 µl, 0.33 mmol) was added. After stirring for 19 h, the reaction mixture was cooled to 0° C., followed by the addition of ice-cold $H_2O$ (25 mL) and $CH_2Cl_2$ (25 mL). The phases were separated and the aqueous phase was washed with $CH_2Cl_2$ (1×35 mL) and diethyl ether (3×35 mL). The resulting aqueous phase was evaporated to dryness and purified by HPLC (retention time: 16.8 min) to afford 11 (1.3 mg, 11%) and 12 (0.8 mg, 20%, combined yield) as a white solid material.

Analytical data of compound 11: ESI-HRMS m/z 372.0625 [M−H]$^-$, $C_{13}H_{16}ClN_5O_4P^-$: Calcd. 372.0628); $^1$H NMR (D$_2$O) δ 8.23 (s, 1H), 4.76-4.79 (m, 1H), 4.63 (d, 1H, J=6.2 Hz), 4.12 (d, 1H, J=6.2 Hz), 3.21 (q, 2H, J=7.2 Hz), 2.34 (t, 1H, J=15.3 Hz), 1.75-1.86 (m, 1H), 1.68-1.75 (m, 1H), 1.51-1.56 (m, 1H) 1.35 (d, 3H, J=13.2 Hz), 1.26 (t, 1H, J=7.2 Hz) 0.96-1.04 (m, 1H). $^{31}$P NMR (D$_2$O) δ 46.01. Purity >99% by HPLC (retention time: 4.19 min).

Analytical data of compound 12: ESI-HRMS m/z 338.1016 [M–H]$^-$, C$_{13}$H$_{17}$N$_5$O$_4$P$^-$: Calcd. 338.1018); $^1$H NMR (D$_2$O) δ 8.26 (s, 1H), 8.25 (s, 1H), 4.76-4.79 (m, 1H), 4.63 (d, 1H, J=6.2 Hz), 4.12 (d, 1H, J=6.2 Hz), 3.21 (q, 2H, J=7.2 Hz), 2.34 (t, 1H, J=15.3 Hz), 1.75-1.86 (m, 1H), 1.68-1.75 (m, 1H), 1.51-1.56 (m, 1H) 1.35 (d, 3H, J=13.2 Hz), 1.26 (t, 1H, J=7.2 Hz) 0.96-1.04 (m, 1H). $^{31}$P NMR (D$_2$O) δ 46.0. Purity >99% by HPLC (retention time: 5.91 min).

Experimental Procedures for Example 3

General methods: Compound 13a was either synthesized as reported or obtained as a custom synthesis from Natland International Corporation (Research Triangle Park, N.C.). All other reagents and solvents (regular and anhydrous) were of analytical grade and obtained from commercial suppliers and used without further purification. Reactions were conducted under an atmosphere of argon whenever anhydrous solvents were used. All reactions were monitored by thin-layer chromatography (TLC) using silica gel coated plates with a fluorescence indicator which were visualized: a) under UV light, b) by dipping in 5% conc. H$_2$SO$_4$ in absolute ethanol (v/v) followed by heating, or c) by dipping in a solution of anisaldehyde:H$_2$SO$_4$ (1:2, v/v) in MeOH followed by heating. Silica gel column chromatography was performed with silica gel (SiO$_2$, 200-400 mesh, 60 Å) using moderate air pressure. Evaporation of solvents was carried out under reduced pressure at a temperature below 50° C. After column chromatography, appropriate fractions were pooled, evaporated and dried at high vacuum for at least 12 h to give the obtained products in high purity. $^1$H NMR and $^{31}$P NMR ascertained sample purity. No corrections in yields were made for solvent of crystallization. $^1$H NMR and $^{31}$P NMR spectra were recorded at 300 MHz and 121.5 MHz, respectively. Chemical shifts are reported in parts per million (ppm) relative to tetramethylsilane or deuterated solvent as the internal standard ($^2$H: CDCl$_3$ 7.26 ppm). Systematic compound names for bicyclic nucleosides are given according to the von Baeyer nomenclature. High resolution mass spectroscopic (HRMS) measurements were performed on a proteomics optimized Q-TOF-2 (Micromass-Waters) using external calibration with polyalanine. Observed mass accuracies are those expected on the basis of known performance of the instrument as well as the trends in masses of standard compounds observed at intervals during the series of measurements. Reported masses are observed masses uncorrected for this time-dependent drift in mass accuracy.

Purification of the nucleotide derivatives for biological testing was performed by HPLC with a Luna 5 micron RP-C18 semipreparative column (250×10.0 mm; Phenomenex, Torrance, Calif.) under the following conditions: flow rate of 2 mL/min; 10 mM triethylammonium acetate (TEAA)-CH$_3$CN from 100:0 (v/v) to 70:30 (v/v) in 30 min and isolated in the triethylammonium salt form. Analytical purity of compounds was checked using a Hewlett-Packard 1100 HPLC equipped with Zorbax SB-Aq 5 μm analytical column (50×4.6 mm; Agilent Technologies Inc, Palo Alto, Calif.). Mobile phase: linear gradient solvent system: 5 mM TBAP (tetrabutylammonium dihydrogenphosphate)-CH$_3$CN from 80:20 to 40:60 in 13 min; the flow rate was 0.5 mL/min. Peaks were detected by UV absorption with a diode array detector at 254, 275, and 280 nm. All derivatives tested for biological activity showed >99% purity by HPLC analysis (detection at 254 nm).

(1'S,2'R,3'S,4'R,5'S)-4-(6-amino-2-chloro-purin-9-yl)-2,3-(dihydroxyl)-1-[hydroxymethyl]bicyclo-[3.1.0]hexane (19a). Nucleoside 18a (25 mg, 0.071 mmol) was dissolved in 10% aqueous trifluoroacetic acid (1.5 mL, v/v). After stirring at room temperature for 17 h, the reaction mixture was evaporated to dryness. The resulting residue was purified by silica gel column chromatography (0-12% MeOH in CH$_2$Cl$_2$, v/v) to afford 2',3',5'-trihydroxy nucleoside 19a (15.2 mg, 69%). R$_f$=0.3 (20% MeOH in CH$_2$Cl$_2$, v/v). $^1$H NMR (MeOD-d$_4$) δ 8.48 (s, 1H), 4.80 (s, 1H), 4.76 (d, J=7.1 Hz, 1H), 4.23-4.28 (d, J=11.5 Hz, 1H), 3.87 (d, J=7.1 Hz, 1H), 3.35 (s, 1H), 1.58-1.63 (m, 1H), 1.50-1.55 (m, 1H), 0.72-0.78 (m, 1H).

(1'S,2'R,3'S,4'R,5'S)-4-(6-amino-2-chloro-purin-9-yl)-1-[iodomethyl]-2,3-(O-isopropylidine) bicyclo-[3.1.0]hexane (20a). Nucleoside 18a (45 mg, 0.128 mmol) was coevaporated with anhydrous toluene (3×10 mL) and dissolved in anhydrous THF (3 mL). I$_2$ (66 mg, 0.256 mmol), triphenylphosphine (68 mg, 0.256 mmol), and imidazole (18 mg, 0.256 mmol) were added. After stirring for 17 h, the reaction mixture was diluted with EtOAc (30 mL) and washed with saturated aqueous Na$_2$S$_2$O$_3$ (2×15 mL). The phases were separated and aqueous phase was extracted with EtOAc (3×25 mL). The combined organic phase was evaporated to dryness, and the resulting residue was purified by silica gel column chromatography (0-80% EtOAc in petroleum ether, v/v) to afford 5'-iodo nucleoside 20a (41 mg, 74%). R$_f$=0.4 (5% MeOH in CH$_2$Cl$_2$, v/v). ESI-HRMS m/z 462.0205 ([M+H]$^+$ (C$_{15}$H$_{18}$N$_5$O$_2$Cl, calcd 462.0194). $^1$H NMR (CDCl$_3$) δ 8.09 (s, 1H), 5.91 (s, 2H), 5.32 (d, 1H, J=7.2 Hz), 4.91 (s, 1H), 5.32 (d, 1H, J=7.2 Hz), 3.63-3.69 (d, 1H, J=10.5 Hz), 3.53-3.56 (d, 1H, J=10.5 Hz), 1.65-1.74 (m, 1H), 1.71 (s, 3H), 1.29 (s, 3H), 1.22-1.31 (m, 1H), 1.10-1.15 (m, 1H).

(1'S,2'R,3'S,4'R,5'S)-4-(6-amino-2-chloro-purin-9-yl)-2,3-(dihydroxy)-1-[iodomethyl]bicyclo-[3.1.0]hexane (21a). 5-Iodo nucleoside 20a (106 mg, 0.229 mmol) was dissolved in THF (1 mL), followed by the addition of 10% aqueous trifluoroacetic acid (3.5 mL, v/v). After stirring the reaction mixture at 65° C. for 15 h, the reaction mixture was evaporated to dryness and the resulting residue was purified by silica gel column chromatography (0-80% EtOAc in petroleum ether, v/v) to afford 2',3'-dihydroxy-5'-iodo nucleoside 21a (41 mg, 60%). R$_f$=0.3 (10% MeOH in CH$_2$Cl$_2$, v/v). ESI-HRMS m/z 421.9883 ([M+H]$^+$ (C$_{12}$H$_{14}$N$_5$O$_2$ClI, calcd 421.9881). $^1$H NMR (MeOD-d$_4$) δ 8.41 (s, 1H), 4.75 (dd, 1H, J=1.8 Hz), 4.10 (dt, 1H, J=8 Hz, 2.8 Hz), 3.87-3.91 (d, 1H, J=10.5 Hz), 3.46-3.52 (d, 1H, J=10.5 Hz), 1.91-1.95 (m, 1H), 1.67-1.72 (m, 1H), 1.04-1.09 (m, 1H).

(1'S,2'R,3'S,4'R,5'S)-4-(6-amino-2-chloro-purin-9-yl)-2,3-(dihydroxy)-1-[monophosphorothioate]-bicyclo-[3.1.0]hexane (12a). To the suspension of 5'-iodo nucleoside 21a (3 mg, 7.12 μmol) and H$_2$O (0.5 mL), trisodium thiophosphate (10 mg, 55 μmol) was added. After stirring the reaction mixture for 3 d at room temperature under argon atmosphere, the reaction mixture was lyophilized and purified by semi preparative HPLC (retention time 19.5 min) to get 5'-monophosphorothioate 12a (1.65 mg, 57%) as a white solid. ESI-HRMS m/z 406.0159 ([M+H]$^+$ (C$_{19}$H$_9$N$_5$O$_2$SCl, calcd 406.0165). $^1$H NMR (D$_2$O) δ 8.39 (s, 1H), 4.62 (s, 1H), 4.63 (s, 1H), 3.97 (d, 1H, J=6.5 Hz), 3.19-3.26 (m, 1H), 2.79-2.87 (m, 1H), 1.69-1.74 (m, 1H), 1.39-1.43 (m, 1H), 0.84-0.90 (m, 1H).

Ethyl (1'S,2'R'3'S,4'R,5'S)-4-(6-amino-2-chloropurin-9-yl]-2',3'-O-(isopropylidene)-bicyclo[3.1.0]hexanecarboxylate (23a). Nucleoside 22a (53 mg, 0.13 mmol) was treated with 2 M NH$_3$ in i-PrOH (5 mL) and heated to 70° C. After stirring the reaction for 16 h, the reaction mixture was evaporated to dryness. The resulting residue purified by silica gel column chromatography (0-4% MeOH in $CH_2Cl_2$, v/v) to afford nucleoside 23a (35 mg, 68%) as a white solid. $R_f$=0.4 (5% MeoH in $CH_2Cl_2$, v/v). ESI-HRMS m/z 394.1286 ([M+H]$^+$ ($C_{17}H_{21}N_5O_4Cl$, calcd 394.1282). $^1$H NMR (MeOD-$d_4$) δ 8.09 (s, 1H), 5.85 (d, 1H, J=7.1 Hz), 4.98 (s, 1H), 4.81 (d, 1H, J=7.1 Hz), 4.20-4.26 (m, 1H), 2.23-2.28 (m, 1H), 1.64-1.67 (m, 1H), 1.52 (s, 3H), 1.34 (t, 3H, J=7.2 Hz), 1.20-1.29 (m, 4H).

(1'S,2'R,3'S,4'R,5'S)-4-(6-amino-2-chloro-purin-9-yl)-1-[hydroxydeuteromethyl]-2,3-(O-isopropylidine)bicyclo-[3.1.0]hexane (24a). Nucleoside 23a (9 mg, 23 μmol) was coevaporated with anhydrous toluene (3×10 mL), and dissolved in anhydrous THF (10 mL). LiBD$_4$ (3 mg, 115 μmol) was added and after stirring the reaction mixture for 4 h at 70° C., it was cooled to room temperature and quenched with a slow addition of MeOH (3 mL). The resulting reaction mixture was evaporated to dryness, and purified by silica gel column chromatography (0-8% MeOH in $CH_2Cl_2$, v/v) to afford nucleoside 24a (6 mg, 72%) as a white solid. $R_f$=0.4 (10% MeOH in $CH_2Cl_2$, v/v). ESI-HRMS m/z 421.9883 ([M+H]$^+$ ($C_{12}H_{14}N_5O_2ClI$, calcd 421.9881). $^1$H NMR (CDCl$_3$) δ 7.82 (s, 1H), 5.92 (s, 2H), 5.60 (d, 1H, J=6.4 Hz), 4.78 (s, 1H), 4.68 (d, 1H, J=7.2 Hz), 1.71-1.77 (m, 1H), 1.55 (s, 3H), 1.27 (s, 3H), 1.10-1.15 (m, 1H), 0.98-1.02 (m, 1H).

(1'S,2'R,3'S,4'R,5'S)-4-(6-Amino-2-chloro-9H-purin-9-yl)-2,3-(O-isopropylidene)-1-[(di-tert-butylphosphate)dideuteromethyl]bicyclo[3.1.0]hexane (26a). Nucleoside 24a (6 mg, 17 μmol) was coevaporated with anhydrous toluene (3×10 mL), and dissolved in anhydrous THF (1 mL). Di-t-butyl-N,N'-diethylphosphoramidite (24 μL, 85 μmol) and tetrazole (12 mg, 169 μmol) were added. After stirring at rt for 4 h, the reaction mixture was cooled to −70° C. followed by the addition of m-chloroperbenzoic acid (25 mg, 77%). The reaction mixture was warmed to 0° C. and allowed to stir for 15 min, followed by the addition of triethylamine (0.5 mL). The reaction mixture was evaporated to dryness, and the resulting crude residue was purified by silica gel column chromatography (0-4% MeOH in $CH_2Cl_2$, v/v) to afford nucleoside 26a (7 mg, 76%) as a white solid. $R_f$=0.3 (5% MeOH in $CH_2Cl_2$, v/v); ESI-HRMS m/z 546.2234 ([M+H]$^+$ ($C_{23}H_{34}D_2N_5O_6Cl$, calcd 546.2217). $^1$H NMR (MeOD-$d_4$) δ 8.15 (s, 1H), 5.34 (d, 1H, J=6.8 Hz), 4.98 (s, 1H), 4.77 (d, 1H, J=7.2 Hz), 1.74-1.77 (m, 1H), 1.48-1.55 (m, 21H), 1.25 (s, 3H), 1.21-1.24 (m, 1H), 1.09-1.13 (m, 1H).

(1'S,2'R,3'S,4'R,5'S)-4-(6-Amino-2-chloro-9H-purin-9-yl)-1-[phosphoryloxydideuteromethyl]-2,3-diol-bicyclo[3.1.0]hexane (6a). To a solution containing nucleoside 26a (7 mg, 12.8 μmol) in MeOH and $H_2O$ (2 mL, 1:1, v/v) was added Dowex-50 resin (~50 mg). The mixture was stirred for 3 h at 70° C. and the resin removed by filtration. The filtrate was then treated with 1 M triethylammonium bicarbonate buffer (1 mL) and evaporated to dryness. The resulting mixture was purified by semi preparative HPLC (retention time 16.5 min) to get 5'-monophosphate 6a (1.62 mg, 32%) as white solid. ESI-HRMS m/z 392.0493 ([M−H]$^+$ ($C_{12}H_{12}D_2N_5O_6ClP$, calcd 392.0496). $^1$H NMR (D$_2$O) δ 8.45 (s, 1H), 4.73 (s, 1H), 3.97 (d, 1H, J=6.5 Hz), 1.72-1.77 (m, 1H), 1.39-1.43 (m, 1H), 0.84-0.90 (m, 1H). $^{31}$P NMR (D$_2$O) δ 2.48.

Diethyl-(1'S,2'R,3'S,4'R,5'S)-4'-(6-chloro-2-iodo-purin-9-yl)-2',3'-O-(isopropylidene)-bicyclo[3.1.0]hexane phosphonate (28a). Diisopropyl azodicarboxylate (86 μL, 0.44 mmol) was added at rt to a mixture of triphenylphosphine (115 mg, 0.44 mmol) and 6-chloro-2-iodopurine (122 mg, 0.44 mmol) in anhydrous THF (4 mL). After stirring for 45 min, a solution of the compound 27a (70 mg, 0.22 mmol) in THF (4 mL) was added to the mixture. After stirring for 36 h, the reaction mixture was evaporated to dryness. The resulting residue was purified by silica gel column chromatography (0-3% MeOH in $CH_2Cl_2$, v/v) to afford nucleoside 28a (89 mg, 70%) as a white solid. $R_f$=0.5 (5% MeOH in $CH_2Cl_2$, v/v); ESI-HRMS m/z 583.0374 [M+H]$^+$, $C_{19}H_{25}ClIN_4O_5P.H^+$: Calcd. 583.0373); $^1$H NMR (CDCl$_3$) δ 8.64 (s, 1H), 5.39 (d, 1H, J=7.5 Hz), 5.07 (s, 1H), 4.64 (d, 1H, J=7.5 Hz), 4.15-4.21 (m, 4H), 2.41 (t, 1H, J=16.0 Hz), 2.11-2.22 (m, 1H), 1.73-1.79 (m, 1H), 1.59-1.64 (m, 1H), 1.54 (s, 3H), 1.35 (t, 3H, J=7.1 Hz), 1.28 (t, 3H, J=7.1 Hz), 1.25 (s, 3H), 1.04-1.09 (m, 1H).

Diethyl-(1'S,2'R,3'S,4'R,5'S)-4'-(6-amino-2-iodopurin-9-yl)-2',3'-O-(isopropylidene)-bicyclo[3.1.0]hexane phosphonate (29a). Nucleoside 28a (80 mg, 0.14 mmol) was treated with 2M NH$_3$ in i-PrOH (8 mL) and the mixture was heated to 70° C. and stirred for 17 h. The reaction mixture was evaporated to dryness, and the resulting residue was purified by silica gel column chromatography (0-6% MeOH in $CH_2Cl_2$, v/v) to afford nucleoside 29a (48 mg, 64%) as a white solid. $R_f$=0.4 (7% MeOH in $CH_2Cl_2$, v/v); ESI-HRMS m/z 564.0873 [M+H]$^+$, $C_{19}H_{27}IN_5O_5P.H^+$: Calcd. 564.0856); $^1$H NMR (CDCl$_3$) δ 8.15 (s, 1H), 5.74 (s, 2H), 5.34 (d, 1H, J=6.1 Hz), 4.94 (s, 1H), 4.64 (d, 1H, J=6.1 Hz), 4.12-4.19 (m, 4H), 2.19-2.42 (m, 2H), 1.69-1.74 (m, 1H), 1.55 (s, 3H), 1.33 (t, 3H, J=7.1 Hz), 1.26 (t, 3H, J=7.1 Hz), 1.22 (s, 3H), 1.18-1.21 (m, 1H), 1.03-1.09 (m, 1H).

(1'S,2'R,3'S,4'R,5'S)-4'-(6-Amino-2-iodoropurin-9-yl)-2',3'-(dihydroxy)-1'-(phosphonomethylene)-bicyclo[3.1.0]hexane (7a). Nucleoside 29a (10 mg, 0.017 mmol) was coevaporated with anhydrous toluene (3×3 mL) and dissolved in anhydrous $CH_2Cl_2$ (2 mL). To this solution was added iodotrimethylsilane (25 μl, 0.17 mmol). After stirring for 17 h, the reaction mixture was cooled to 0° C., followed by the addition of ice-cold $H_2O$ (20 mL) and $CH_2Cl_2$ (25 mL). The phases were separated and the aqueous phase washed with $CH_2Cl_2$ (2×35 mL) and diethyl ether (4×35 mL). The resulting aqueous phase was evaporated to dryness and purified by HPLC (retention time: 20 min) to afford 7a (4.1 mg, 49%) as a white solid. ESI-HRMS m/z 465.9777 [M−H]$^-$, $C_{12}H_{14}IN_5O_5P^-$: Calcd. 465.9771); $^1$H NMR (D$_2$O) δ8.19 (s, 1H), 4.71 (s, 1H), 4.58 (d, 1H, J=5.8 Hz), 3.98 (d, 1H, J=5.8 Hz), 3.13 (q, 4H, J=7.2 Hz), 2.17 (t, 1H, 15.5 Hz), 1.90 (t, 1H, 15.5 Hz), 1.68-1.74 (m, 1H), 1.35-1.42 (m, 1H), 1.21 (t, 6H, J=7.2 Hz), 0.88-0.94 (m, 1H). $^{31}$P NMR (D$_2$O) δ 25.39. Purity >99% by HPLC (retention time: 5.9 min).

Diethyl-(1'S,2'R,3'S,4'R,5'S)-4'-(6-amino-2-iodopurin-9-yl)-2',3'-(dihydroxy)-bicyclo[3.1.0]hexane phosphonate (16a). To a solution containing 29a (6 mg, 11.2 μmol) in MeOH:$H_2O$ (2 mL, 1:1, v/v) was added Dowex-50 resin (~50 Mg). The mixture was stirred for 3 h at 70° C. and the resin removed by filtration. Filtrate was evaporated to dryness and resulting crude purified by silica gel column chromatography (0-8% MeOH in $CH_2Cl_2$, v/v) to afford nucleoside 16a (4.5 mg, 49%) as a white solid. $R_f$=0.2 (5% MeOH in $CH_2Cl_2$, v/v); ESI-HRMS m/z 524.0562[M+H]$^+$, $C_{16}H_{24}IN_5O_5P.H^+$: Calcd. 524.0560); $^1$H NMR (MeOD-$d_4$) δ 8.25 (s, 1H), 4.77-4.81 (m, 2H), 4.10-4.19 (m, 4H), 3.98 (d, 1H, J=6.8 Hz), 2.35-2.52 (m, 1H), 1.68-1.73 (m, 1H), 1.49-1.52 (m, 1H), 1.29-1.35 (m, 6H), 0.85-0.91 (m, 1H).

Diethyl-(1'S,2'R,3'S,4'R,5'S)-4'-(6-amino-2-chloropurin-9-yl)-2',3'-(hydroxy)-bicyclo[3.1.0]hexane phosphonate (9a). To a solution containing 30a (25 Mg, 0.053 mmol) in MeOH (3 mL) and water (3 mL) was added Dowex-50 resin (~100 mg). The mixture was stirred for 3 h at 70° C. and the resin removed by filtration. The filtrate was evaporated to dryness and resulting crude purified by silica gel column chromatography (10% MeOH in EtOAc, v/v) to afford nucleoside 9a (8.3 mg, 40%) as a white solid. $R_f$=0.4 (10% MeOH in $CH_2Cl_2$, v/v); ESI-HRMS m/z 432.1197 [M+H]$^+$, $C_{16}H_{23}ClN_5O_5P.H^+$: Calcd. 432.1204); $^1$H NMR (CDCl$_3$) δ 8.31 (s, 1H), 4.73-4.79 (m, 2H), 4.06-4.18 (m, 4H), 3.98 (d, J=6.6 Hz), 2.23-2.54 (m, 1H), 1.92-2.03 (m, 1H), 1.72-1.78 (m, 1H), 1.51-1.57 (m, 1H), 1.28-1.35 (m, 6H), 0.80-0.89 (m, 1H).

(1'S,2'R,3'S,4'R,5'S)-4'-(6-Amino-2-chloropurin-9-yl)-1'-[diisopropyl-(E)-ethenylphosphonate]-2,3-(dihydroxy)-bicyclo-[3.1.0]-hexane (11a). To a solution containing 38a (10 mg, 19.5 μmol) in MeOH:H$_2$O (4 mL, 1:1, v/v) was added Dowex-50 resin (~50 mg). The mixture was stirred for 3 h at 70° C. and the resin removed by filtration. The filtrate was evaporated to dryness and resulting crude purified by silica gel column chromatography (0-10% MeOH in CH$_2$Cl$_2$, v/v) to afford nucleoside 11a (4.5 mg, 49%) as a white solid. $R_f$=0.3 (10% MeOH in CH$_2$Cl$_2$, v/v); ESI-HRMS m/z 474.1679 [M+H]$^+$, $C_{19}H_{30}ClN_5O_5P.H^+$: Calcd. 474.1673); $^1$H NMR (MeOD-d$_4$) δ 8.06 (s, 1H), 4.76 (d, 1H, J=6.9 Hz), 4.65-4.71 (m, 3H), 4.07 (d, 1H, J=6.9 Hz), 3.67-3.72 (m, 1H), 3.55-3.59 (m, 1H), 2.10-2.16 (m, 1H), 1.80-2.03 (m, 1H), 1.47-1.52 (m, 1H), 1.28-1.41 (m, 13H), 0.66-0.72 (m, 1H).

Experimental Protocols for Biological Evaluation

CSQ mice and compound administration: Mice displaying the CSQ model of severe cardiomyopathy and heart failure were bred and maintained according to a previously described method. The CSQ transgenic (TG) mice were originally provided by Dr. Larry Jones and developed hypertrophy followed by a lethal heart failure phenotype with death near the age of 3 months.

Compound 3 and its analogues were dissolved in phosphate-buffered saline, pH=7.4 at 3.3 μM (200 μL total volume), filtered for sterility for in vivo administration at 6 μL per day for 28 days via a mini-osmotic pump (Alzet) in the CSQ mice. Intact heart function in vivo was assessed by echocardiography following infusion of nucleotide- or vehicle Mouse echocardiography: Transthoracic echocardiography was performed using a linear 30-MHz transducer according to manufacturer's instructions (Vevo 660 High Resolution Imaging System from VisualSonics, Toronto, Canada) similar to previously described methods. Two dimensional-targeted M-mode echocardiographic measurements were carried out at mid-papillary muscle level. Mice were anesthetized with 1% isoflurane using a vaporizer as previously described. Left ventricular end-diastolic (LVEDD) and end-systolic (LVESD) diameters, and FS (defined as LVEDD-LVESD/LVEDD) were measured. Parameters were measured digitally on the M-mode tracings and were averaged from more than 3 cardiac cycles.

Activation of human P2Y$_1$ receptors: Activity at the hP2Y$_1$ receptor was quantified in 1321N1 human astrocytoma cells stably expressing this receptor, obtained from Prof T. K. Harden, University of North Carolina School of Medicine, Chapel Hill, N.C. The procedure for measuring intracellular calcium using a FLIPR in response to nucleotide derivatives has been described. Cells were grown overnight in 100 ml of medium in 96-well flatbottom plates at 37° C. at 5% CO$_2$ or until they reached ~80% confluency. The calcium-4 assay kit (Molecular Devices, Sunnyvale, Calif.) was used as directed with no washing of cells. Cells were loaded with 40 mL dye with probenecid in each well and incubated for 1 h at rt. The compound plate was prepared with dilutions of various compounds in Hank's Buffer at pH 7.2. Samples were run in duplicate with a FLIPR-Tetra (Molecular Devices) at rt. Cell fluorescence (excitation=485 nm; emission=525 nm) was monitored following exposure to a compound. Increases in intracellular calcium are reported as the maximum fluorescence value after exposure minus the basal fluorescence value before exposure.

Data analysis: Unless otherwise indicated, data were provided as mean±standard error of the mean. For analysis of multiple groups, one-way ANOVA and posttest comparison were used. Student's t-test for paired or unpaired samples was used to evaluate the effects of experimental interventions; P<0.05 was taken as statistically significant.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Chemical compounds are described using standard nomenclature. Unless defined otherwise, all technical and scientific terms used herein have the same meaning as is commonly understood by one of skill in the art to which this invention belongs.

The Formulas include all subformulae thereof. For example Formulas I-VI include pharmaceutically acceptable salts, prodrugs and other derivatives, hydrates, polymorphs, and thereof.

All forms (for example solvates, optical isomers, enantiomeric forms, polymorphs, free compound and salts) of an active agent may be employed either alone or in combination.

In certain situations, the compounds of the Formulas may contain one or more asymmetric elements such as stereogenic centers, including chiral centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Formulas I-VI include all chiral forms, stereoisomers, diastereomers, and enantiomers of compounds of Formulas I-VI.

The term "substituted", unless otherwise indicated, means replacement of one or more hydrogens with one or more substituents. Suitable substituents include, for example, hydroxyl, $C_6$-$C_{12}$ aryl, $C_3$-$C_{20}$ cycloalkyl, $C_1$-$C_{20}$ alkyl, halogen, $C_1$-$C_{20}$ alkoxy, $C_1$-$C_{20}$ alkylthio, $C_1$-$C_{20}$ haloalkyl, $C_6$-$C_{12}$ haloaryl, pyridyl, cyano, thiocyanato, nitro, amino, $C_1$-$C_{12}$ alkylamino, $C_1$-$C_{12}$ aminoalkyl, acyl, sulfoxyl, sulfonyl, amido, or carbamoyl.

A dash ("-") that is not between two letters or symbols is used to indicate a point of attachment for a substituent. For example, —(CH$_2$)C$_3$-C$_7$cycloalkyl is attached through carbon of the methylene (CH$_2$) group.

"Acyl" is an a group of the formula HC(O)—, alkyl-C(O)— or cycloalkyl-C(O)—, in which alkyl and cycloalkyl carry the definitions set forth in this section. Acyl groups are covalently bound to the parent moiety via a single bond to the carbon of the acyl carbonyl. Non-limiting examples of suitable acyl groups include formyl, acetyl and propanoyl.

"Alkyl" is a branched or straight chain saturated aliphatic hydrocarbon group, having the specified number of carbon atoms, generally from 1 to about 12 carbon atoms. The term C$_1$-C$_4$alkyl as used herein indicates an alkyl group having from 1 to about 4 carbon atoms. Other embodiments include alkyl groups having from 1 to 8 carbon atoms, 1 to 6 carbon atoms or from 1 to 2 carbon atoms, e.g., C$_1$-C$_8$ alkyl, C$_1$-C$_6$ alkyl, and C$_1$-C$_2$ alkyl.

"Alkenyl" is a straight or branched hydrocarbon chain comprising one or more unsaturated carbon-carbon double bonds, which may occur in any stable point along the chain. Alkenyl groups described herein have the indicated number of carbon atoms. C$_2$-C$_6$ alkenyl indicates an alkenyl group of from 2 to about 6 carbon atoms. When no number of carbon atoms is indicated, alkenyl groups described herein typically have from 2 to about 12 carbon atoms, though lower alkenyl groups, having 8 or fewer carbon atoms, are preferred. Examples of alkenyl groups include ethenyl, propenyl, and butenyl groups.

"Alkynyl" is a straight or branched hydrocarbon chain comprising one or more carbon-carbon triple bonds, which may occur in any stable point along the chain. Alkynyl groups described herein have the indicated number of carbon atoms. C$_2$-C$_6$ alkynyl indicates an alkynyl group of from 2 to about 6 carbon atoms. When no number of carbon atoms is indicated, alkynyl groups described herein typically have from 2 to about 12 carbons.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups include, for example, methoxy groups.

"Alkylthio" indicates an alkyl group as defined above with the indicated number of carbon atoms attached through a sulfhydryl bridge (—SH—). Examples of alkylthio include, but are not limited to, methylthio, ethylthio, and isopropyl thio. Likewise "alkylsulfinyl" is an alkyl group as defined above with the indicated number of carbon atoms attached through a sulfinyl bridge (—S(O)—) via a single covalent bond to the sulfur atom and "alkylsulfonyl" is a group attached through a sulfonyl (—S(O)$_2$—) bridge.

"Aryl" indicates an aromatic group containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and biphenyl.

In the term "(aryl)alkyl," aryl and alkyl are as defined above, and the point of attachment to the parent moiety is on the alkyl group. Examples of (aryl)alkyl groups include piperonyl and (phenyl)alkyl groups such as benzyl, phenylethyl, and R-phenylisopropyl.

"Arylamino" is an aryl-NH— group. The arylamino group is covalently bound to the parent moiety via a single bond from the nitrogen atom. The nitrogen atom is optionally substituted. "Aryloxy" is an aryl-O— group. The aryloxy group is covalently bound to the parent moiety via a single bond from the oxygen atom. "Arylsulfonyl" is an aryl-S(O$_2$)— group. The bond to the parent moiety is through the sulfonyl.

"Cyano" is the radical —CN.

"Cycloalkyl" indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane. A bicyclic cycloalkyl" is a saturated bicyclic group having only carbon ring atoms. Bicycloalkyl groups have 7 to 12 carbon ring atoms. Examples of bicycloalkyl groups include s-endonorbornyl and carbamethylcyclopentane.

"Cycloalkoxy" is a cycloalkyl-O—, wherein cycloalkyl is as defined above. Cycloalkoxy groups include cyclopentyloxy.

"Halo" or "halogen" indicates fluoro, chloro, bromo, and iodo.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom "Sulfonyl" is the bivalent radical —SO$_2$—.

"Thiol" is the radical —SH.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985). Other exemplary salts are amine salts of the phosphonic or phosphinic acid group including organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, aspargeinate, glutamate, and the like; and combinations comprising one or more of the foregoing salts.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

ABBREVIATIONS

5'-AMP, adenosine 5'-monophosphate;
CSQ, calsequestrin;
DIBAL-H, diisobutylaluminium hydride;
DMEM, Dulbecco's modified Eagle medium;
FS, fractional shortening;
HEPES, N-2-hydroxyethylpiperazine-N'-2-ethanesulfonic acid;
HPLC, high performance liquid chromatography;
HRMS, high resolution mass spectroscopy;
LV, left ventricular;
LVEDD, left ventricular end-diastolic diameter;
LVESD, left ventricular end-systolic diameter;
MRS2339, (1'S,2'R,3'S,4'R,5'S)-4-(6-amino-2-chloro-9H-purin-9-yl)-1-[phosphoryloxymethyl]bicyclo[3.1.0]hexane-2,3-diol;
NS, normal saline;
PLC, phospholipase C;
SAR, structure activity relationship;
TBAF, tetrabutylammonium fluoride;
TBAP, tetrabutylammonium phosphate;
TBDPS-Cl, tert-butyl(chloro)diphenylsilane;
THF, tetrahydrofuran;
TEAA, triethylammonium acetate.

Schemes

Scheme 1: Reagents and Conditions: a) tert-Butylchlorodiphenylsilane, imidazole, DMAP, an. $CH_2Cl_2$, 93%; b) DIBAL-H, an. THF, 82%; c) Methanesulfonyl chloride, triethylamine, an. $CH_2Cl_2$, 96%; d) NaI, 65° C., an. 1,4-dioxane, 95%; e) Triethylphosphite, 110° C.; f) TBAF, THF, 88%.

Scheme 2: Reagents and Conditions: a) Triphenylphosphine, 2,6-dichloropurine, diisopropyl azodicarboxylate, an. THF, 75%; b) 2 M $NH_3$ in i-PrOH, 70° C., 80% for 9, 79% for 11; c) Iodotrimethylsilane, an. $CH_2Cl_2$, 23% for 4 and 27% for 5; d) Triphenylphosphine, 6-chloropurine, diisopropyl azodicarboxylate, an. THF, 87%.

Scheme 3: Reagents and Conditions: a) Dess-Martin periodinane, an. $CH_2Cl_2$, 80%; b) Tetraisopropyl methylenediphosphonate, NaH, an. THF, 83%; c) 2 M $NH_3$ in i-PrOH, 70° C., 80%; d) 10% Pd/C, $H_2$ (3 bar), MeOH:2M aq. NaOH (1:1, v/v), 79%; e) Iodotrimethylsilane, an. $CH_2Cl_2$, 47% for 10 and 28% for 7; d) Triphenylphosphine, 6-chloropurine, diisopropyl azodicarboxylate, an. THF, 87%.

Scheme 4: Reagents and Conditions: a) Dess-Martin periodinane, an. $CH_2Cl_2$, 72%; b) Tetraisopropyl methylenediphosphonate, NaH, an. THF, 48%; c) TBAF, THF, 88%; d) Triphenylphosphine, 6-chloropurine, diisopropyl azodicarboxylate, an. THF, 85%; e) 2 M $NH_3$ in i-PrOH, 70° C., 85%; e) Iodotrimethylsilane, an. $CH_2Cl_2$, 78%.

Scheme 5: Reagents and Conditions: a) 10% Pd/C, $H_2$ (3 bar), MeOH, 72%; b) Triphenylphosphine, 2,6-dichloropurine, diisopropyl azodicarboxylate, an. THF, 40%; c) 2 M $NH_3$ in i-PrOH, 70° C., 71%; d) Iodotrimethylsilane, an. $CH_2Cl_2$, 45%.

Scheme 6: Reagents and Conditions: a) $CBr_4$, triphenylphosphine, triethylamine, 81%; b) Diethylmethylphosphite, 110° C., 95%; c) TBAF, THF, 91%, d) Triphenylphosphine, 2,6-dichloropurine, diisopropyl azodicarboxylate, an. THF, 75%; e) 2 M $NH_3$ in i-PrOH, 70° C., 60%; f) Iodotrimethylsilane, an. $CH_2Cl_2$, 20% combined yield.

Scheme 7: A) Retrosynthetic analysis of 5'-phosphonate and 5'-methyl phosphonates of (N)-methanocarba adenine or 2-Cl adenine derivatives. B) Retrosynthetic analysis of saturated and unsaturated long chain 5'-phosphonates of (N)-methanocarba adenine or 2-Cl adenine derivatives.

Scheme 1a: Reagents and Conditions: a) 10% aqueous trifluoroacetic acid, 60%; b) i) Thiophosphoryl chloride, 1,8-bis-(dimethylamino)naphthalene (proton sponge), pyridine, ii) Quenching the reaction with tetraethylammoniumbicorbonate (TEAB); c) i) Thiophosphoryl chloride, 1,8-bis-(dimethylamino)naphthalene (proton sponge), pyridine, ii) Quenching the reaction with EtOH; d) Triphenylphosphine, $I_2$, imidazole, anhydrous THF, 74%, e) Dowex-50, MeOH: $H_2O$ (1:1, v/v), 70° C.; f) Sodium-O,O-diethylthiophosphate, EtOH; THF; g) Trisodium thiophosphate, $H_2O$, 57%; h) Diethyl dithiophosphate potassium salt, DMF.

Scheme 2a: Reagents and Conditions: a) 2 M $NH_3$ in i-PrOH, 70° C., 68%; b) $LiBD_4$, anhydrous THF, 72%; c) i) Di-t-butylN,N'-diethylphosphoramidite, anhydrous THF, tetrazole; ii) m-chloroperbenzoic acid, 76%; d) Dowex-50 resin, MeOH:$H_2O$ (1:1, v/v) 70° C.

Scheme 3a: Reagents and Conditions: a) Triphenylphosphine, 6-chloro-2-iodopurine, diisopropyl azodicarboxylate, an. THF, 70%; b) 2 M $NH_3$ in i-PrOH, 70° C., 64%; c) Iodotrimethylsilane, an. $CH_2Cl_2$, 49% for 7; d) Dowex-50, MeOH:$H_2O$ (1:1, v/v), 70° C., 3 h, 49% for 16, e) i) Trimethylsilylacetylene, $Pd(Ph_3)_4$, CuI, TEA, anhydrous DMF ii) TBAF, anhydrous THF.

Scheme 4a: Reagents and Conditions: a) Dess-Martin periodinane, an. $CH_2Cl_2$; b) Tetraethyl methylenediphosphonate, NaH, an. THF; c) 2 M $NH_3$ in i-PrOH, 70° C.; d) O-nitrobenzenesulfonylhydrazide, $Et_3N$, $CH_2Cl_2$; e) Dowex-50, MeOH:$H_2O$ (1:1, v/v), 70° C.

TABLE 1

Phosphonate analogues: structure and effects on in vivo heart function as determined by echocardiography-derived FS in CSQ heart failure mice.

| No | Structure | FS in % in CSQ Mice[a] | n = |
|----|-----------|------------------------|-----|
| 3  | MRS2339   | 15.47 ± 1.15           | 10  |
| 4  | MRS2776   | 20.25 ± 1.19           | 8   |
| 5  | 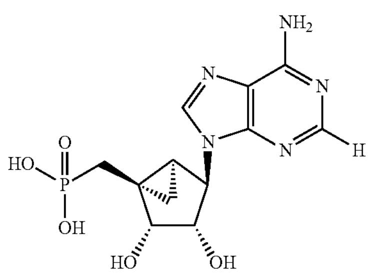          | 16.23 ± 0.93           | 13  |
| 7  | 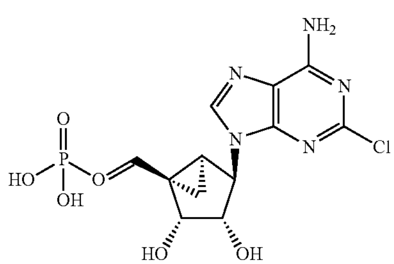          | 12.12 ± 1.2            | 11  |
| 8  | 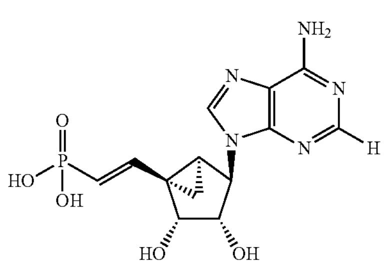          | 13.88 ± 2.12           | 8   |
| 9  | MRS2925   | 19.26 ± 1.23           | 16  |
| 10 |           | 11.15 ± 1.44           | 12  |
| 11 |           | 15.0 ± 1.2             | 10  |
| 12 |           | ND                     |     |

[a] at 3.3 μM. The vehicle control mice displayed a % FS of 13.78 ± 1.19% (n = 16).

ND- not determined.

TABLE 2

Novel phosphate and phosphonate analogues: structure and effects on in vivo heart function as determined by echocardiography-derived FS in CSQ heart failure mice.

| No | Structure | FS in % in CSQ Mice[a] | n = |
|---|---|---|---|
| | Charged nucleotide | | |
| 4a | MRS2977 | 14.33 ± 3.77 | 4 |
| 5a | MRS4073 | | |
| 6a | MRS4069 | | |
| 7a | MRS2972 | 10.33 ± 1.77 | 5 |
| | Masked nucleotides | | |
| 8a | MRS4074 | | |
| 9a | MRS2944 | 8.58 ± 2.09 | 4 |
| 10a | MRS4075 | | |
| 11a | MRS2978 | 12.94 ± 0.98 | 6 |

TABLE 2-continued

Novel phosphate and phosphonate analogues: structure and effects on in vivo heart function as determined by echocardiography-derived FS in CSQ heart failure mice.

| No | Structure | FS in % in CSQ Mice[a] | n = |
|---|---|---|---|
| 12a | 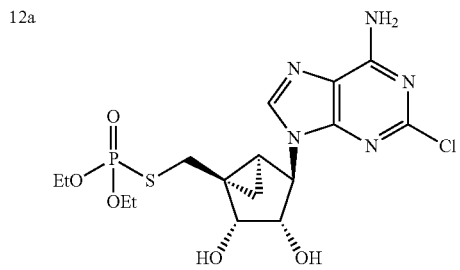 MRS4076 | | |
| 13a | 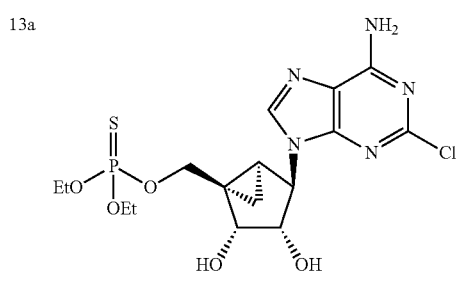 MRS4078 | | |
| 14a | 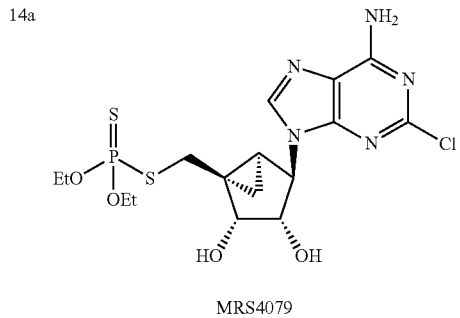 MRS4079 | | |
| 15a | 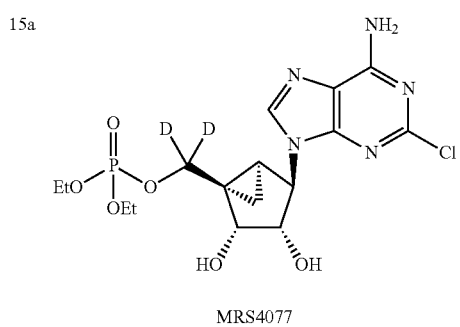 MRS4077 | | |
| 16a | 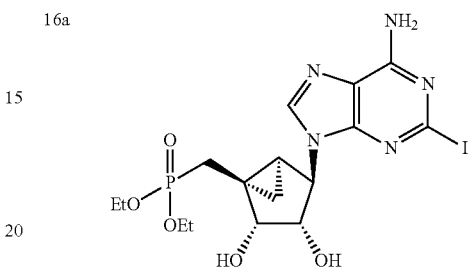 MRS4071 | ND, No effect expected | |
| 17a | 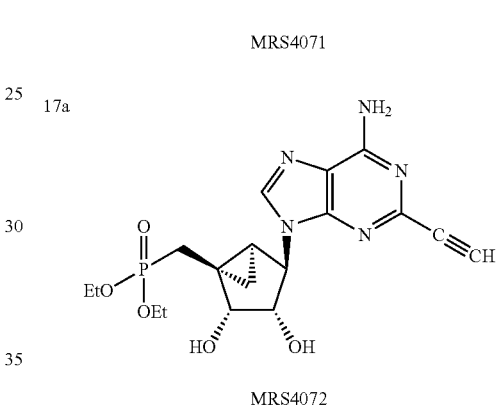 MRS4072 | | |

[a] at 10 μM. The vehicle control mice displayed a %FS of 7.13 ± 1.49% (n = 4). The CSQ mice used here were phenotypically more severe than the mice used for data in Table 1.[2]
ND- not determined.

Chart 1

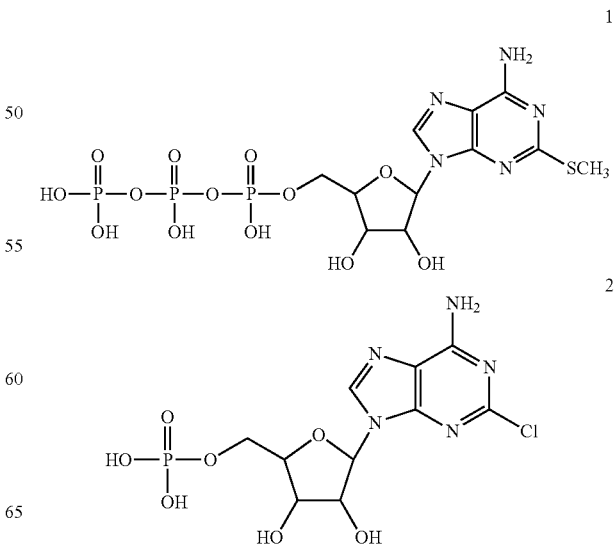

-continued
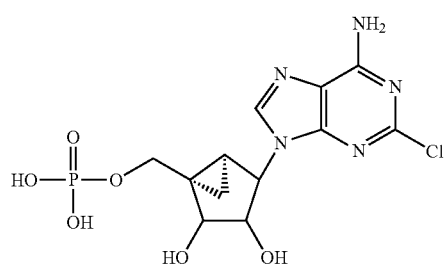
3
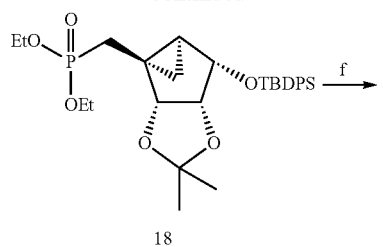
18
Scheme 1
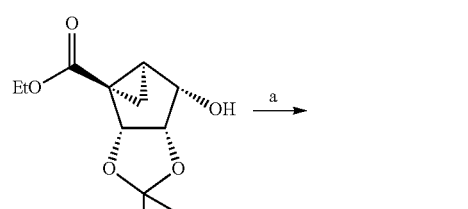
13
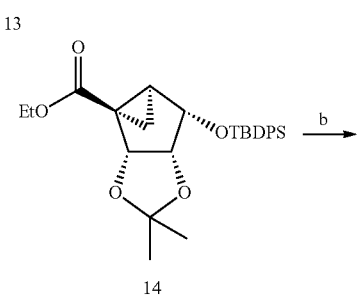
14
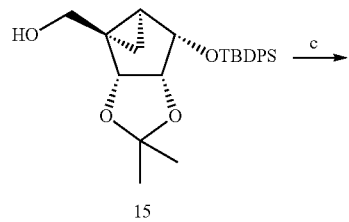
15
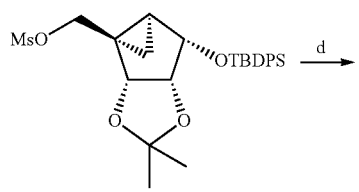
16
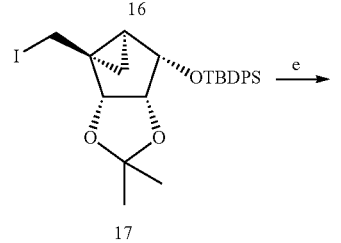
17
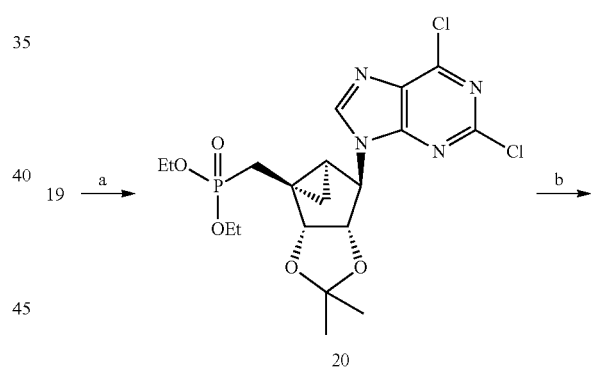
19
Scheme 2
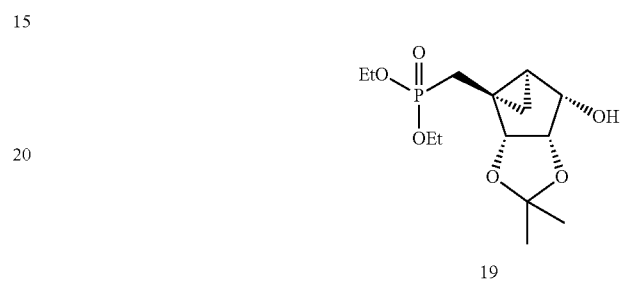
20
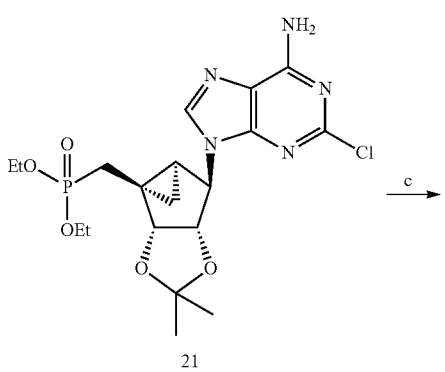
21

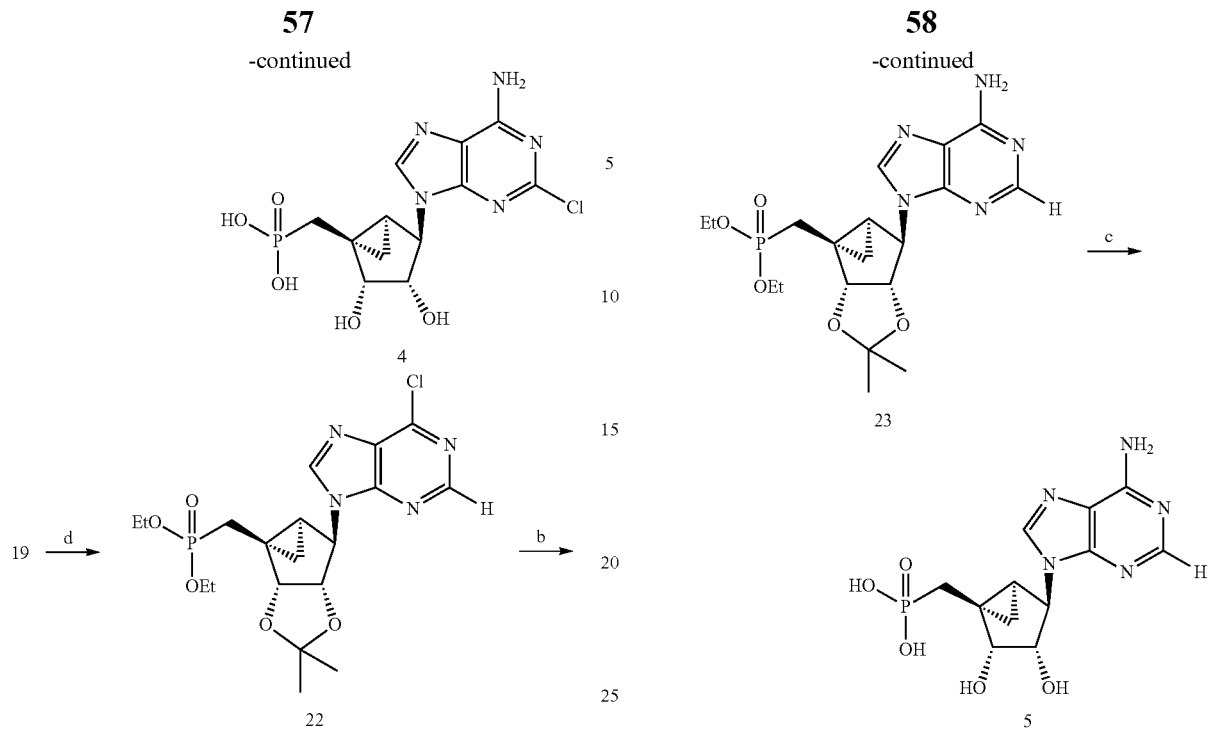
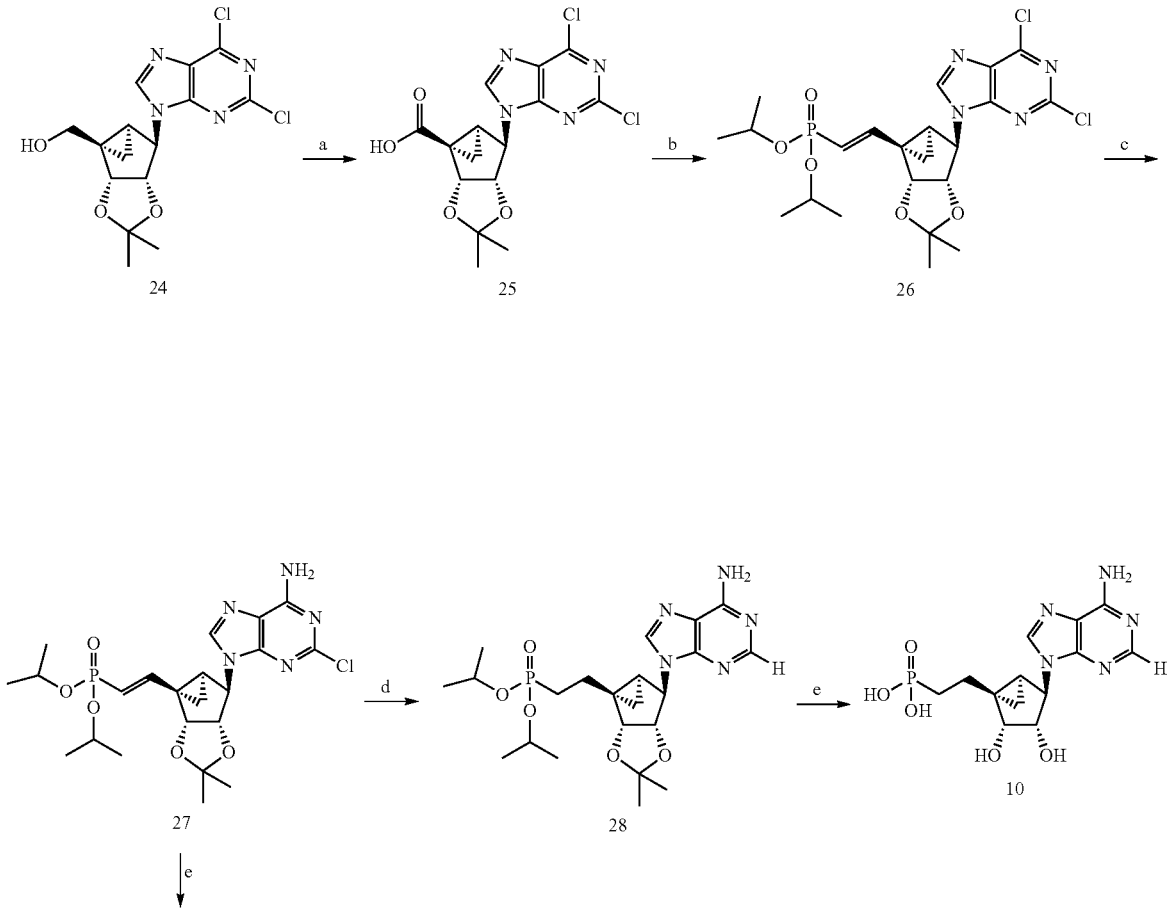
Scheme 3

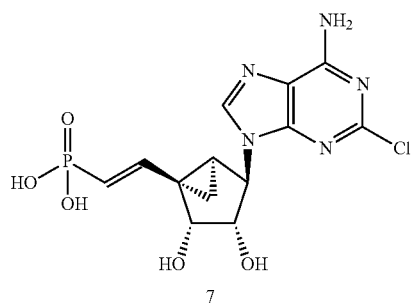
7
Scheme 4
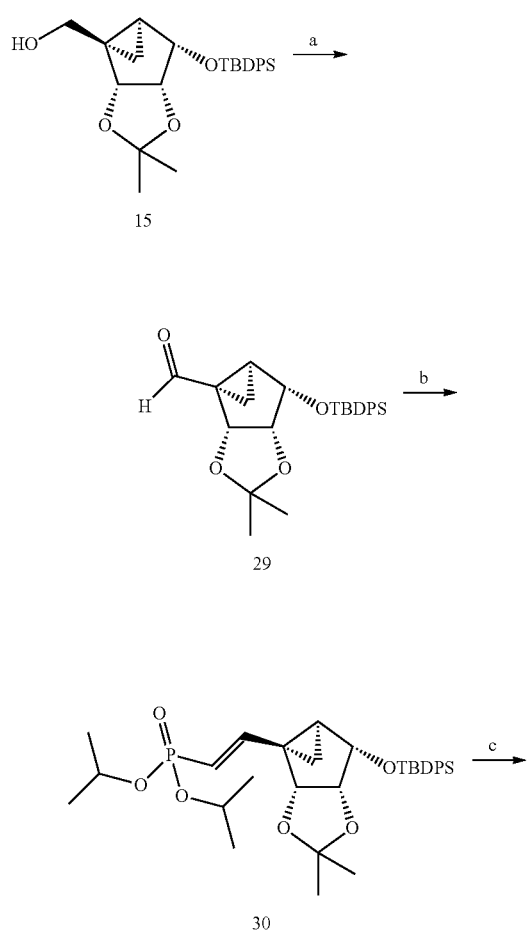
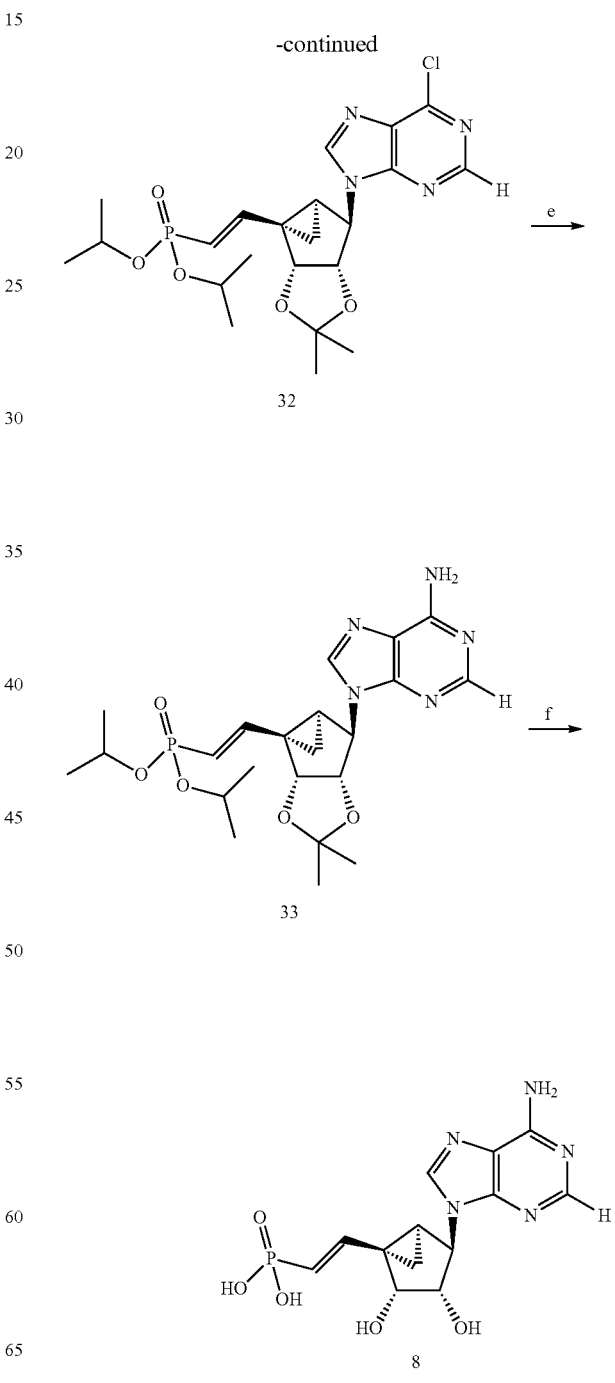

Scheme 5
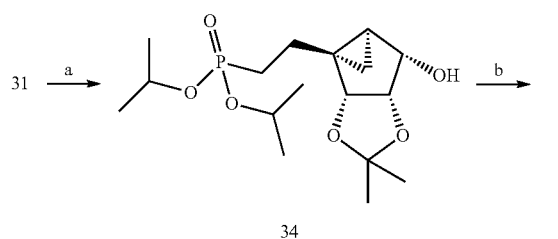
34
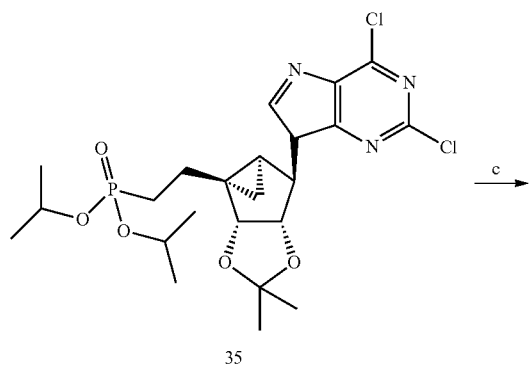
35
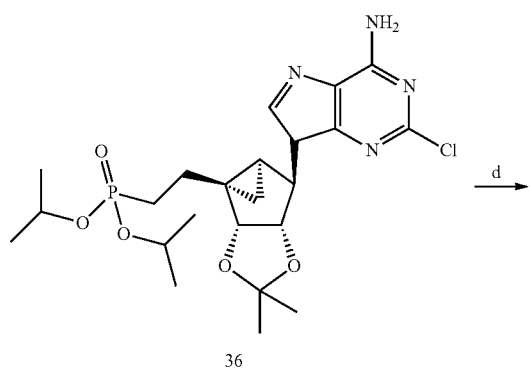
36
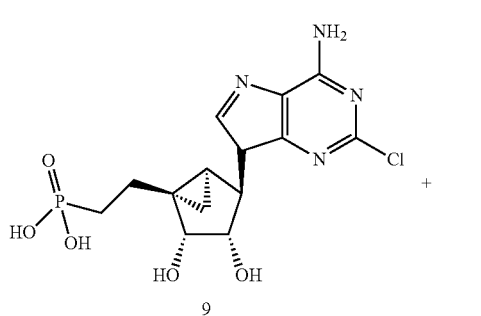
9
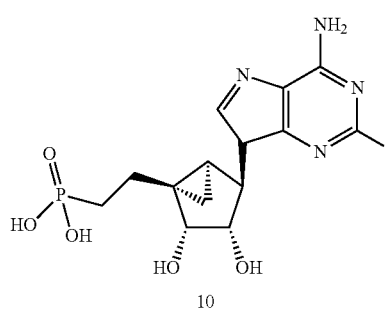
10
Scheme 6
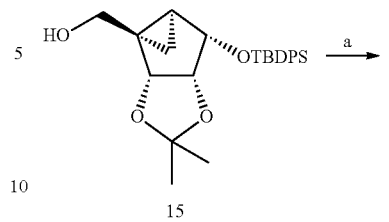
15
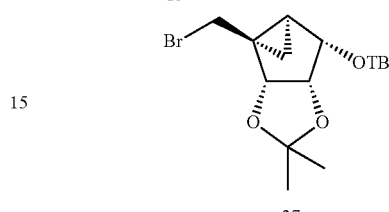
37
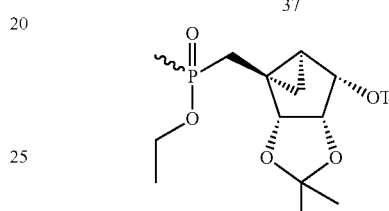
38
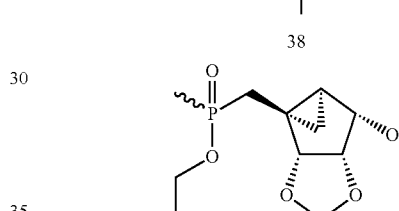
39
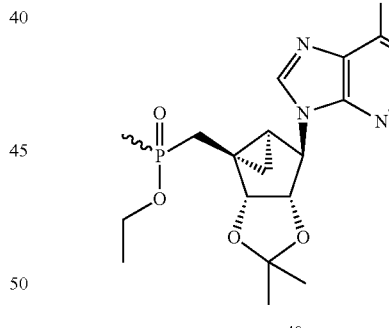
40
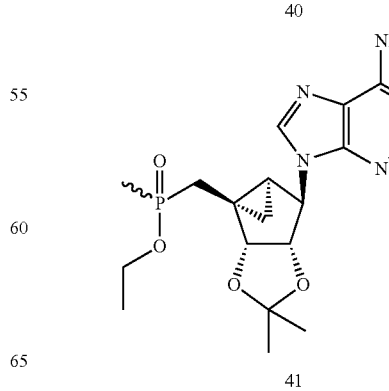
41

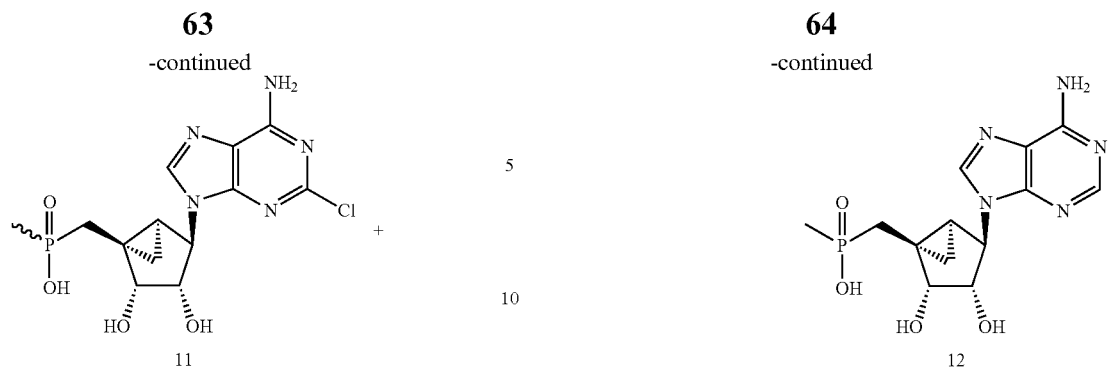
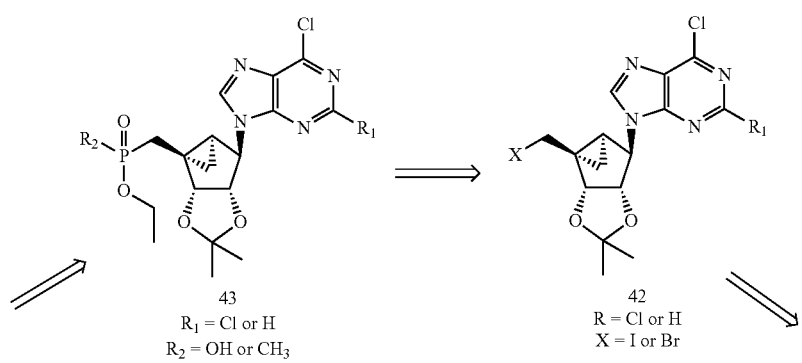
Scheme 7A
Route A
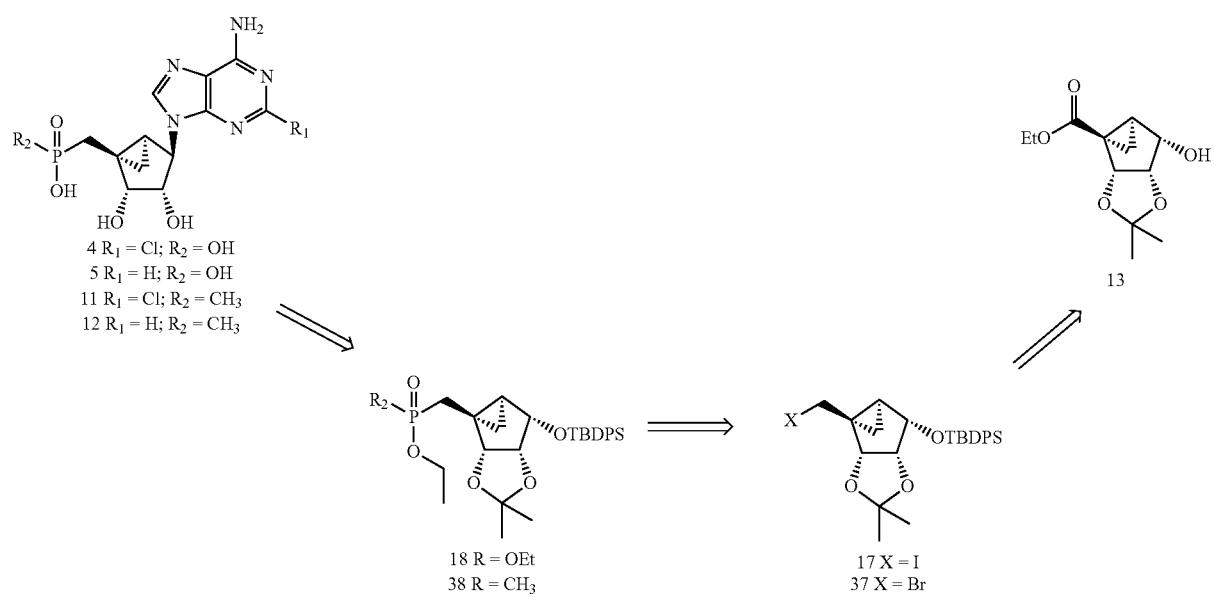
Route B

Scheme 7B
Route C
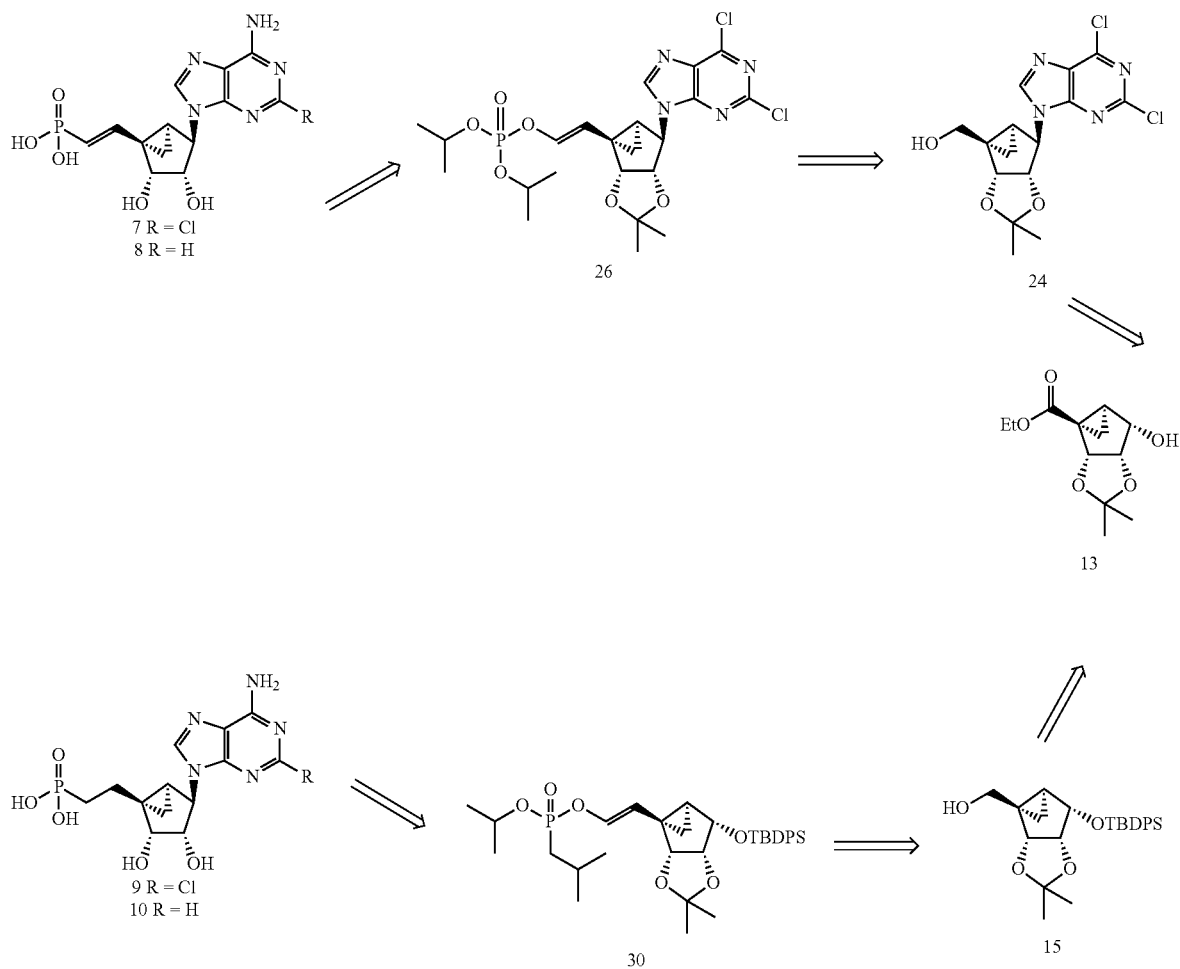
Route D
Scheme 1a
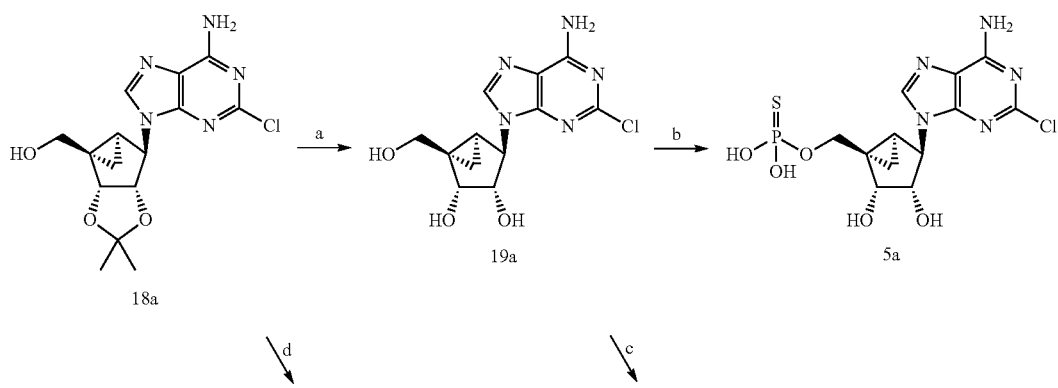

-continued
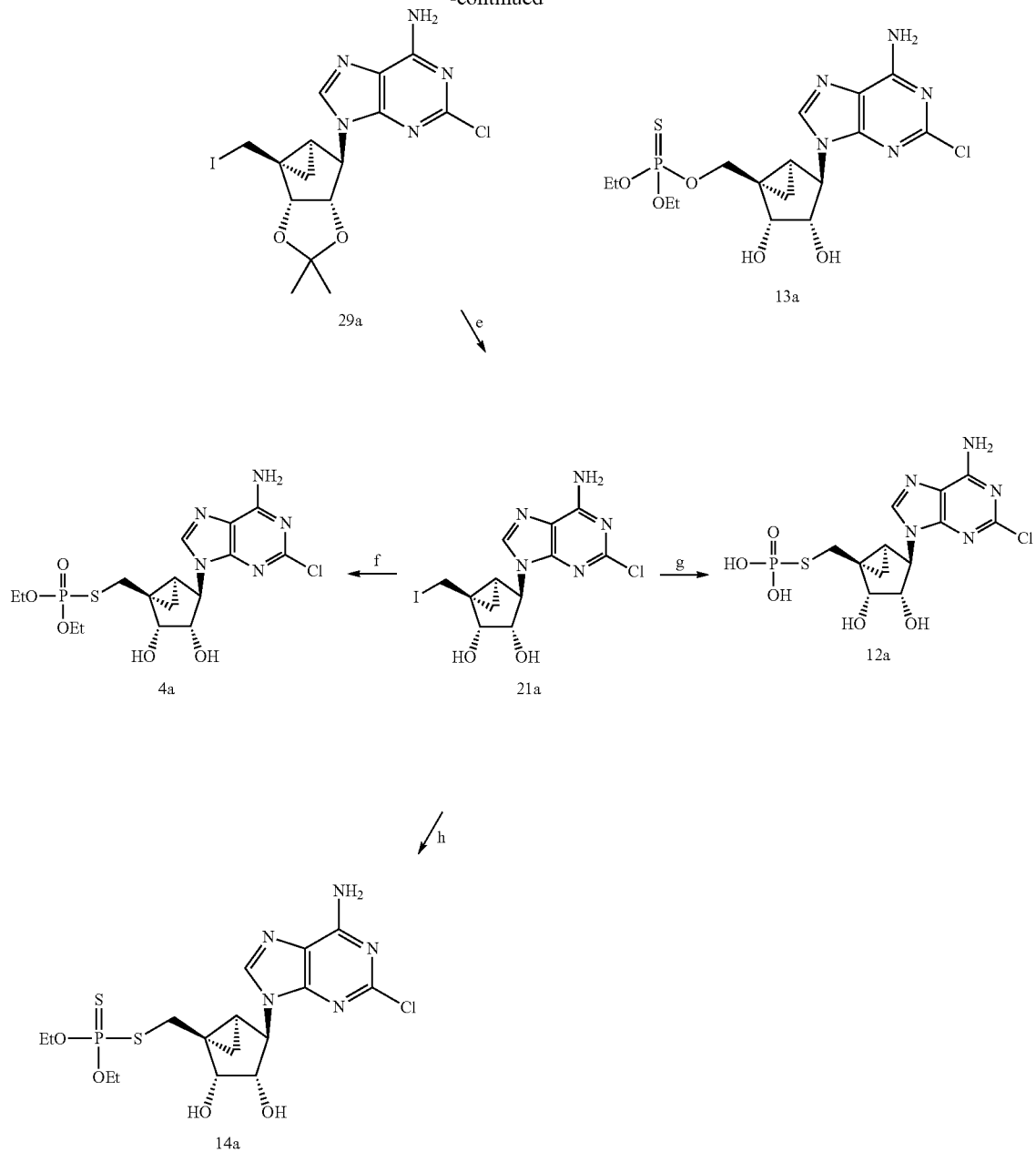
Scheme 2a
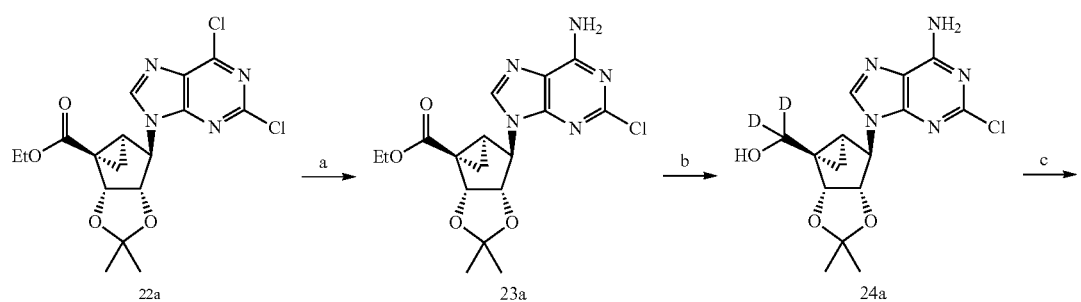

-continued
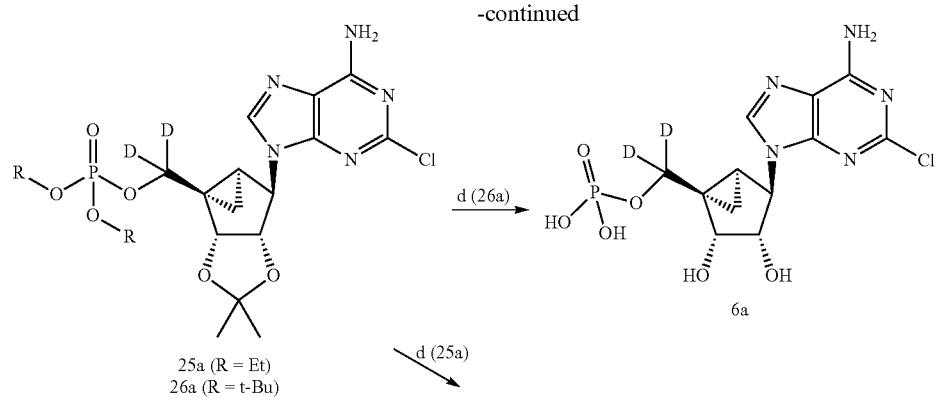
25a (R = Et)
26a (R = t-Bu)
6a
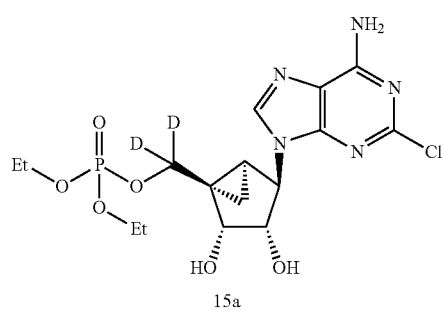
15a
Scheme 3a
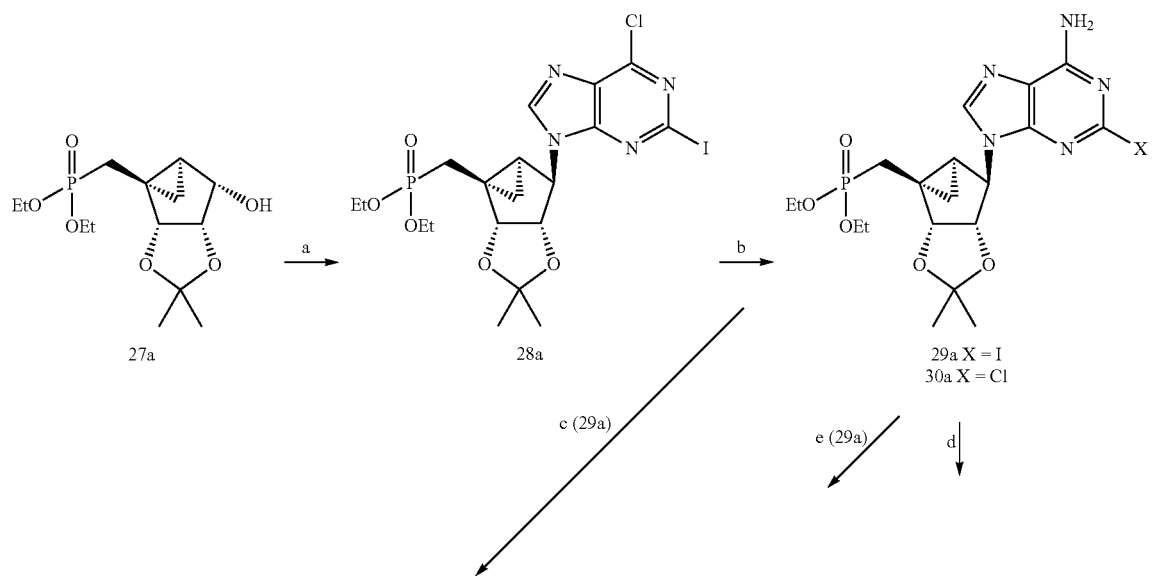
27a
28a
29a X = I
30a X = Cl

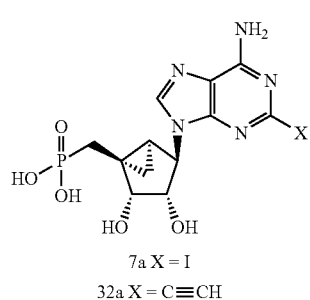
7a X = I
32a X = C≡CH
-continued
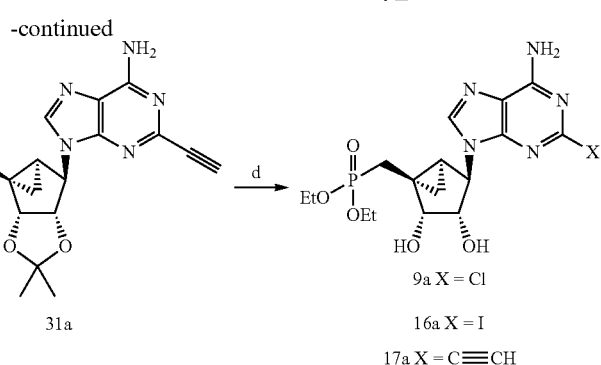
31a
9a X = Cl
16a X = I
17a X = C≡CH
Scheme 4a
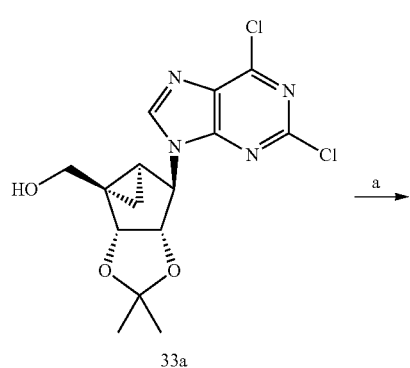
33a
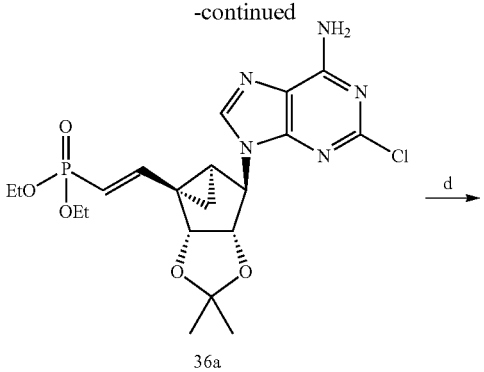
36a
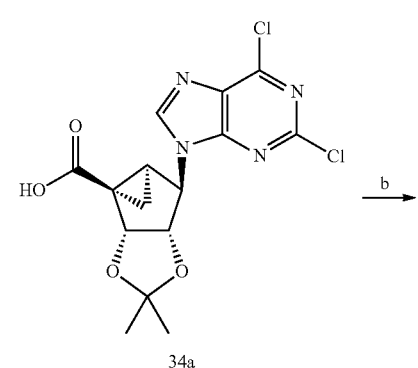
34a
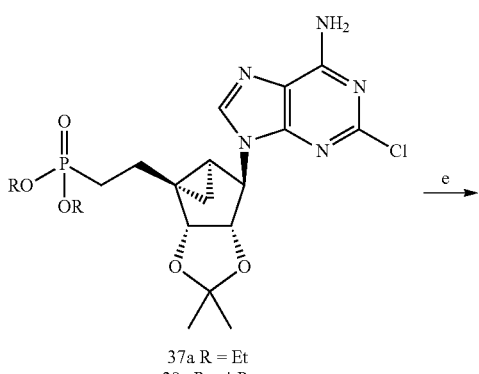
37a R = Et
38a R = i-Pr
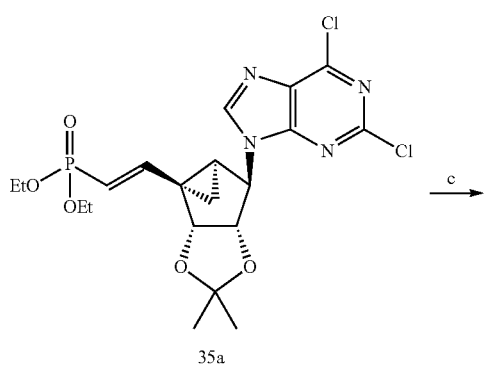
35a
-continued
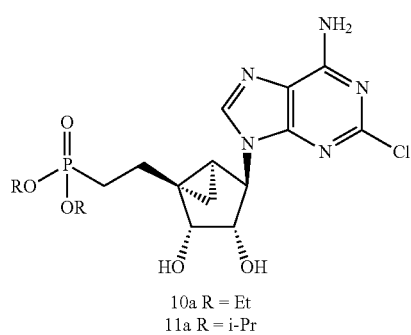
10a R = Et
11a R = i-Pr
The invention claimed is:
1. A phosphonate or phosphinate N-methanocarba derivative of AMP selected from,

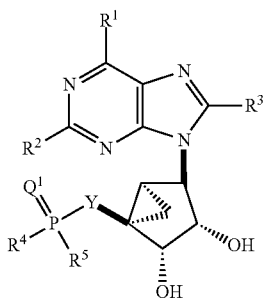

(1)

wherein $Q^1$ is O or S;

- $R^1$ is hydrogen, optionally substituted alkyl, optionally substituted cycloalkyl, halogen, or $N(R^6)_2$, wherein each $R^6$ is independently hydrogen, optionally substituted alkyl, or optionally substituted cycloalkyl;
- $R^2$ is hydrogen, optionally substituted alkyl, optionally substituted cycloalkyl, optionally substituted alkynyl, $N(R^6)_2$, or halogen;
- $R^3$ is hydrogen, optionally substituted alkyl, $N(R^6)_2$, or halogen;
- $R^4$ is hydroxyl, optionally substituted alkyl, optionally substituted alkoxy, optionally substituted aryl, optionally substituted —Oaryl, or $N(R^6)_2$;
- $R^5$ is hydroxyl, optionally substituted alkyl, optionally substituted alkoxy, optionally substituted aryl, or optionally substituted —Oaryl; or
  alternatively, $R^4$ and $R^5$ form a 5- or 6-membered cyclic structure with the phosphorus atom where the cyclic structure contains at least two oxygen atoms attached to the phosphorous atom and at least 2 carbon atoms, wherein the carbon atom or atoms closest to the phosphorous atom are optionally substituted with alkyl or aryl; and
- Y is a linking group linked to the phosphorus atom by a carbon atom, and is optionally substituted $C_1$-$C_6$ alkylene, optionally substituted $C_1$-$C_6$ alkenylene, optionally substituted $C_1$-$C_6$ alkynylene, or optionally substituted —$C_1$-$C_6$ alkylene-O—$C_1$-$C_6$ alkylene;

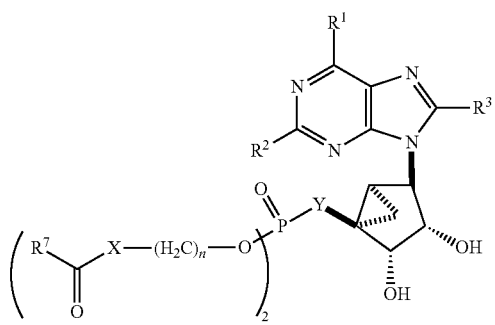

(II)

wherein X is O or S; n is 1, 2, or 3; and $R^7$ is optionally substituted alkyl or optionally substituted aryl;

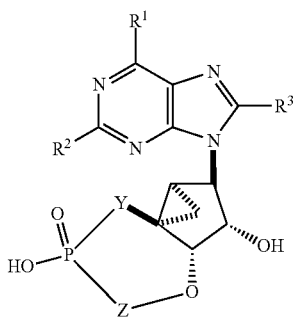

(III)

wherein Z is a bond or —O—C(=O)— where the carbonyl carbon is bonded to the oxygen of the bicycle group and the oxygen is bonded to the phosphorus atom;

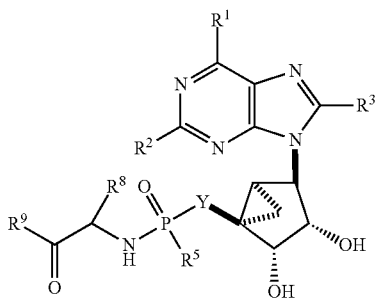

(IV)

wherein $R^8$ is hydrogen or optionally substituted alkyl; $R^8$ is optionally substituted alkyl, optionally substituted alkoxy, or optionally substituted aryl; and $R^9$ is methoxy;

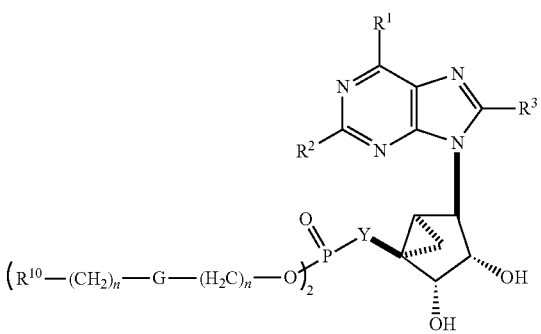

(V)

wherein G is O or S—S; and $R^{10}$ is hydrogen, hydroxyl, optionally substituted alkyl, optionally substituted alkoxy, or optionally substituted aryl;

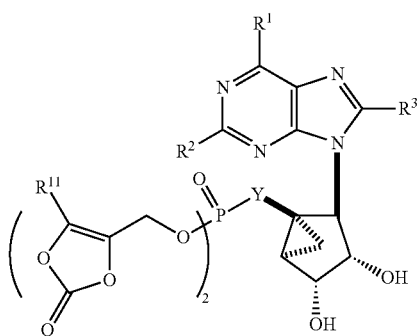

(VI)

wherein R¹¹ is hydrogen, optionally substituted alkyl, or optionally substituted aryl, and

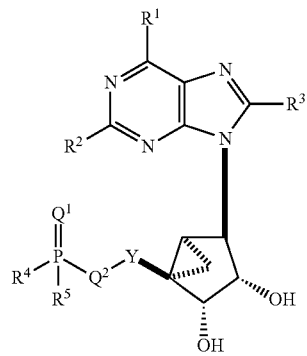

(VII)

wherein
Q¹ is O or S;
Q² is O or S;
with the proviso that when Q¹ and Q² are both O, and Formula (VII) is not enriched with deuterium, then R⁴ and R⁵ are not both hydroxyl,
a deuterium enriched isomer thereof, or a pharmaceutically acceptable salt thereof.

2. The phosphonate or phosphinate N-methanocarba derivative of AMP of claim 1, selected from Formula (I) or (VII).

3. The phosphonate or phosphinate N-methanocarba derivative of AMP of claim 1, Formula (I) wherein Q¹ is O; R¹ is N(R⁶)₂ wherein each R⁶ is hydrogen; R² is halogen; R³ is hydrogen; R⁴ is hydroxyl or optionally substituted alkoxy; and R⁵ is hydroxyl or optionally substituted alkoxy.

4. The phosphonate or phosphinate N-methanocarba derivative of AMP of claim 1, Formula (I) wherein Q¹ is O; R¹ is N(R⁶)₂ wherein each R⁶ is hydrogen; R² is halogen; R³ is hydrogen; R⁴ is hydroxyl or optionally substituted alkoxy; R⁵ is hydroxyl or optionally substituted alkoxy; and Y is a $C_1$-$C_6$ alkylene.

5. The phosphonate or phosphinate N-methanocarba derivative of AMP of claim 1, Formula (VII) wherein Q¹ is O; Q² is S; R¹ is N(R⁶)₂ wherein each R⁶ is hydrogen; R² is halogen; R³ is hydrogen; R⁴ is hydroxyl or optionally substituted alkoxy; R⁵ is hydroxyl or optionally substituted alkoxy; and Y¹ is a $C_1$-$C_6$ alkylene.

6. The phosphonate or phosphinate N-methanocarba derivative of AMP of claim 1, Formula (VII) wherein Q¹ is S; Q² is O; R¹ is N(R⁶)₂ wherein each R⁶ is hydrogen; R² is halogen; R³ is hydrogen; R⁴ is hydroxyl or optionally substituted alkoxy; R⁵ is hydroxyl or optionally substituted alkoxy; and Y¹ is a $C_1$-$C_6$ alkylene.

7. The phosphonate or phosphinate N-methanocarba derivative of AMP of claim 1, which is

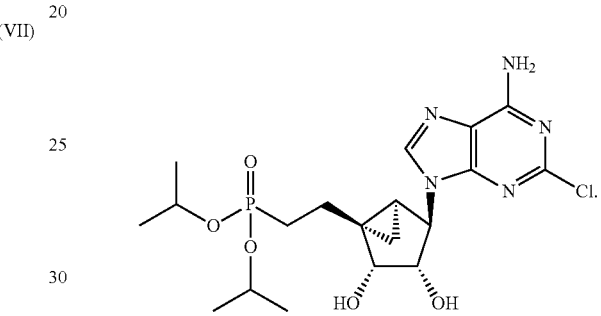

8. The phosphonate or phosphinate N-methanocarba derivative of AMP of claim 1, which is

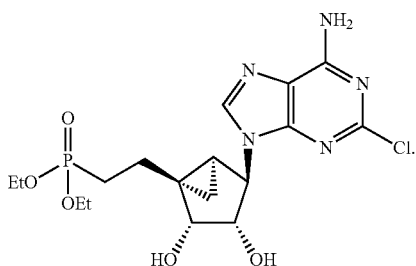

9. A pharmaceutical composition comprising the phosphonate or phosphinate N-methanocarba derivative of AMP of claim 1 and a pharmaceutically acceptable excipient.

* * * * *